US010780128B2

(12) United States Patent
Lim

(10) Patent No.: US 10,780,128 B2
(45) Date of Patent: Sep. 22, 2020

(54) MESENCHYMAL STEM CELL PARTICLES

(71) Applicant: **AGENCY FOR SCIENCE, TECHNOLOGY AND RESEARCH (A*STAR)**, Singapore (SG)

(72) Inventor: Sai Kiang Lim, Singapore (SG)

(73) Assignee: **AGENCY FOR SCIENCE, TECHNOLOGY AND RESEARCH (A*STAR)**, Singapore (SG)

( * ) Notice: Subject to any disclaimer, the term of this patent is extended or adjusted under 35 U.S.C. 154(b) by 415 days.

(21) Appl. No.: 14/444,105

(22) Filed: Jul. 28, 2014

(65) Prior Publication Data

US 2015/0190430 A1    Jul. 9, 2015

Related U.S. Application Data

(63) Continuation of application No. 12/918,122, filed as application No. PCT/SG2009/000062 on Feb. 21, 2009.

(60) Provisional application No. 61/066,671, filed on Feb. 22, 2008.

(51) Int. Cl.
| | | |
|---|---|---|
| *A61K 35/00* | (2006.01) | |
| *A61K 35/28* | (2015.01) | |
| *A61K 35/12* | (2015.01) | |
| *C12N 5/0775* | (2010.01) | |
| *A61K 9/00* | (2006.01) | |
| *A61K 9/10* | (2006.01) | |
| *A61K 47/24* | (2006.01) | |
| *A61K 47/28* | (2006.01) | |

(52) U.S. Cl.
CPC ............ *A61K 35/28* (2013.01); *A61K 9/0019* (2013.01); *A61K 9/10* (2013.01); *A61K 35/12* (2013.01); *A61K 47/24* (2013.01); *A61K 47/28* (2013.01); *C12N 5/0663* (2013.01); *A61L 2300/30* (2013.01)

(58) Field of Classification Search
None
See application file for complete search history.

(56) References Cited

U.S. PATENT DOCUMENTS

2006/0116321 A1 * 6/2006 Robbins ................ A61K 35/16
424/85.2
2006/0286089 A1   12/2006 Berenson et al.
2013/0243820 A1 * 9/2013 Taylor ................ G06F 17/2765
424/277.1

FOREIGN PATENT DOCUMENTS

WO      2008/020815 A      2/2008
WO   WO 2014013258    *   1/2014

OTHER PUBLICATIONS

Caplan et al., Journal of Cellular Biochemistry, 98(5):1076-1084 (2006). "Mesenchymal stem cells as trophic mediators."
Horn et al., Neuroscience Research, 63(1):35-41 (2009). "Conditioned medium from mesenchymal stem cells induces cell death in organotypic cultures of rat hippocampus and aggravates lesion in a model of oxygen and glucose deprivation."
Lian et al., Cell Research, 18(Suppl. 1) (2008). "Deriving clinically compliant mesenchymal stem cells (MSC) from differentiated human ESCs and elucidating MSC paracrine proteome."
Nakanishi et al., Biochemical and Biophysical Research Communications, 374(1):11-16 (2008). "Activation of cardiac progenitor cells through paracrine effects of mesenchymal stem cells."
Oh et al., Journal of Separation Science, 30(7):1082-1087 (2007). "Miniaturized asymmetrical field-flow fractionation: Application to biological vesicles."
Sze et al., Molecular & Cellular Proteomics, 6(10):1680-1689 (2007). "Elucidating the secretion proteome of human embryonic stem cell-derived mesenchymal stem cells."
Timmers et al., Stem Cell Research, 1(2):129-137 (2008). "Reduction of myocardial infarct size by human mesenchymal stem cell conditioned medium."
Augello et al., European Cells and Materials 20:121-133 (2010). Mesenchymal stem cells: a perspective from in vitro cultures to in vivo migration and niches>.
Bara et al., Stem Cells. Jul. 2014;32(7):1713-23. "Concise review: Bone marrow-derived mesenchymal stem cells change phenotype following in vitro culture: implications for basic research and the clinic."
Chung et al., Cell Stem Cell, 2:113 (2008). "Human embryonic stem cell lines generated without embryo destruction".
Corselli et al., Stem Cells Dev. May 20, 2012;21(8):1299-308. "The tunica adventitia of human arteries and veins as a source of mesenchymal stem cells."
Crisan et al. Cell Stem Cell. Sep. 11, 2008;3(3):301-13. "A perivascular origin for mesenchymal stem cells in multiple human organs."
Gronthos et al., Blood. Dec. 15, 1994;84(12):4164-73. "The STRO-1+ fraction of adult human bone marrow contains the osteogenic precursors."
Gronthos et al., J Cell Sci. May 1, 2003;116(Pt 9):1827-35. "Molecular and cellular characterisation of highly purified stromal stem cells derived from human bone marrow."
Kaiser et al., Cytotherapy 9(5):439-450 (2007). "BM cells giving rise to MSC in culture have a heterogeneous CD34 and CD45 phenotype."
Thery et al., Nature 9:581 (2009). "Membrane vesicle as conveyors of immune reponses".

(Continued)

*Primary Examiner* — Michail A Belyavskyi
(74) *Attorney, Agent, or Firm* — Nixon Peabody LLP; Mark J. FitzGerald

(57) ABSTRACT

We describe a particle secreted by a mesenchymal stem cell and comprising at least one biological property of a mesenchymal stem cell. The biological property may comprise a biological activity of a mesenchymal stem cell conditioned medium (MSC-CM) such as cardioprotection or reduction of infarct size. The particle may comprise a vesicle or an exosome.

4 Claims, 37 Drawing Sheets

(56) References Cited

OTHER PUBLICATIONS

Tormin et al., Blood, 117(19):5067-5077 (2011). CD146 expression on primary nonhematopoietic bone marrow stem cells is correlated with in situ localization.

Keller et al., "Exosomes: From biogenesis and secretion to biological function", Immunology Letters, 107: 102-108 (2006).

\* cited by examiner

FIGURE 13

| Classifications | Proteins |
| --- | --- |
| Targeting/adhesion | Integrins $\beta1$, $\alpha3$, $\alpha7$, and $\alpha V$ |
| | MFG-E8, lactadherin |
| | Chaperones |
| | hsc70 and hsp84 |
| Membrane fusion | Annexins A1, A2, A3, A4, A5, A6 and A11 |
| | Arf3, Arf6, and Arf5 |
| | Rab5c, Rab7, and Rab10 |
| | RabGDI |
| | Rap1A and Rap2B |
| Cytoskeleton | Actin |
| | Cofilin 1 |
| | Moesin |
| | Tubulins $\alpha1$, $\alpha2$, $\beta5$, $\beta3$, and $\alpha6$ |
| Signal transduction | 14-3-3 $\varepsilon\ \gamma\ \sigma$ |
| | G$\beta$1 and G12$\alpha$ |
| Enzymes | Enolase 1 |
| | GAPDH |
| | Pyruvate kinase |
| Histones | H2B, H2A, and H4 |
| Others | Translation elongation factor 1$\alpha$ |
| | lamp2 |
| | C3 |

FIGURE 23
CM
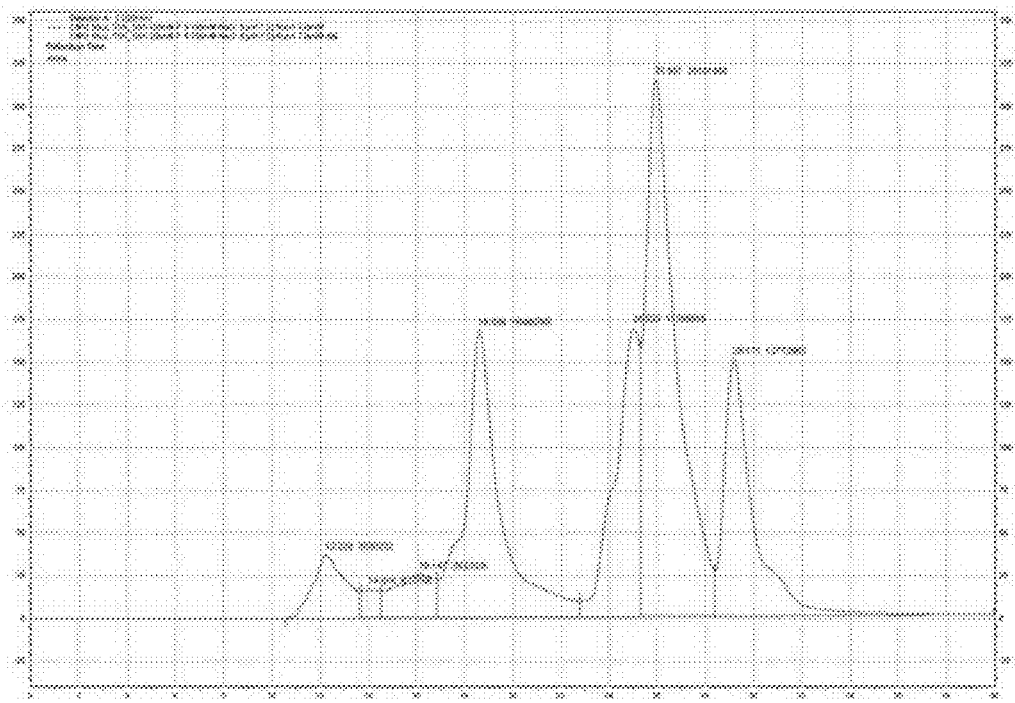
NCM
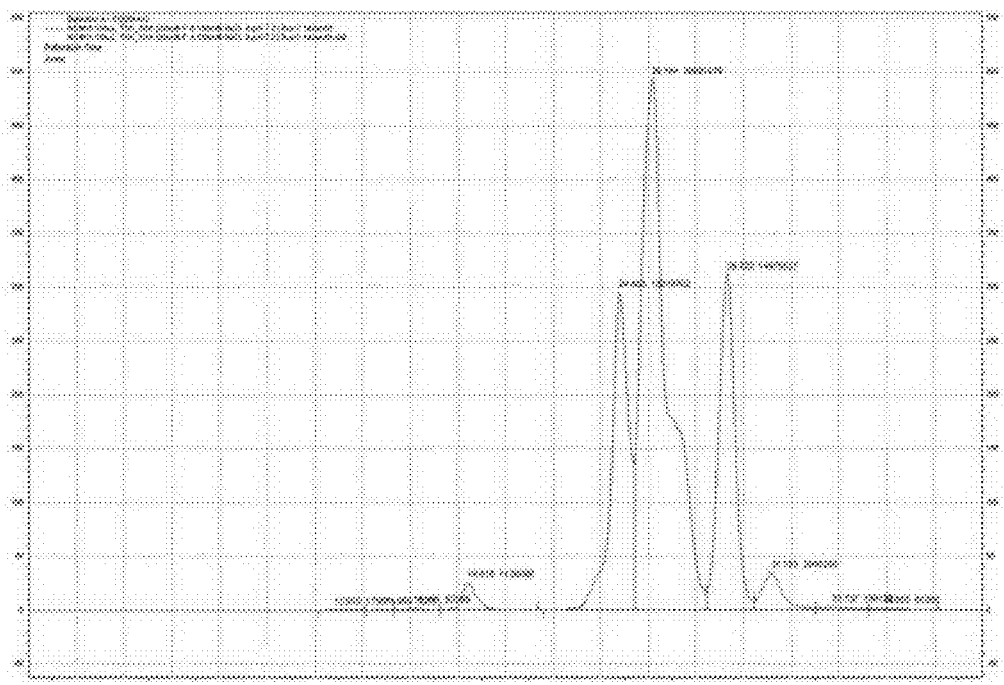

MESENCHYMAL STEM CELL PARTICLES

CROSS REFERENCE TO RELATED APPLICATIONS

This application is a continuation application of co-pending U.S. patent application Ser. No. 12/918,122 filed Aug. 18, 2010, which is a 35 U.S.C. § 371 National Phase Entry Application of International Application No. PCT/SG2009/000062 filed Feb. 21, 2009, which designates the U.S., and which claims benefit under 35 U.S.C. § 119(e) of U.S. Provisional No. 61/066,671 filed Feb. 22, 2008, the contents of each of which are incorporated herein by reference in their entireties.

FIELD

The present invention relates to the fields of development, cell biology, molecular biology and genetics. More particularly, the invention relates to a method of deriving mesenchymal stem cells from embryonic stem cells.

BACKGROUND

Stem cells, unlike differentiated cells, have the capacity to divide and either self-renew or differentiate into phenotypically and functionally different daughter cells (Keller, Genes Dev. 2005; 19:1129-1155; Wobus and Boheler, Physiol Rev. 2005; 85:635-678; Wiles, Methods in Enzymology. 1993; 225:900-918; Choi et al, Methods Mol Med. 2005; 105:359-368).

Mesenchymal stem cells (MSCs) are multipotent stem cells that have documented evidence of therapeutic efficacy in treating musculoskeletal injuries, improving cardiac function in cardiovascular disease and ameliorating the severity of GVHD (Le Blanc and Pittenger, 2005). Being lineage restricted, they have limited but robust potential to differentiate into mesenchymal cell types, e.g adipocytes, chondrocytes and osteocytes, and have negligible risk of teratoma formation. Host immune rejection of transplanted MSCs is routinely circumvented through autologous or allogeneic transplantation. MSCs can be isolated from several adult tissues including bone marrow (BM), adipose tissues (ad), cord blood and expanded ex vivo.

Mesenchymal stem cells have been used in clinical and preclinical applications to treat a wide range of diseases[1, 2] including musculoskeletal tissue bioengineering[3, 4] and heart disease[5, 6]. The therapeutic capacity of MSCs to treat a wide spectrum of diseases in clinical and preclinical applications to treat a wide range of diseases [A1,A2] e.g. GVHD [A1] in musculoskeletal tissue bioengineering [A3, A4] and heart disease [A5,A6] has been attributed to their potential to differentiate into many different reparative cell types.

However, availability of tissues for their isolation remains limiting and requires risky invasive procedures, and ex vivo expansion of MSCs while significant, is nonetheless finite. However, the efficiency of transplanted MSCs to differentiate into functional reparative cells in the injured tissues or organs, and in therapeutically relevant numbers have never been adequately documented or demonstrated.

Recent reports have suggested that some of these reparative effects may be mediated by paracrine factors secreted by the MSCs[7]. These factors are postulated to promote arteriogenesis through paracrine mechanisms[8], support the stem cell crypt in the intestine[9], protect against ischemic renal[10, 11], myocardial[12-15] and limb tissue injury[16]; support and maintain hematopoiesis[17], support formation of megakaryocyte and pro-platelet[18].

There is an unmet need for an "off-the-shelf" MSC-based therapeutic option, at affordable costs, with better quality control and consistency. This is a requisite for time-sensitive protection against injury such as reperfusion injury in patients with acute MI.

SUMMARY

According to a 1$^{st}$ aspect of the present invention, we provide a particle secreted by a mesenchymal stem cell and comprising at least one biological property of a mesenchymal stem cell.

The biological property may comprise a biological activity of a mesenchymal stem cell conditioned medium (MSC-CM). The biological activity may comprise cardioprotection. The particle may be capable of reducing infarct size.

Reduction of infarct may be assayed in a mouse or pig model of myocardial ischemia and reperfusion injury.

The particle may be capable of reducing oxidative stress. The reduction of oxidative stress may be assayed in an in vitro assay of hydrogen peroxide ($H_2O_2$)-induced cell death.

The particle comprise a vesicle. The particle may comprise an exosome.

The particle may contain at least 70% of proteins in an mesenchymal stem cell conditioned medium (MSC-CM). The proteins may be selected from the list shown in Table D1 or may be gene products of the genes shown in Table D2.

The particle may comprise a complex of molecular weight >100 kDa. The complex of molecular weight >100 kDa may comprise proteins of <100 kDa. The particle may comprise a complex of molecular weight >300 kDa. The complex of molecular weight >100 kDa may comprise proteins of <300 kDa.

The particle may comprise a complex of molecular weight >1000 kDa. The particle may have a size of between 2 nm and 200 nm. The particle may have a size of between 50 ηm and 150 nm. The particle may have a size of between 50 nm and 100 nm.

The size of the particle may be determined by filtration against a 0.4 μM filter and concentration against a membrane with a molecular weight cut-off of 10 kDa. The size of the particle may be determined by electron microscopy.

The particle may comprise a hydrodynamic radius of below 100 nm. It may comprise a hydrodynamic radius of between about 30 nm and about 70 nm. It may be between about 40 nm and about 60 nm, such as between about 45 nm and about 55 nm. The mesenchymal stem cell particle may comprise a hydrodynamic radius of about 50 nm. The hydrodynamic radius may be determined by laser diffraction or dynamic light scattering.

The particle may comprise a lipid selected from the group consisting of: phospholipid, phosphatidyl serine, phosphatidyl inositol, phosphatidyl choline, shingomyelin, ceramides, glycolipid, cerebroside, steroids, cholesterol. The cholesterol-phospholipid ratio may be greater than 0.3-0.4 (mol/mol). The particle may comprise a lipid raft.

The particle may be insoluble in non-ionic detergent, preferably Triton-X100. The particle may be such that proteins of the molecular weights specified substantially remain in the complexes of the molecular weights specified, when the particle is treated with a non-ionic detergent.

The particle may be sensitive to cyclodextrin, preferably 20 mM cyclodextrin. The particle may be such that treatment with cyclodextrin causes substantial dissolution of the complexes specified.

The particle may comprise ribonucleic acid (RNA). The particle may have an absorbance ratio of 1.9 (260:280 nm). The particle may comprise a surface antigen selected from the group consisting of: CD9, CD109 and thy-1.

There is provided, according to a $2^{nd}$ aspect of the present invention, a method of producing a particle according to any preceding claim, the method comprising isolating the particle from a mesenchymal stem cell conditioned medium (MSC-CM).

The method may comprise separating the particle from other components based on molecular weight, size, shape, composition or biological activity.

The weight may be selected from the weights set out above. The size may be selected from the sizes set out above. The composition may be selected from the compositions set out above. The biological activity may be selected from the biological activities set out above.

We provide, according to a $3^{rd}$ aspect of the present invention, a method of producing a particle according as described above. The method may comprise obtaining a mesenchymal stem cell conditioned medium (MSC-CM). It may comprise concentrating the mesenchymal stem cell conditioned medium. The mesenchymal stem cell conditioned medium may be concentrated by ultrafiltration over a >1000 kDa membrane. The method may comprise subjecting the concentrated mesenchymal stem cell conditioned medium to size exclusion chromatography. A TSK Guard column SWXL, 6×40 mm or a TSK gel G4000 SWXL, 7.8×300 mm column may be employed. The method may comprise selecting UV absorbant fractions, for example, at 220 nm, that exhibit dynamic light scattering. The dynamic light scattering may be detected by a quasi-elastic light scattering (QELS) detector. The method may comprise collecting fractions which elute with a retention time of 11-13 minutes, such as 12 minutes.

We provide, according to a $4^{th}$ aspect of the present invention, a pharmaceutical composition comprising a particle as described together with a pharmaceutically acceptable excipient, diluent or carrier.

As a fourth aspect of the present invention, there is provided such a particle or such a pharmaceutical composition for use in a method of treating a disease.

We provide, according to a $5^{th}$ aspect of the present invention, use of such a particle for the preparation of a pharmaceutical composition for the treatment of a disease.

The present invention, in a $6^{th}$ aspect, provides use of such a particle in a method of treatment of a disease in an individual.

The disease may be selected from the group consisting of: cardiac failure, bone marrow disease, skin disease, burns and degenerative diseases such as diabetes, Alzheimer's disease, Parkinson's disease and cancer.

The disease may be selected from the group consisting of: myocardial infarction, a cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterised by initial injury inducing inflammation and immune dysregulation leading to chronic tissue remodeling including fibrosis and loss of function, renal ischemic injury, cystic fibrosis, sinusitis and rhinitis or an orthopaedic disease.

The particle may be used to aid wound healing, scar reduction, bone formation, a bone graft or bone marrow transplantation in an individual.

The particle may be used (i) in the regulation of a pathway selected from any one or more of the following: cytoskeletal regulation by Rho GTPase, cell cycle, integrin signalling pathway, Inflammation mediated by chemokine & cytokine signaling pathway, FGF signaling pathway, EGF receptor signaling pathway, angiogenesis, plasminogen activating cascade, blood coagulation, glycolysis, ubiquitin proteasome pathway, de novo purine biosynthesis, TCA cycle, phenylalanine biosynthesis, heme biosynthesis; (ii) in the regulation of processes including any one or more of the following: cell structure and motility, cell structure, cell communication, cell motility, cell adhesion, endocytosis, mitosis, exocytosis, cytokinesis, cell cycle, immunity and defense, cytokine/chemokine mediated immunity, macrophage-mediated immunity, granulocyte-mediated immunity, ligand-mediated signaling, cytokine and chemokine mediated signaling pathway, signal transduction, extracellular matrix protein-mediated signaling, growth factor homeostasis, receptor protein tyrosine kinase signaling pathway, cell adhesion-mediated signaling, cell surface receptor mediated signal transduction, JAK-STAT cascade, antioxidation and free radical removal, homeostasis, stress response, blood clotting, developmental processes, mesoderm development, skeletal development, angiogenesis, muscle development, muscle contraction, protein metabolism and modification, proteolysis, protein folding, protein complex assembly, amino acid activation, intracellular protein traffic, other protein targeting and localization, amino acid metabolism, protein biosynthesis, protein disulfide-isomerase reaction, carbohydrate metabolism, glycolysis, pentose-phosphate shunt, other polysaccharide metabolism, purine metabolism, regulation of phosphate metabolism, vitamin metabolism, amino acid biosynthesis, pre-mRNA processing, translational regulation, mRNA splicing; or (iii) in the supply of functions including any one or more of the following: signaling molecule, chemokine, growth factor, cytokine, interleukin, other cytokine, extracellular matrix, extracellular matrix structural protein, other extracellular matrix, extracellular matrix glycoprotein, protease, metalloprotease, other proteases, protease inhibitor, metalloprotease inhibitor, serine protease inhibitor, oxidoreductase, dehydrogenase, peroxidase, chaperone, chaperonin, Hsp 70 family chaperone, other chaperones, synthetase, synthase and synthetase, select calcium binding protein, aminoacyl-tRNA synthetase, lyase, isomerase, other isomerase, ATP synthase, hydratase, transaminase, other lyase, other enzyme regulator, select regulatory molecule, actin binding cytoskeletal protein, cytoskeletal protein, non-motor actin binding protein, actin and actin related protein, annexin, tubulin, cell adhesion molecule, actin binding motor protein, intermediate filament, ribonucleoprotein, ribosomal protein, translation factor, other RNA-binding protein, histone, calmodulin related protein, vesicle coat protein.

In a $7^{th}$ aspect of the present invention, there is provided a delivery system for delivering a particle, comprising a source of particle together with a dispenser operable to deliver the particle to a target.

According to an $8^{th}$ aspect of the present invention, we provide use of such a delivery system in a method of delivering a particle to a target.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855; and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 7A shows comparison of protein components in filtrate vs protein components in the non-conditioned medium (NCM). Conditioned medium (CM), the filtrate after CM was filtered through membrane with a 100 kD MW cut-off (100 kD filtrate) and NCM was separated on a SDS-PAGE. The gel was stained with silver to visualize protein bands; FIG. 7B shows CM was filtered through a 100 kD MW cut-off membrane to produce a retentate to filtrate volume ratio of 4:1. The retentate, filtrate, and the different protein supplements in the chemically defined medium, namely insulin-transferin-selenoprotein, FGF2, EGF and PDGF AB were separated on a SDS-PAGE The retentate and filtrate was loaded in a volume ratio of 4:1

FIG. 13 shows Proteins found from MS/MS analysis that are common to exosomes from different cell types[44].

FIG. 17A shows CM was fractionated, FIGS. 17B-17C show CM was treated with lysis buffer before being fractionated on the sucrose gradient.

FIGS. 19A-19B show RNA was extracted from MSCs and MSC-CM. The purified RNA was denatured and separated on a glyoxal agarose gel and urea-PAGE, respectively. FIG. 19C shows Equal volume of CM was treated with PBS, cyclodextrin, lysis buffer or phospholipase A2. The untreated and treated CM were extracted for RNA. The RNA was separated on urea-PAGE. FIG. 19D shows RNA from CM was treated with RNAse III and the treated RNA was separated in parallel with untreated RNA on a urea-PAGE. RNA in the gels was visualized by staining with ethidium bromide.

FIG. 20A shows the relative RNA yield for each fraction in each sample was plotted against fraction number. The relative concentration was normalized to the highest RNA concentration in each gradient which was arbitrary set as 100%. FIG. 20B shows The RNA extracted from each fraction was separated on a urea-PAGE.

FIG. 22A shows 149 miRNA were detected in MSC and 63 were detected in the CM. Of these, 47 were expressed at similar levels in both MSCs and the CM. 16 were expressed at a detectable level in CM but not in MSC s while 47 were detected in MSCs but not in the CM. FIG. 22B shows Relative expression level of guide miRNA to its anti-guide miRNA based on hybridization signal on the microarray chip.

FIG. 23 shows HPLC fractionation of CM and NCM. CM and NCM were fractionated on a HPLC using BioSep S4000, 7.8 mm×30 cm column. The components in CM or NCM were eluted with 20 mM phosphate buffer with 150 mM of NaCl at pH 7.2. The elution mode was isocratic and the run time was 40 minutes. The eluent was monitored with an UV-visible detector set at 220 nm. The % area under each peak was integrated from the UV-visible detector.

DETAILED DESCRIPTION

Figure 1A:
FIGS. 1A-1E show Myocardial Infarct Size. Representative pictures of Evans blue (blue) and TTC (red) staining on hearts of pigs treated with non-CM (FIG. 1A), CM (FIG. 1B) or saline (FIG. 1C). Myocardial infarct size quantifications as a percentage of the left ventricle (LV) and the area at risk (AAR) are shown in FIG. 1D and FIG. 1E, respectively. Non-CM, n=9; CM, n=9; saline, n=8.
Figure 1B:
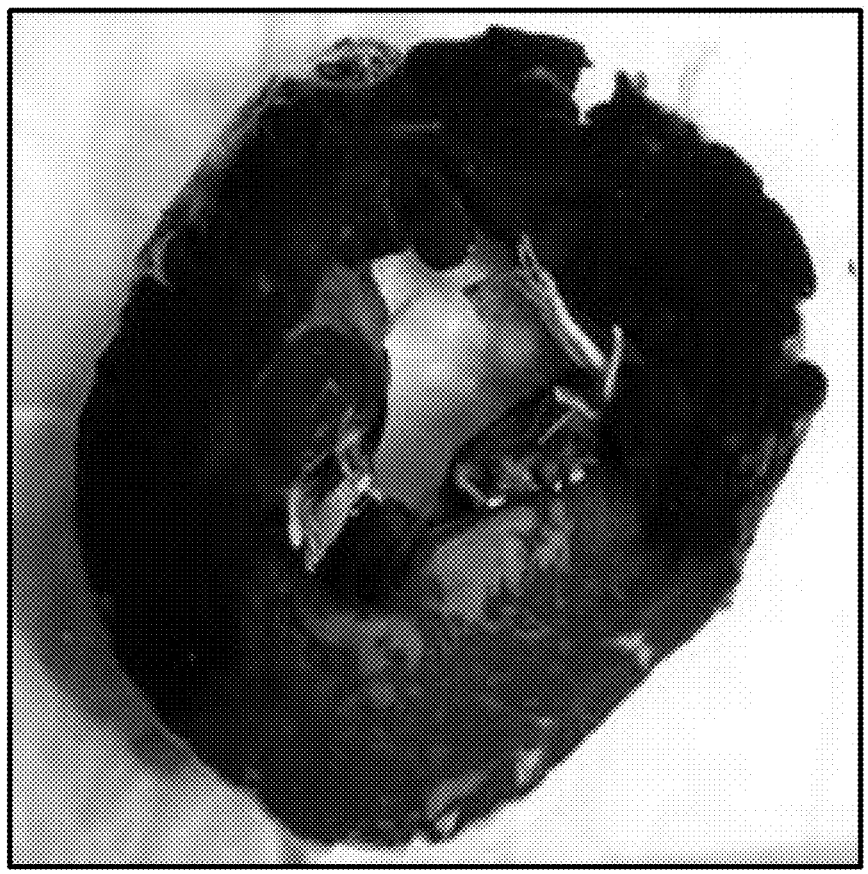
Figure 1C:
Figure 1D:
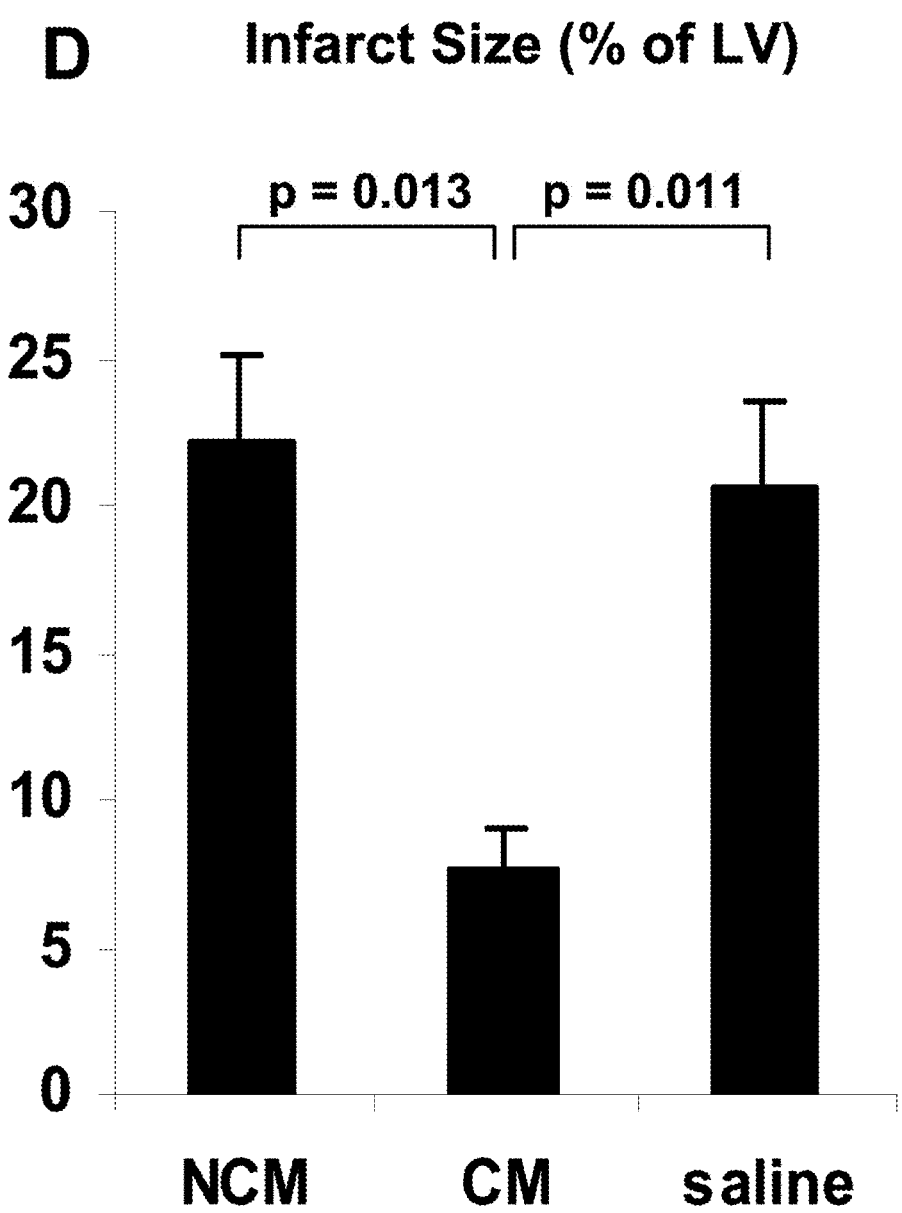
Figure 1E:
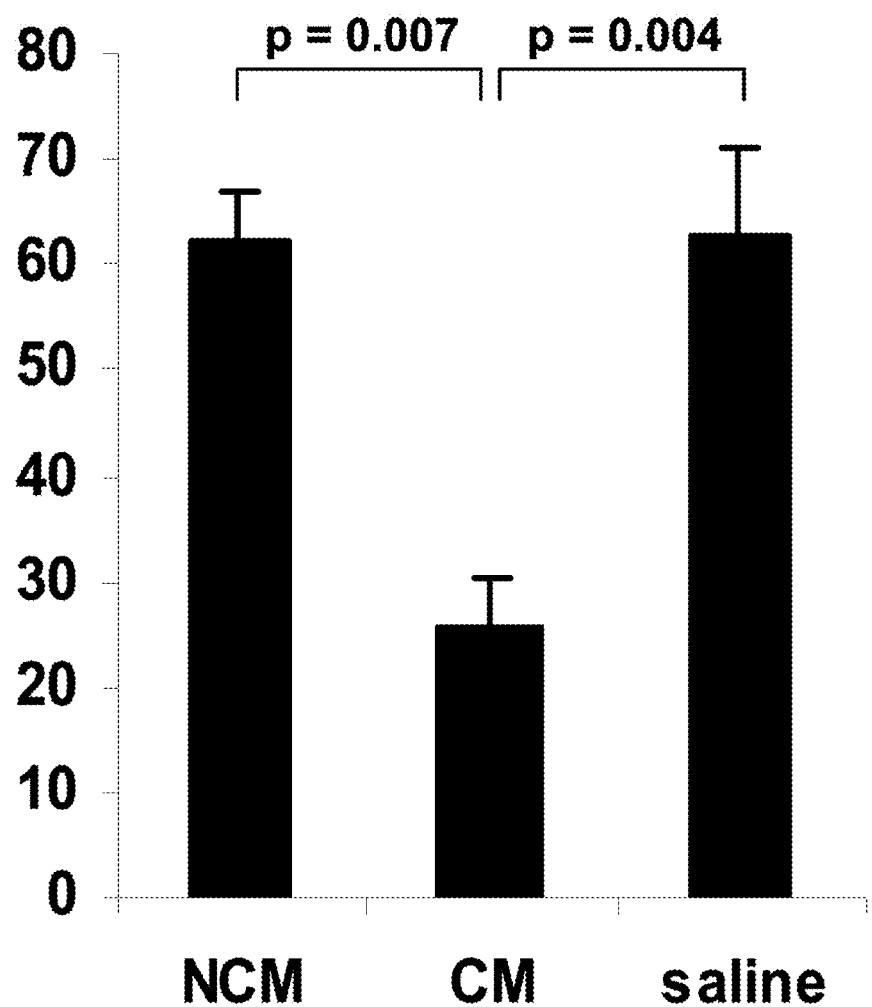

The present invention is based on the demonstration that human ESC-derived mesenchymal stem cells (MSCs) mediate cardioprotective effects through secreted large complexes of ~50-100 nm in diameter. Such complexes or particles may therefore be used for therapeutic means, including for cardioprotection, in place of the cells themselves.

The Examples describe proteomic analysis of these complexes, revealing the presence of exosome-associated proteins e.g. CD81, CD9 and Alix that also co-immunopreciptate, and of membrane and cytosolic proteins that exhibited detergent-sensitive proteolysis consistent with membrane-bound and membrane-encapsulated proteins respectively.

The Examples further demonstrate other properties of these particles or complexes. We show that proteins of such particles or complexes have MW-independent sedimentation densities of 1.016-1.215 g/ml that revert to MW-dependent densities upon treatment with a membrane lysis buffer. The secretion also contains RNAs (<300 nts) in cholesterol-rich lipid vesicles. HPLC fractionation and dynamic light scattering studies further indicate that the only detectable particles in the secretion within hydrodynamic radius (rh) range of 1-1000 nm had a rh of 45-55 nm.

These observations together with the presence of membrane lipids e.g. cholesterol sphingomyelin and phosphatidylcholine demonstrate that the cardioprotective complexes in the secretion are exosomes or secreted lipid vesicles.

These mesenchymal stem cell particles, complexes or exosomes may be used for a variety of purposes, such as treatment or prevention for cardiac or heart diseases such as ischaemia, cardiac inflammation or heart failure. They may also be used for repair following perfusion injury.

Particle

We describe a particle which is derivable from a mesenchymal stem cell (MSC).

The particle may be derivable from the MSC by any of several means, for example by secretion, budding or dispersal from the MSC. For example, the particle may be produced, exuded, emitted or shed from the MSC. Where the MSC is in cell culture, the particle may be secreted into the cell culture medium.

The particle may in particular comprise a vesicle. The particle may comprise an exosome. The particles described here may comprise any one or more of the properties of the exosomes described herein.

The particle may comprise vesicles or a flattened sphere limited by a lipid bilayer. The particles may comprise diameters of 40-100 nm. The particles may be formed by inward budding of the endosomal membrane. The particles may have a density of ~1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in mesenchymal stem cells or mesenchymal stem cell conditioned medium (MSC-CM), such as a protein characteristic or specific to the MSC or MSC-CM. They may comprise RNA, for example miRNA.

We provide a particle which comprises one or more genes or gene products found in MSCs or medium which is conditioned by culture of MSCs. The particle may comprise molecules secreted by the MSC. Such a particle, and combinations of any of the molecules comprised therein, including in particular proteins or polypeptides, may be used to supplement the activity of, or in place of, the MSCs or medium conditioned by the MSCs for the purpose of for example treating or preventing a disease.

The particle may comprise a cytosolic protein found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. In particular, the particle may comprise one or more tetraspanins. The particles may comprise mRNA and/or microRNA.

The term "particle" as used in this document may be taken to mean a discrete entity. The particle may be something that is isolatable from a mesenchymal stem cell (MSC) or mesenchymal stem cell conditioned medium (MSC-CM). The particle may be responsible for at least an activity of the MSC or MSC-CM. The particle may be responsible for, and carry out, substantially most or all of the functions of the MSC or MSC-CM. For example, the particle may be a substitute (or biological substitute) for the MSC or MSC-CM.

The particle may be used for any of the therapeutic purposes that the MSC or MSC-CM may be put to use.

The particle preferably has at least one property of a mesenchymal stem cell. The particle may have a biological property, such as a biological activity. The particle may have any of the biological activities of an MSC. The particle may for example have a therapeutic or restorative activity of an MSC.

The Examples show that media conditioned by MSCs (such as mesenchymal stem cell conditioned media or MSC-CM, as described below) comprise biological activities of MSC and are capable of substituting for the MSCs themselves. The biological property or biological activity of an MSC may therefore correspond to a biological property or activity of an mesenchymal stem cell conditioned medium. Accordingly, the particle may comprise one or more biological properties or activities of a mesenchymal stem cell conditioned medium (MSC-CM).

Mesenchymal Stem Cell Conditioned Medium (MSC-CM)

The conditioned cell culture medium such as a Mesenchymal Stem Cell Conditioned Medium (MSC-CM) may be obtained by culturing a mesenchymal stem cell (MSC), a descendent thereof or a cell line derived therefrom in a cell culture medium; and isolating the cell culture medium. The mesenchymal stem cell may be produced by a process comprising obtaining a cell by dispersing a embryonic stem (ES) cell colony. The cell, or a descendent thereof, may be propagated in the absence of co-culture in a serum free medium comprising FGF2.

Mesenchymal Stem Cell Particle

The particle may be produced or isolated in a number of ways. Such a method may comprise isolating the particle from a mesenchymal stem cell (MSC). Such a method may comprise isolating the particle from an mesenchymal stem cell conditioned medium (MSC-CM).

The particle may be isolated for example by being separated from non-associated components based on any property of the particle. For example, the particle may be isolated based on molecular weight, size, shape, composition or biological activity.

The conditioned medium may be filtered or concentrated or both during, prior to or subsequent to separation. For example, it may be filtered through a membrane, for example one with a size or molecular weight cut-off. It may be subject to tangential force filtration or ultrafiltration.

For example, filtration with a membrane of a suitable molecular weight or size cutoff, as described in the Assays for Molecular Weight elsewhere in this document, may be used.

The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the particle may be used to track its activity during fractionation of the mesenchymal stem cell conditioned medium (MSC-CM). As an example, light scattering, refractive index, dynamic light scattering or UV-visible detectors may be used to follow the particles. For example, a therapeutic activity such as cardioprotective activity may be used to track the activity during fractionation.

The following paragraphs provide a specific example of how a mesenchymal stem cell particle such as an exosome may be obtained.

A mesenchymal stem cell particle may be produced by culturing mesenchymal stem cells in a medium to condition it. The mesenchymal stem cells may comprise HuES9.E1 cells. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or -mercaptoethanol, or any combination thereof.

The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6×40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector.

Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of particles in this peak is about 45-55 nm. Such fractions comprise mesenchymal stem cell particles such as exosomes.

Particle Properties

The property of a mesenchymal stem cell may comprise a property of a medium conditioned by a mesenchymal stem cell (MSC-CM). Methods of producing such a mesenchymal stem cell conditioned medium are described elsewhere in this document and are illustrated in for example Example 1 below.

The property may comprise a biological property such as a biological activity. Examples of biological activities include cardioprotection, reduction of oxidative stress and reduction of infarct size.

Cardioprotection

The particle may have a property of mesenchymal stem cells and/or mesenchymal stem cell conditioned medium (MSC-CM) comprising cardioprotection The cardioprotection may comprise restoration or maintenance of cardiac function during ischemia and/or reperfusion.

Assay for Cardioprotection

Cardioprotection may for example be assayed using any one or more of the methods described in Examples 5, 10, 14 and 20.

Oxidative Stress

The particle may have a property of mesenchymal stem cells and/or mesenchymal stem cell conditioned medium (MSC-CM) comprising the ability to reduce oxidative stress (or cytoprotection).

Assay for Oxidative Stress

The reduction of oxidative stress may for example be assayed using an in vitro assay of hydrogen peroxide ($H_2O_2$)-induced cell death. In summary, hydrogen peroxide ($H_2O_2$)-mediated oxidative stress is induced in human leukemic CEM cells and cell viability is monitored by Trypan blue-exclusion. Human leukemic CEM cells are incubated with particle, conditioned medium or mesenchymal stem cell (with saline as a control) and treated with 50 μM $H_2O_2$ to induce oxidative stress. Cell viability is assessed using Trypan Blue exclusion at 12, 24, 36 and 48 hours after $H_2O_2$ treatment.

The reduction of oxidative stress may further be assayed using an in vivo assay of DNA oxidation. In vivo oxidative stress may also be assayed as follows. Pigs are treated with the particle, conditioned medium or mesenchymal stem cell (with saline as a control). Tissue sections of pig heart are obtained. Nuclear oxidative stress in tissue sections of treated and untreated pigs is quantified by 8-OHdG immunostaining for oxidized DNA. The tissue sections are assayed for intense nuclear staining indicative of DNA oxidation and oxidative stress.

Infarct Size

The particle may have a property of mesenchymal stem cells and/or mesenchymal stem cell conditioned medium (MSC-CM) comprising the ability to reduce infarct size.

Assay for Infarct Size

Infarct size may for example be assayed using any one or more of the methods described in Examples 6 and 13.

Particle Molecular Weight

The particle may have a molecular weight of greater than 100 kDa. It may have a molecular weight of greater than 500 kDa. For example, it may have a molecular weight of greater than 1000 kDa.

The molecular weight may be determined by various means. In principle, the molecular weight may be determined by size fractionation and filtration through a membrane with the relevant molecular weight cut-off. The particle size may then be determined by tracking segregation of component proteins with SDS-PAGE or by a biological assay.

Assay of Molecular Weight by SDS-PAGE

The particle may have a molecular weight of greater than 100 kDa. For example, the particle may be such that most proteins of the particle with less than 100 kDa molecular weight segregate into the greater than 100 kDa molecular weight retentate fraction, when subject to filtration. Similarly, when subjected to filtration with a membrane with a 500 kDa cut off, most proteins of the particle with less than 500 kDa molecular weight may segregate into the greater than 500 kDa molecular weight retentate fraction. This indicates that the particle may have a molecular weight of more than 500 kDa.

Assay of Molecular Weight by Biological Activity

The particle may have a molecular weight of more than 1000 kDa. For example, the particle may be such that when subject to filtration with a membrane with a molecular weight cutoff of 1000 kDa, the relevant biological activity substantially or predominantly remains in the retentate fraction. Alternatively or in addition, biological activity may be absent in the filtrate fraction. The biological activity may comprise any of the biological activities of the particle described elsewhere in this document.

Assay of Molecular Weight by Infarct Size

For example, the biological activity may comprise reduction of infarct size, as assayed in any suitable model of myocardia ischemia and reperfusion injury. For example, the biological activity may be assayed in a mouse or pig model, such as described in the Examples.

In summary, myocardial ischemia is induced by 30 minutes left coronary artery (LCA) occlusion by suture ligation and reperfusion is initiated by removal of suture. Mice are treated with liquid containing the particles (such as unfractionated MSC-CM), filtrate (such as <100 or 1,000 kD fraction), retentate (such as >1000 kD retentate) or saline intravenously via the tail vein, 5 minutes before reperfusion. 24 hours later, the hearts are excised. Before excision, the Area At Risk (AAR) is determined by religating the LCA and then perfusing Evans blue through the aorta.

AAR is defined as the area not stained by the dye and is expressed as a percentage of the left ventricular wall area. Infarct size is assessed 24 hours later using Evans blue and TTC. Where the relative infarct size is significantly reduced in animals treated with mesenchymal stem cell conditioned medium (MSC-CM) and the retentate (such as a >1000 kD) fraction when compared to saline, this indicates that the particle has a molecular weight which is higher than the relevant cutoff of the membrane (e.g., greater than 1000 kDa).

Particle Size

The particle may have a size of greater than 2 nm. The particle may have a size of greater than 5 nm, 10 nm, 20 nm, 30 nm, 40 nm or 50 nm. The particle may have a size of greater than 100 nm, such as greater than 150 nm. The particle may have a size of substantially 200 nm or greater.

The particle or particles may have a range of sizes, such as between 2 nm to 20 nm, 2 nm to 50 nm, 2 nm to 100 nm, 2 nm to 150 nm or 2 nm to 200 nm. The particle or particles may have a size between 20 nm to 50 nm, 20 nm to 100 nm, 20 nm to 150 nm or 20 nm to 200 nm. The particle or particles may have a size between 50 nm to 100 ηm, 50 ηm to 150 nm or 50 nm to 200 nm. The particle or particles may have a size between 100 nm to 150 nm or 100 nm to 200 nm. The particle or particles may have a size between 150 nm to 200 nm.

The size may be determined by various means. In principle, the size may be determined by size fractionation and filtration through a membrane with the relevant size cut-off. The particle size may then be determined by tracking segregation of component proteins with SDS-PAGE or by a biological assay.

The size may also be determined by electron microscopy, as described in Example 21.

The size may comprise a hydrodynamic radius. The hydrodynamic radius of the particle may be below 100 nm. It may be between about 30 nm and about 70 nm. The hydrodynamic radius may be between about 40 nm and about 60 nm, such as between about 45 nm and about 55 nm. The hydrodynamic radius may be about 50 nm.

The hydrodynamic radius of the particle may be determined by any suitable means, for example, laser diffraction or dynamic light scattering. An example of a dynamic light scattering method to determine hydrodynamic radius is set out in Example 33 below.

Composition

The particle may comprise one or more proteins secreted by a mesenchymal stem cell. The particle may comprise one or more proteins present in mesenchymal stem cell conditioned medium (MSC-CM).

For example, the particle may comprise 10% or more, 20% or more, 30% or more, 40% or more, 50% or more, 60% or more or 70% or more of these proteins. The particle may comprise substantially about 75% of these proteins. The proteins may be defined by reference to a list of proteins or gene products of a list of genes.

Proteins

The proteins may be selected from those set out in Table D1 below. Table D1 comprises the following proteins numbered 1 to 250, as well as the "proteins with unidentified functions", in the paragraphs below:

1. IPI00021428 Actin, alpha skeletal muscle; 2. IPI00414057 Actin alpha 1 skeletal muscle protein; 3. IPI00008603 Actin, aortic smooth muscle; 4. IPI00021439 Actin, cytoplasmic 1; 5. IPI00023006 Actin, alpha cardiac; 6. IPI00021440 Actin, cytoplasmic 2; 7. IPI00025416 Actin, gamma-enteric smooth muscle; 8. IPI00479925 agrin; 9. IPI00015102 CD 166 antigen precursor; 10. IPI00007423 Acidic leucine-rich nuclear phosphoprotein 32 family member B; 11. IPI00413331 36 kDa protein; 12. IPI00412577 34 kDa protein; 13. IPI00413506 33 kDa protein; 14. IPI00418169 Hypothetical protein DKFZp686P03159; 15. IPI00003815 Rho GDP-dissociation inhibitor 1; 16. IPI00004656 Beta-2-microglobulin precursor; 17. IPI00218042 Splice Isoform BMP1-5 of Bone morphogenetic protein 1 precursor; 18. IPI00009054 Splice Isoform BMP1-3 of Bone morphogenetic protein 1 precursor; 19. IPI00014021 Splice Isoform BMP1-1 of Bone morphogenetic protein 1 precursor; 20. IPI00218040 Splice Isoform BMP1-4 of Bone morphogenetic protein 1 precursor; 21. IPI00006980 Protein C14orf166; 22. IPI00296165 Complement C1r subcomponent precursor; 23. IPI00152540 OTTHUMP00000016748; 24. IPI00305064 Splice Isoform CD44 of CD44 antigen precursor; 25. IPI00297160 Hypothetical protein DKFZp451K1918; 26. IPI00293539 Splice Isoform 2 of Cadherin-11 precursor; 27. IPI00304227 Splice Isoform 1 of Cadherin-11 precursor; 28. IPI00386476 Cadherin 11, type 2, isoform 1 preproprotein; 29. IPI00024046 Cadherin-13 precursor;

30. IPI00290085 Neural-cadherin precursor; 31. IPI00029739 Splice Isoform 1 of Complement factor H precursor; 32. IPI00012011 Cofilin, non-muscle isoform; 33. IPI00007257 calsyntenin 1 isoform 2; 34. IPI00218539 Splice Isoform B of Collagen alpha-1(XI) chain precursor; 35. IPI00477350 Collagen, type XI, alpha 1; 36. IPI00329573 Splice Isoform Long of Collagen alpha-1(XII) chain precursor; 37. IPI00221384 Splice Isoform Short of Collagen alpha-1(XII) chain precursor; 38. IPI00400935 Collagen alpha-1(XVI) chain precursor; 39. IPI00297646 Collagen alpha-1(I) chain precursor; 40. IPI00164755 Prepro-alpha2(I) collagen precursor; 41. IPI00304962 Collagen alpha-2(I) chain precursor; 42. IPI00021033 Collagen alpha-1(III) chain precursor; 43. IPI00167087 COL3A1 protein; 44. IPI00021034 Collagen alpha-1(IV) chain precursor; 45. IPI00479324 alpha 2 type IV collagen preproprotein; 46. IPI00306322 Collagen alpha-2(IV) chain precursor; 47. IPI00303313 Collagen alpha-1(V) chain precursor; 48. IPI00477611 184 kDa protein; 49. IPI00293881 COL5A2 protein; 50. IPI00018279 Collagen alpha-3(V) chain precursor; 51. IPI00291136 Collagen alpha-1(VI) chain precursor; 52. IPI00304840 Splice Isoform 2C2 of Collagen alpha-2 (VI) chain precursor; 53. IPI00220613 Splice Isoform 2C2A of Collagen alpha-2(VI) chain precursor; 54. IPI00022200 alpha 3 type VI collagen isoform 1 precursor; 55. IPI00072918 alpha 3 type VI collagen isoform 4 precursor; 56. IPI00220701 Splice Isoform 2 of Collagen alpha-3(VI) chain precursor; 57. IPI00072917 alpha 3 type VI collagen isoform 3 precursor; 58. IPI00021828 Cystatin B; 59. IPI00007778 Di-N-acetylchitobiase precursor; 60. IPI00295741 Cathepsin B precursor;

61. IPI00299219 Protein CYR61 precursor; 62. IPI00514900 42 kDa protein; 63. IPI00333770 Similar to Dedicator of cytokinesis protein 10; 64. IPI00478332 Similar to Dedicator of cytokinesis protein 9; 65. IPI00000875 Elongation factor 1-gamma; 66. IPI00465248 Alpha-enolase; 67. IPI00013769 Alpha-enolase, lung specific; 68. IPI00216171 Gamma-enolase; 69. IPI00218803 Splice Isoform B of Fibulin-1 precursor; 70. IPI00296537 Splice Isoform C of Fibulin-1 precursor; 71. IPI00328113 Fibrillin-1 precursor; 72. IPI00019439 fibrillin 2 precursor; 73. IPI00385645 Splice Isoform 2 of Fibroblast growth factor 17 precursor; 74. IPI00216602 Splice Isoform 5 of Fibroblast growth factor receptor 2 precursor; 75. IPI00216604 Splice Isoform 8 of Fibroblast growth factor receptor 2 precursor; 76. IPI00034099 Hypothetical protein FLJ21918; 77. IPI00333541 Filamin-A; 78. IPI00302592 Filamin A, alpha; 79. IPI00339227 Hypothetical protein DKFZp686O1166; 80. IPI00414283 Fibronectin precursor (FN) (Cold-insoluble globulin) (CIG). Splice isoform 3; 81.

IPI00339225 Splice Isoform 5 of Fibronectin precursor; 82. IPI00339319 Splice Isoform 11 of Fibronectin precursor; 83. IPI00556632 Splice Isoform 12 of Fibronectin precursor; 84. IPI00411462 Hypothetical protein DKFZp686B18150; 85. IPI00029723 Follistatin-related protein 1 precursor; 86. IPI00005401 Polypeptide N-acetylgalactosaminyltransferase 5; 87. IPI00219025 Glutaredoxin-1; 88. IPI00171411 Golgi phosphoprotein 2; 89. IPI00026314 Gelsolin precursor;

90. IPI00219757 Glutathione S-transferase P; 91. IPI00027569 Heterogeneous nuclear ribonucleoprotein C-like 1; 92. IPI00003881 HNRPF protein; 93. IPI00442294 Splice Isoform 1 of Neurotrimin precursor; 94. IPI00003865 Splice Isoform 1 of Heat shock cognate 71 kDa protein; 95. IPI00037070 Splice Isoform 2 of Heat shock cognate 71 kDa protein; 96. IPI00220362 10 kDa heat shock protein, mitochondrial; 97. IPI00024284 Basement membrane-specific heparan sulfate proteoglycan core protein precursor; 98. IPI00297284 Insulin-like growth factor binding protein 2 precursor; 99. IPI00297284 Insulin-like growth factor binding protein 2 precursor; 100. IPI00029236 Insulin-like growth factor binding protein 5 precursor; 101. IPI00029236 Insulin-like growth factor binding protein 5 precursor; 102. IPI00029235 Insulin-like growth factor binding protein 6 precursor; 103. IPI00029235 Insulin-like growth factor binding protein 6 precursor; 104. IPI00016915 Insulin-like growth factor binding protein 7 precursor; 105. IPI00016915 Insulin-like growth factor binding protein 7 precursor; 106. IPI00328163 K-ALPHA-1 protein; 107. IPI00021396 Vascular endothelial growth factor receptor 2 precursor; 108. IPI00298281 Laminin gamma-1 chain precursor; 109. IPI00219219 Galectin-1; 110. IPI00023673 Galectin-3 binding protein precursor; 111. IPI00021405 Splice Isoform A of Lamin-A/C; 112. IPI00216953 Splice Isoform ADelta10 of Lamin-A/C; 113. IPI00180173 PREDICTED: similar to tropomyosin 4; 114. IPI00401614 PREDICTED: similar to FKSG30; 115. IPI00374397 PREDICTED: similar to tropomyosin 4; 116. IPI00374732 PREDICTED: similar to PPIA protein; 117. IPI00402104 PREDICTED: similar to peptidylprolyl isomerase A isoform 1; cyclophilin A; peptidyl-pro; 118. IPI00455415 PREDICTED: similar to Heterogeneous nuclear ribonucleoprotein C-like dJ845O24.4; 119. IPI00454722 PREDICTED: similar to Phosphatidylethanolamine-binding protein; 120. IPI00454852 PREDICTED: similar to Teratocarcinoma-derived growth factor 1;

121. IPI00002802 Protein-lysine 6-oxidase precursor; 122. IPI00410152 latent transforming growth factor beta binding protein 1 isoform LTBP-1L; 123. IPI00220249 Latent transforming growth factor beta-binding protein, isoform 1L precursor; 124. IPI00220249 Latent transforming growth factor beta-binding protein, isoform 1L precursor"; 125. IPI00410152 latent transforming growth factor beta binding protein 1 isoform LTBP-1L; 126. IPI00020986 Lumican precursor; 127. IPI00291006 Malate dehydrogenase, mitochondrial precursor; 128. IPI00005707 Macrophage mannose receptor 2 precursor; 129. IPI00020501 Myosin-11; 130. IPI00019502 Myosin-9; 131. IPI00604620 Nucleolin; 132. IPI00220740 Splice Isoform 2 of Nucleophosmin; 133. IPI00219446 Phosphatidylethanolamine-binding protein; 134. IPI00299738 Procollagen C-endopeptidase enhancer 1 precursor; 135. IPI00015902 Beta platelet-derived growth factor receptor precursor; 136. IPI00216691 Profilin-1; 137. IPI00169383 Phosphoglycerate kinase 1; 138. IPI00219568 Phosphoglycerate kinase, testis specific; 139. IPI00296180 Urokinase-type plasminogen activator precursor; 140. IPI00215943 Splice Isoform 3 of Plectin 1; 141. IPI00215942 Splice Isoform 2 of Plectin 1; 142. IPI00014898 Splice Isoform 1 of Plectin 1; 143. IPI00398777 plectin 1 isoform 8; 144. IPI00398776 plectin 1 isoform 7; 145. IPI00186711 plectin 1 isoform 6; 146. IPI00420096 plectin 1 isoform 3; 147. IPI00398779 plectin 1 isoform 11; 148. IPI00398778 plectin 1 isoform 10; 149. IPI00398002 plectin 1 isoform 1; 150. IPI00419585 Peptidyl-prolyl cis-trans isomerase A;

151. IPI00472718 peptidylprolyl isomerase A isoform 2; 152. IPI00000874 Peroxiredoxin-1; 153. IPI00024915 Peroxiredoxin-5, mitochondrial precursor; 154. IPI00375306 peroxiredoxin 5 precursor, isoform b; 155. IPI00012503 Splice Isoform Sap-mu-0 of Proactivator polypeptide precursor; 156. IPI00374179 proteasome activator subunit 1 isoform 2; 157. IPI00030154 Proteasome activator complex subunit 1; 158. IPI00168812 PTK7 protein tyrosine kinase 7 isoform d precursor; 159. IPI00419941 PTK7 protein tyrosine kinase 7 isoform a precursor; 160. IPI00003590 Quiescin Q6, isoform a; 161. IPI00015916 Bone-derived growth factor (Fragment); 162. IPI00015916 Bone-derived growth factor; 163. IPI00298289 Splice Isoform 2 of Reticulon-4; 164. IPI00021766 Splice Isoform 1 of Reticulon-4; 165. IPI00013895 Calgizzarin; 166. IPI00010402 Hypothetical protein; 167. IPI00218733 Superoxide dismutase; 168. IPI00014572 SPARC precursor; 169. IPI00005614 Splice Isoform Long of Spectrin beta chain, brain 1; 170. IPI00008780 Stanniocalcin-2 precursor; 171. IPI00301288 SEL-OB protein; 172. IPI00216138 Transgelin; 173. IPI00018219 Transforming growth factor-beta-induced protein ig-h3 precursor; 174. IPI00304865 transforming growth factor, beta receptor III"; 175. IPI00296099 Thrombospondin-1 precursor; 176. IPI00032292 Metalloproteinase inhibitor 1 precursor; 177. IPI00027166 Metalloproteinase inhibitor 2 precursor; 178. IPI00220828 Thymosin beta-4; 179. IPI00180240 thymosin-like 3;

180. IP100299633 OTTHUMP00000031270 (Fragment); 181. IP100465028 Triosephosphate isomerase 1 variant (Fragment); 182. IPI00451401 Splice Isoform 2 of Triosephosphate isomerase; 183. IPI00010779 Tropomyosin 4; 184. IPI00216975 Splice Isoform 2 of Tropomyosin alpha-4 chain; 185. IPI00180675 Tubulin alpha-3 chain; 186. IPI00218343 Tubulin alpha-6 chain; 187. IPI00216298 Thioredoxin; 188. IPI00472175 CDNA FLJ46672 fis, clone TRACH3009008, highly similar to Thioredoxin reductase; 189. IPI00450472 Ubiquitin-conjugating enzyme E2I; 190. IPI00018352 Ubiquitin carboxyl-terminal hydrolase isozyme L1; 191. IPI00010207 Ubiquitin-fold modifier 1 precursor; 192. IPI00260630 URB; 193. IPI00021263 14-3-3 protein zeta/delta; 194. IPI00642991 Hypothetical protein DKFZp686F10164; 195. IPI00470919 Hypothetical protein DKFZp686K08164; 196. IPI00719088 collagen, type VI, alpha 1 precursor; 197. IPI00654685 Similar to SPARC precursor; 198. IPI00641961 Collagen, type XII, alpha 1; 199. IPI00645849 Extracellular matrix protein 1; 200. IPI00554786 Thioredoxin reductase 1; 201. IPI00645018 Plasminogen activator, urokinase; 202. IPI00552339 Tissue inhibitor of metalloproteinase 1; 203. IPI00642997 Actin, cytoplasmic 2; 204. IPI00719778 Similar to Annexin A2; 205. IPI00647915 Transgelin 2; 206. IPI00552815 Collagen, type V, alpha 1; 207. IPI00552981 CDNA PSEC0266 fis, clone NT2RP3003649, highly similar to Homo sapiens fibulin-1D mRNA; 208. IPI00180776 29 kDa protein; 209. IPI00552416 Filamin A, alpha;

210. IPI00640698 Actin, gamma-enteric smooth muscle; 211. IPI00514530 Actin, alpha 1, skeletal muscle; 212. IPI00556442 Insulin-like growth factor binding protein 2 variant (Fragment); 213. IPI00513782 Gelsolin; 214. IPI00478731 29 kDa protein; 215. IPI00396479 24 kDa protein; 216. IPI00334627 39 kDa protein; 217. IPI00555762 PTK7 protein tyrosine kinase 7 isoform a variant (Fragment); 218. IPI00658202 97 kDa protein; 219. IPI00006273 CYR61 protein; 220. IPI00719405 TMSL6 protein; 221. IPI00658096 Thymosin beta-4; 222. IPI00376163 5 kDa protein; 223. IPI00556217 Fibrillin 1 variant (Fragment); 224. IPI00514817 Similar to Lamin A/C; 225. IPI00644087 Progerin; 226. IPI00655812 Rhabdomyosarcoma antigen MU-RMS-40.12; 227. IPI00604517 Similar to Nucleolin; 228. IPI00444262 CDNA FI145706 fis, clone FEBRA2028457, highly similar to Nucleolin; 229. IPI00412473 Protein; 230. IPI00414489 Protein; 231. IPI00411463 Protein; 232. IPI00556415 Transgelin variant (Fragment); 233. IPI00718825 Calmodulin; 234. IPI00478156 17 kDa protein; 235. IPI00386621 CALM3 protein; 236. IPI00647001 Acidic; 237. IPI00642650 Similar to Stanniocalcin 2 precursor; 238. IPI00641471 Collagen-like protein; 239. IPI00514669 SH3 domain binding glutamic acid-rich protein like 3; 240. IPI00719422 Triosephosphate isomerase (Fragment); 241. IPI00003734 Putative S100 calcium-binding protein H_NH0456N16.1; 242. IPI00029574 11 kDa protein; 243. IPI00641047 Gelsolin; 244. IPI00647556 Gelsolin; 245. IPI00654821 hypothetical protein L0054845 isoform 1; 246. IPI00647572 Dickkopf related protein-3 precursor; 247. IPI00639879 Similar to Cytokinesis protein sepA; 248. IPI00657746 Similar to Dedicator of cytokinesis protein 8; 249. IPI00555993 Vascular endothelial growth factor receptor 3 variant; 250. IPI00552545 Dedicator of cytokinesis protein 8.

Proteins with unidentified functions: IPI00642991 Hypothetical protein DKFZp686F10164; IPI00470919 Hypothetical protein DKFZp686K08164; IPI00654685 Similar to SPARC precursor; IPI00719778 Similar to Annexin A2; IPI00552981 CDNA PSEC0266 fis, clone NT2RP3003649, highly similar to Homo sapiens fibulin-1D mRNA; IPI00180776 29 kDa protein; IPI00478731 29 kDa protein; IPI00396479 24 kDa protein; IPI00334627 39 kDa protein; IPI00658202 97 kDa protein; IPI00376163 5 kDa protein; IPI00514817 Similar to Lamin A/C; IPI00644087 Progerin; IPI00655812 Rhabdomyosarcoma antigen MU-RMS-40.12; IPI00604517 Similar to Nucleolin; IPI00444262 CDNA FLJ45706 fis, clone FEBRA2028457, highly similar to Nucleolin; IPI00412473 Protein; IPI00414489 Protein; IPI00411463 Protein; IPI00478156 17 kDa protein; IPI00386621 CALM3 protein; IPI00647001 Acidic; IPI00642650 Similar to Stanniocalcin 2 precursor; IPI00641471 Collagen-like protein; IPI00514669 SH3 domain binding glutamic acid-rich protein like 3; IPI00003734 Putative S100 calcium-binding protein H_NH0456N16.1; IPI00029574 11 kDa protein; IPI00654821 hypothetical protein L0054845 isoform 1; IPI00647572 Dickkopf related protein-3 precursor; IPI00639879 Similar to Cytokinesis protein sepA; IPI00657746 Similar to Dedicator of cytokinesis protein 8; IPI00555993 Vascular endothelial growth factor receptor 3 variant.

Gene Products

The proteins may be selected from the gene products of the genes set out in Table D2 below. Table D2 comprises the following genes in the paragraphs below:

ACTA1; COL5A2; HSPA8; PSAP; ACTA2; COL5A3; HSPE1; PSME1; ACTB; COL6A1; HSPG2; PTK7; ACTC; COL6A2; IGFBP2; QSCN6; ACTG1; COL6A3; IGFBP5; RTN4; ACTG2; CSTB; IGFBP6; S100A11; AGRN; CTBS; IGFBP7; SH3BGRL3; ALCAM; CTSB; K-ALPHA-1; SOD1; ANP32B; CYR61; KDR; SPARC; ANXA2; DOCK10; LAMC1; SPTBN1; ARHGDIA; DOCK8; LGALS1; STC2; B2M; ECM1; LGALS3BP; SVEP1; BMP1; EEF1G; LMNA; TAGLN; C14orf166; ENOL; LOX; TAGLN2; C1R; ENO1B; LTBP1; TGFBI; CALM1; ENO2; LUM; TGFBR3; CD109; FBLN1; MDH2; THBS1; CD44; FBN1; MRC2; TIMP1; CDH11; FBN2; MYH11; TIMP2; CDH13; FGF17; MYH9; TMSB4X; CDH2; FGFR2; NCL; TMSL3; CFH/HF1; FI121918; NPM1; TMSL6; CFL1; FLNA; PBP; TPI1; CLSTN1; FN1; PCOLCE; TPM4; COL11A1; FSTL1; PDGFRB; TUBA3; COL12A1; GALNT5; PFN1; TUBA6; COL16A1; GLRX; PGK1; TXN; COL1A1; GOLPH2; PGK2; TXNRD1; COL1A2; GSN; PLAU; UBE2I; COL3A1; GSTP1; PLEC1; UCHL1; COL4A1; HNRPCL1; PPIA; UFM1; COL4A2; HNRPF; PRDX1; URB; COL5A1; HNT; PRDX5; YWHAZ.

201 Genes in 58 Biological Processes

The particle may additionally, or alternatively, comprise any of the gene products of the 201 genes listed below in Table D3. These genes are characterised according to a biological process the gene is involved in.

Accordingly, the particle may be employed to affect, control or regulate any of these 58 biological processes.

TABLE D3

Listing of 201 Genes in each of the 58 Biological Processes (Genes of Mesenchymal Stem Cell Conditioned Medium (MSC-CM))

| | Alcohol Metabolism |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |
| | Angiogenesis |
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |
| | Biomineral Formation |
| GI_27262662-A CDH11 | cadherin 11, type 2, OB-cadherin (osteoblast) |
| GI_5902810-A BMP1 | bone morphogenetic protein 1 |
| GI_4507170-S SPARC | secreted protein, acidic, cysteine-rich (osteonectin) |

TABLE D3-continued

Listing of 201 Genes in each of the 58 Biological Processes (Genes of Mesenchymal Stem Cell Conditioned Medium (MSC-CM))

Blood Vessel Development

| | | |
|---|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Blood Vessel Morphogenesis

| | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Bone Remodeling

| | |
|---|---|
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |

Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Carbohydrate Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Cellular Macromolecule Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Chemotaxis

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |

TABLE D3-continued

Listing of 201 Genes in each of the 58 Biological Processes (Genes of Mesenchymal Stem Cell Conditioned Medium (MSC-CM))

| | | |
|---|---|---|
| GI_22538399-S CCL11 | chemokine (C-C motif) ligand 11 | |
| GI_5453576-S CXCL13 | chemokine (C—X—C motif) ligand 13 (B-cell chemoattractant) | |
| GI_22538815-S CCL8 | chemokine (C-C motif) ligand 8 | |
| GI_34222286-S CYR61 | cysteine-rich, angiogenic inducer, 61 | |
| GI_4506832-S CCL1 | chemokine (C-C motif) ligand 1 | |
| GI_28610153-S IL8 | interleukin 8 | |
| GI_22538800-S CCL16 | chemokine (C-C motif) ligand 16 | |
| GI_14790145-S CXCL11 | chemokine (C—X—C motif) ligand 11 | |
| GI_22165426-S CCL24 | chemokine (C-C motif) ligand 24 | |
| GI_22538813-S CCL5 | chemokine (C-C motif) ligand 5 | |
| GI_13435401-S CCL7 | chemokine (C-C motif) ligand 7 | |
| GI_4505862-S PLAU | plasminogen activator, urokinase | |
| GI_4504152-S CXCL1 | chemokine (C—X—C motif) ligand 1 (melanoma growth stimulating activity, alpha) | |
| GI_27894329-S IL1A | interleukin 1, alpha | |
| GI_22547151-S CCL26 | chemokine (C-C motif) ligand 26 | |
| GI_4506852-S XCL1 | chemokine (C motif) ligand 1 | |

Defense Response

| | |
|---|---|
| GI_27894305-S IL1B | interleukin 1, beta |
| GI_27894329-S IL1A | interleukin 1, alpha |

Development

| | |
|---|---|
| GI_42716312-S ANG | angiogenin, ribonuclease, RNase A family, 5 |
| GI_5902810-A BMP1 | bone morphogenetic protein 1 |
| GI_27262662-A CDH11 | cadherin 11, type 2, OB-cadherin (osteoblast) |
| GI_27262662-A CSF1 | colony stimulating factor 1 (macrophage) |
| GI_27437029-S CSF2 | colony stimulating factor 2 (granulocyte-macrophage) |
| GI_27437048-A CSF3 | colony stimulating factor 3 (granulocyte) |
| GI_34222286-S CYR61 | cysteine-rich, angiogenic inducer, 61 |
| GI_24430140-S FBN1 | fibrillin 1 (Marfan syndrome) |
| GI_4755135-S FBN2 | fibrillin 2 (congenital contractural arachnodactyly) |
| GI_10337586-S FGF6 | fibroblast growth factor 6 |
| GI_24430216-S IL10 | interleukin 10 |
| GI_28610153-S IL8 | interleukin 8 |
| GI_11321596-S KDR | kinase insert domain receptor (a type III receptor tyrosine kinase) |
| GI_4580419-A KITLG | KIT ligand |
| GI_6006018-S LIF | leukemia inhibitory factor (cholinergic differentiation factor) |
| GI_7262388-S PCOLCE | procollagen C-endopeptidase enhancer |
| GI_4507170-S SPARC | secreted protein, acidic, cysteine-rich (osteonectin) |
| GI_10863872-S TGFB1 | transforming growth factor, beta 1 (Camurati-Engelmann disease) |
| GI_4507470-S TGFBR3 | transforming growth factor, beta receptor III (betaglycan, 300 kDa) |
| GI_40317625-S THBS1 | thrombospondin 1 |
| GI_40805871-S THPO | thrombopoietin (myeloproliferative leukemia virus oncogene ligand, megakaryocyte growth and development factor) |
| GI_4507508-S TIMP1 | TIMP metallopeptidase inhibitor 1 |
| GI_30172563-S VEGF | vascular endothelial growth factor |

Energy Derivation by Oxidation of Organic Compounds

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Exocytosis

| | |
|---|---|
| GI_22538815-S CCL8 | chemokine (C-C motif) ligand 8 |
| GI_22538813-S CCL5 | chemokine (C-C motif) ligand 5 |

Fever

| | |
|---|---|
| GI_27894305-S IL1B | interleukin 1, beta |
| GI_27894329-S IL1A | interleukin 1, alpha |

Generation of Precursor Metabolites and Energy

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Glucose Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |

TABLE D3-continued

Listing of 201 Genes in each of the 58 Biological Processes (Genes of Mesenchymal Stem Cell Conditioned Medium (MSC-CM))

| | | |
|---|---|---|
| GI_21735620-S MDH2 | malate dehydrogenase 2, NAD (mitochondrial) | |
| GI_26024330-S TPI1 | triosephosphate isomerase 1 | |

Glucose Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Glycolysis

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Heat Generation

| | |
|---|---|
| GI_27894305-S IL1B | interleukin 1, beta |
| GI_27894329-S IL1A | interleukin 1, alpha |

Hemopoiesis

| | |
|---|---|
| GI_27262662-A CSF1 | colony stimulating factor 1 (macrophage) |
| GI_4580419-A KITLG | KIT ligand |
| GI_24430216-S IL10 | interleukin 10 |

Hemopoietic or Lymphoid Organ Development

| | |
|---|---|
| GI_27262662-A CSF1 | colony stimulating factor 1 (macrophage) |
| GI_4580419-A KITLG | KIT ligand |
| GI_24430216-S IL10 | interleukin 10 |

Hexose Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Hexose Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Immune Response

| | |
|---|---|
| GI_27894305-S IL1B | interleukin 1, beta |
| GI_27894329-S IL1A | interleukin 1, alpha |

Inflammatory Response

| | |
|---|---|
| GI_27894305-S IL1B | interleukin 1, beta |
| GI_27894329-S IL1A | interleukin 1, alpha |

Macromolecule Metabolism

| | |
|---|---|
| GI_5902810-A BMP1 | bone morphogenetic protein 1 |
| GI_31542249-S C1R | complement component 1, r subcomponent |
| GI_22538429-A CTSB | cathepsin B |
| GI_16507965-S ENO1 | enolase 1, (alpha) |
| GI_16507966-S ENO2 | enolase 2 (gamma, neuronal) |
| GI_33859834-S HGF | hepatocyte growth factor (hepapoietin A; scatter factor) |
| GI_21735620-S MDH2 | malate dehydrogenase 2, NAD (mitochondrial) |
| GI_13027798-S MMP1 | matrix metallopeptidase 1 (interstitial collagenase) |
| GI_4505204-S MMP10 | matrix metallopeptidase 10 (stromelysin 2) |
| GI_13027796-S MMP13 | matrix metallopeptidase 13 (collagenase 3) |
| GI_13027803-S MMP3 | matrix metallopeptidase 3 (stromelysin 1, progelatinase) |
| GI_4826835-S MMP9 | matrix metallopeptidase 9 (gelatinase B, 92 kDa gelatinase, 92 kDa type IV collagenase) |
| GI_22095338-S PGK1 | phosphoglycerate kinase 1 |
| GI_31543396-S PGK2 | phosphoglycerate kinase 2 |
| GI_4505862-S PLAU | plasminogen activator, urokinase |
| GI_26024330-S TPI1 | triosephosphate isomerase 1 |

TABLE D3-continued

Listing of 201 Genes in each of the 58 Biological Processes (Genes of
Mesenchymal Stem Cell Conditioned Medium (MSC-CM))

Macromolecule Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Main Pathways of Carbohydrate Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Monosaccharide Catabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Monosaccharide Metabolism

| | |
|---|---|
| GI_16507966-S ENO2 | enolase 2 (gamma, neuronal) |
| GI_16507965-S ENO1 | enolase 1, (alpha) |
| GI_22095338-S PGK1 | phosphoglycerate kinase 1 |
| GI_31543396-S PGK2 | phosphoglycerate kinase 2 |
| GI_21735620-S MDH2 | malate dehydrogenase 2, NAD (mitochondrial) |
| GI_26024330-S TPI1 | triosephosphate isomerase 1 |

Organ Development

| | |
|---|---|
| GI_27262662-A CSF1 | colony stimulating factor 1 (macrophage) |
| GI_27262662-A CDH11 | cadherin 11, type 2, OB-cadherin (osteoblast) |
| GI_4580419-A KITLG | KIT ligand |
| GI_5902810-A BMP1 | bone morphogenetic protein 1 |
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_4507170-S SPARC | secreted protein, acidic, cysteine-rich (osteonectin) |
| GI_42716312-S ANG | angiogenin, ribonuclease, RNase A family, 5 |
| GI_24430216-S IL10 | interleukin 10 |
| GI_10337586-S FGF6 | fibroblast growth factor 6 |

Organ Morphogenesis

| | |
|---|---|
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

Ossification

| | |
|---|---|
| GI_27262662-A CDH11 | cadherin 11, type 2, OB-cadherin (osteoblast) |
| GI_5902810-A BMP1 | bone morphogenetic protein 1 |
| GI_4507170-S SPARC | secreted protein, acidic, cysteine-rich (osteonectin) |

Phosphate Metabolism

| | |
|---|---|
| GI_22095338-S PGK1 | phosphoglycerate kinase 1 |
| GI_31543396-S PGK2 | phosphoglycerate kinase 2 |

Phosphorus Metabolism

| | |
|---|---|
| GI_22095338-S PGK1 | phosphoglycerate kinase 1 |
| GI_31543396-S PGK2 | phosphoglycerate kinase 2 |

Response to Abiotic Stimulus

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |

TABLE D3-continued

Listing of 201 Genes in each of the 58 Biological Processes (Genes of
Mesenchymal Stem Cell Conditioned Medium (MSC-CM))

| | |
|---|---|
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Response to Biotic Stimulus

| | |
|---|---|
| GI_27894305-S IL1B | interleukin 1, beta |
| GI_27894329-S IL1A | interleukin 1, alpha |

Response to Chemical Stimulus

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Response to External Biotic Stimulus

| | |
|---|---|
| GI_27894305-S IL1B | interleukin 1, beta |
| GI_27894329-S IL1A | interleukin 1, alpha |

Response to External Stimulus

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_27894305-S IL1B | interleukin 1, beta |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

TABLE D3-continued

Listing of 201 Genes in each of the 58 Biological Processes (Genes of Mesenchymal Stem Cell Conditioned Medium (MSC-CM))

Response to Pest, Pathogen or Parasite

| | |
|---|---|
| GI_27894305-S IL1B | interleukin 1, beta |
| GI_27894329-S IL1A | interleukin 1, alpha |

Response to Stimulus

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_27894305-S IL1B | interleukin 1, beta |
| GI_13435401-S CCL7 | chemokine (C-C motif) ligand 7 |
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |

Response to Stress

| | |
|---|---|
| GI_27894305-S IL1B | interleukin 1, beta |
| GI_4505862-S PLAU | plasminogen activator, urokinase |
| GI_27894329-S IL1A | interleukin 1, alpha |

Response to Wounding

| | |
|---|---|
| GI_27894305-S IL1B | interleukin 1, beta |
| GI_4505862-S PLAU | plasminogen activator, urokinase |
| GI_27894329-S IL1A | interleukin 1, alpha |

Secretion

| | |
|---|---|
| GI_22538815-S CCL8 | chemokine (C-C motif) ligand 8 |
| GI_22538813-S CCL5 | chemokine (C-C motif) ligand 5 |

Secretory Pathway

| | |
|---|---|
| GI_22538815-S CCL8 | chemokine (C-C motif) ligand 8 |
| GI_22538813-S CCL5 | chemokine (C-C motif) ligand 5 |

Skeletal Development

| | |
|---|---|
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |

Taxis

| | |
|---|---|
| GI_27262654-A IL16 | interleukin 16 (lymphocyte chemoattractant factor) |
| GI_22538807-A CCL23 | chemokine (C-C motif) ligand 23 |
| GI_34335180-A CCL15 | chemokine (C-C motif) ligand 15 |
| GI_40316922-I CXCL12 | chemokine (C—X—C motif) ligand 12 (stromal cell-derived factor 1) |
| GI_41872613-S CXCL5 | chemokine (C—X—C motif) ligand 5 |
| GI_22538812-S CCL2 | chemokine (C-C motif) ligand 2 |
| GI_4504098-S CXCR3 | chemokine (C—X—C motif) receptor 3 |
| GI_22538399-S CCL11 | chemokine (C-C motif) ligand 11 |
| GI_5453576-S CXCL13 | chemokine (C—X—C motif) ligand 13 (B-cell chemoattractant) |
| GI_22538815-S CCL8 | chemokine (C-C motif) ligand 8 |
| GI_34222286-S CYR61 | cysteine-rich, angiogenic inducer, 61 |
| GI_4506832-S CCL1 | chemokine (C-C motif) ligand 1 |
| GI_28610153-S IL8 | interleukin 8 |
| GI_22538800-S CCL16 | chemokine (C-C motif) ligand 16 |
| GI_14790145-S CXCL11 | chemokine (C—X—C motif) ligand 11 |
| GI_22165426-S CCL24 | chemokine (C-C motif) ligand 24 |
| GI_22538813-S CCL5 | chemokine (C-C motif) ligand 5 |
| GI_13435401-S CCL7 | chemokine (C-C motif) ligand 7 |

TABLE D3-continued

Listing of 201 Genes in each of the 58 Biological Processes (Genes of Mesenchymal Stem Cell Conditioned Medium (MSC-CM))

| | |
|---|---|
| GI_4505862-S PLAU | plasminogen activator, urokinase |
| GI_4504152-S CXCL1 | chemokine (C—X—C motif) ligand 1 (melanoma growth stimulating activity, alpha) |
| GI_27894329-S IL1A | interleukin 1, alpha |
| GI_22547151-S CCL26 | chemokine (C-C motif) ligand 26 |
| GI_4506852-S XCL1 | chemokine (C motif) ligand 1 |
| | Thermoregulation |
| GI_27894305-S IL1B | interleukin 1, beta |
| GI_27894329-S IL1A | interleukin 1, alpha |
| | Tissue Development |
| GI_27262662-A CDH11 | cadherin 11, type 2, OB-cadherin (osteoblast) |
| GI_5902810-A BMP1 BMP1 | bone morphogenetic protein 1 |
| GI_4507170-S SPARC | secreted protein, acidic, cysteine-rich (osteonectin) |
| | Vasulogenesis |
| GI_30172563-S VEGF | vascular endothelial growth factor |
| | Vasculature Development |
| GI_11321596-S KDR | kinase insert domain receptor (a type III receptor tyrosine kinase) |
| GI_30172563-S VEGF | vascular endothelial growth factor |
| GI_28610153-S IL8 | interleukin 8 |
| GI_42716312-S ANG | angiogenin, ribonuclease, RNase A family, 5 |
| GI_10337586-S FGF6 | fibroblast growth factor 6 |

201 Genes in 30 Pathways

The particle may additionally, or alternatively, comprise any of the gene products of the 201 genes listed below in Table D4. These genes are characterised according to a pathway the gene is involved in.

Accordingly, the particle may be employed to affect, control or regulate any of these 30 pathways.

TABLE D4

Listing of 201 Genes in Each of the 30 Pathways (Genes of Mesenchymal Stem Cell Conditioned Medium (MSC-CM))

| | |
|---|---|
| Antigen processing and presentation - *Homo sapiens* (human) | |
| GI_22538429-A CTSB | cathepsin B |
| GI_37704380-S B2M | beta-2-microglobulin |
| GI_24234685-A HSPA8 | heat shock 70 kDa protein 8 |
| GI_30581139-A PSME1 | proteasome (prosome, macropain) activator subunit 1 (PA28 alpha) |
| Apoptosis - *Homo sapiens* (human) | |
| GI_41281560-S CLSTN1 | calsyntenin 1 |
| GI_28416914-S IL3 | interleukin 3 (colony-stimulating factor, multiple) |
| GI_27894329-S IL1A | interleukin 1, alpha |
| GI_27894305-S IL1B | interleukin 1, beta |
| GI_25952110-S TNF | tumor necrosis factor (TNF superfamily, member 2) |
| Carbon fixation - *Homo sapiens* (human) | |
| GI_21735620-S MDH2 | malate dehydrogenase 2, NAD (mitochondrial) |
| GI_26024330-S TPI1 | triosephosphate isomerase 1 |
| GI_22095338-S PGK1 | phosphoglycerate kinase 1 |
| GI_31543396-S PGK2 | phosphoglycerate kinase 2 |
| Cell Communication - *Homo sapiens* (human) | |
| GI_27436944-A LMNA | lamin A/C |
| GI_5016088-S ACTB | actin, beta |
| GI_10938011-S ACTC | actin, alpha, cardiac muscle |
| GI_11038618-S ACTG1 | actin, gamma 1 |
| GI_14719826-S COL1A1 | collagen, type I, alpha 1 |
| GI_21536289-S COL1A2 | collagen, type I, alpha 2 |
| GI_15149480-S COL3A1 | collagen, type III, alpha 1 (Ehlers-Danlos syndrome type IV, autosomal dominant) |
| GI_45580690-S COL4A1 | collagen, type IV, alpha 1 |
| GI_17986276-S COL4A2 | collagen, type IV, alpha 2 |
| GI_16554578-S COL5A1 | collagen, type V, alpha 1 |
| GI_16554580-S COL5A2 | collagen, type V, alpha 2 |

TABLE D4-continued

Listing of 201 Genes in Each of the 30 Pathways (Genes of Mesenchymal Stem Cell Conditioned Medium (MSC-CM))

| Gene ID | Symbol | Description |
|---|---|---|
| GI_15011912-S | COL6A1 | collagen, type VI, alpha 1 |
| GI_17402876-A | COL6A2 | collagen, type VI, alpha 2 |
| GI_17149810-A | COL6A3 | collagen, type VI, alpha 3 |
| GI_18375521-A | COL11A1 | collagen, type XI, alpha 1 |
| GI_16933543-A | FN1 | fibronectin 1 |
| GI_9845497-S | LAMC1 | laminin, gamma 1 (formerly LAMB2) |
| GI_16554581-S | COL5A3 | collagen, type V, alpha 3 |
| GI_40317625-S | THBS1 | thrombospondin 1 |

Citrate cycle (TCA cycle) - *Homo sapiens* (human)

| Gene ID | Symbol | Description |
|---|---|---|
| GI_4504374-S | CFH1/HF1 | complement factor H |
| GI_21735620-S | MDH2 | malate dehydrogenase 2, NAD (mitochondrial) |

Complement and coagulation cascades - *Homo sapiens* (human)

| Gene ID | Symbol | Description |
|---|---|---|
| GI_4505862-S | PLAU | plasminogen activator, urokinase |
| GI_4504374-S | CFH1/HF1 | complement factor H |
| GI_31542249-S | C1R | complement component 1, r subcomponent |

Cytokine-cytokine receptor interaction - *Homo sapiens* (human)

| Gene ID | Symbol | Description |
|---|---|---|
| GI_4506832-S | CCL1 | chemokine (C-C motif) ligand 1 |
| GI_22538399-S | CCL11 | chemokine (C-C motif) ligand 11 |
| GI_34335180-A | CCL15 | chemokine (C-C motif) ligand 15 |
| GI_22538800-S | CCL16 | chemokine (C-C motif) ligand 16 |
| GI_22538812-S | CCL2 | chemokine (C-C motif) ligand 2 |
| GI_22538807-A | CCL23 | chemokine (C-C motif) ligand 23 |
| GI_22165426-S | CCL24 | chemokine (C-C motif) ligand 24 |
| GI_22547151-S | CCL26 | chemokine (C-C motif) ligand 26 |
| GI_22538813-S | CCL5 | chemokine (C-C motif) ligand 5 |
| GI_13435401-S | CCL7 | chemokine (C-C motif) ligand 7 |
| GI_22538815-S | CCL8 | chemokine (C-C motif) ligand 8 |
| GI_27262662-A | CSF1 | colony stimulating factor 1 (macrophage) |
| GI_27437029-S | CSF2 | colony stimulating factor 2 (granulocyte-macrophage) |
| GI_27437048-A | CSF3 | colony stimulating factor 3 (granulocyte) |
| GI_4506856-S | CX3CL1 | chemokine (C—X3—C motif) ligand 1 |
| GI_4504152-S | CXCL1 | chemokine (C—X—C motif) ligand 1 (melanoma growth stimulating activity, alpha) |
| GI_14790145-S | CXCL11 | chemokine (C—X—C motif) ligand 11 |
| GI_40316922-I | CXCL12 | chemokine (C—X—C motif) ligand 12 (stromal cell-derived factor 1) |
| GI_5453576-S | CXCL13 | chemokine (C—X—C motif) ligand 13 (B-cell chemoattractant) |
| GI_41872613-S | CXCL5 | chemokine (C—X—C motif) ligand 5 |
| GI_4504098-S | CXCR3 | chemokine (C—X—C motif) receptor 3 |
| GI_6031163-S | EGF | epidermal growth factor (beta-urogastrone) |
| GI_38455415-S | FLT3LG | fms-related tyrosine kinase 3 ligand |
| GI_33859834-S | HGF | hepatocyte growth factor (hepapoietin A; scatter factor) |
| GI_10835170-S | IFNG | interferon, gamma |
| GI_24430216-S | IL10 | interleukin 10 |
| GI_24497437-S | IL12B | interleukin 12B (natural killer cell stimulatory factor 2, cytotoxic lymphocyte maturation factor 2, p40) |
| GI_26787977-S | IL13 | interleukin 13 |
| GI_27894329-S | IL1A | interleukin 1, alpha |
| GI_27894305-S | IL1B | interleukin 1, beta |
| GI_28178860-S | IL2 | interleukin 2 |
| GI_28416914-S | IL3 | interleukin 3 (colony-stimulating factor, multiple) |
| GI_10834983-S | IL6 | interleukin 6 (interferon, beta 2) |
| GI_28610152-S | IL7 | interleukin 7 |
| GI_28610153-S | IL8 | interleukin 8 |
| GI_11321596-S | KDR | kinase insert domain receptor (a type III receptor tyrosine kinase) |
| GI_4580419-A | KITLG | KIT ligand |
| GI_4557714-S | LEP | leptin (obesity homolog, mouse) |
| GI_6006018-S | LIF | leukemia inhibitory factor (cholinergic differentiation factor) |
| GI_15451785-A | PDGFB | platelet-derived growth factor beta polypeptide (simian sarcoma viral (v-sis) oncogene homolog) |
| GI_15451788-S | PDGFRB | platelet-derived growth factor receptor, beta polypeptide |
| GI_10863872-S | TGFB1 | transforming growth factor, beta 1 (Camurati-Engelmann disease) |
| GI_4507462-S | TGFB2 | transforming growth factor, beta 2 |
| GI_40805871-S | THPO | thrombopoietin (myeloproliferative leukemia virus oncogene ligand, megakaryocyte growth and development factor) |
| GI_4507508-S | TIMP1 | TIMP metallopeptidase inhibitor 1 |
| GI_25952110-S | TNF | tumor necrosis factor (TNF superfamily, member 2) |
| GI_22547122-S TNFRSF11B | | tumor necrosis factor receptor superfamily, member 11b (osteoprotegerin) |
| GI_30172563-S | VEGF | vascular endothelial growth factor |
| GI_4506852-S | XCL1 | chemokine (C motif) ligand 1 |

ECM-receptor interaction - *Homo sapiens* (human)

| Gene ID | Symbol | Description |
|---|---|---|
| GI_9845497-S | LAMC1 | laminin, gamma 1 (formerly LAMB2) |
| GI_14719826-S | COL1A1 | collagen, type I, alpha 1 |

TABLE D4-continued

Listing of 201 Genes in Each of the 30 Pathways (Genes of
Mesenchymal Stem Cell Conditioned Medium (MSC-CM))

| | | |
|---|---|---|
| GI_21536289-S | COL1A2 | collagen, type I, alpha 2 |
| GI_15149480-S | COL3A1 | collagen, type III, alpha 1 (Ehlers-Danlos syndrome type IV, autosomal dominant) |
| GI_45580690-S | COL4A1 | collagen, type IV, alpha 1 |
| GI_17986276-S | COL4A2 | collagen, type IV, alpha 2 |
| GI_16554578-S | COL5A1 | collagen, type V, alpha 1 |
| GI_16554580-S | COL5A2 | collagen, type V, alpha 2 |
| GI_15011912-S | COL6A1 | collagen, type VI, alpha 1 |
| GI_17402876-A | COL6A2 | collagen, type VI, alpha 2 |
| GI_17149810-A | COL6A3 | collagen, type VI, alpha 3 |
| GI_18375521-A | COL11A1 | collagen, type XI, alpha 1 |
| GI_16554581-S | COL5A3 | collagen, type V, alpha 3 |
| GI_16933543-A | FN1 | fibronectin 1 |
| GI_40317625-S | THBS1 | thrombospondin 1 |
| GI_7427516-S | HSPG2 | heparan sulfate proteoglycan 2 (perlecan) |
| GI_21361192-S | CD44 | CD44 antigen (homing function and Indian blood group system) |

Epithelial cell signaling in *Helicobacter pylori* infection - *Homo sapiens* (human)

| | | |
|---|---|---|
| GI_22538813-S | CCL5 | chemokine (C-C motif) ligand 5 |
| GI_4504152-S | CXCL1 | chemokine (C—X—C motif) ligand 1 (melanoma growth stimulating activity, alpha) |
| GI_28610153-S | IL8 | interleukin 8 |

Fc epsilon RI signaling pathway - *Homo sapiens* (human)

| | | |
|---|---|---|
| GI_25952110-S | TNF | tumor necrosis factor (TNF superfamily, member 2) |
| GI_26787977-S | IL13 | interleukin 13 |
| GI_27437029-S | CSF2 | colony stimulating factor 2 (granulocyte-macrophage) |
| GI_41281560-S | CLSTN1 | calsyntenin 1 |
| GI_28416914-S | IL3 | interleukin 3 (colony-stimulating factor, multiple) |

Focal adhesion - *Homo sapiens* (human)

| | | |
|---|---|---|
| GI_5016088-S | ACTB | actin, beta |
| GI_10938011-S | ACTC | actin, alpha, cardiac muscle |
| GI_11038618-S | ACTG1 | actin, gamma 1 |
| GI_41281560-S | CLSTN1 | calsyntenin 1 |
| GI_18375521-A | COL11A1 | collagen, type XI, alpha 1 |
| GI_14719826-S | COL1A1 | collagen, type I, alpha 1 |
| GI_21536289-S | COL1A2 | collagen, type I, alpha 2 |
| GI_15149480-S | COL3A1 | collagen, type III, alpha 1 (Ehlers-Danlos syndrome type IV, autosomal dominant) |
| GI_45580690-S | COL4A1 | collagen, type IV, alpha 1 |
| GI_17986276-S | COL4A2 | collagen, type IV, alpha 2 |
| GI_16554578-S | COL5A1 | collagen, type V, alpha 1 |
| GI_16554580-S | COL5A2 | collagen, type V, alpha 2 |
| GI_16554581-S | COL5A3 | collagen, type V, alpha 3 |
| GI_15011912-S | COL6A1 | collagen, type VI, alpha 1 |
| GI_17402876-A | COL6A2 | collagen, type VI, alpha 2 |
| GI_17149810-A | COL6A3 | collagen, type VI, alpha 3 |
| GI_6031163-S | EGF | epidermal growth factor (beta-urogastrone) |
| GI_4503744-S | FLNA | filamin A, alpha (actin binding protein 280) |
| GI_16933543-A | FN1 | fibronectin 1 |
| GI_33859834-S | HGF | hepatocyte growth factor (hepapoietin A; scatter factor) |
| GI_19923111-S | IGF1 | insulin-like growth factor 1 (somatomedin C) |
| GI_10834983-S | IL6 | interleukin 6 (interferon, beta 2) |
| GI_11321596-S | KDR | kinase insert domain receptor (a type III receptor tyrosine kinase) |
| GI_9845497-S | LAMC1 | laminin, gamma 1 (formerly LAMB2) |
| GI_15451785-A | PDGFB | platelet-derived growth factor beta polypeptide (simian sarcoma viral (v-sis) oncogene homolog) |
| GI_15451788-S | PDGFRB | platelet-derived growth factor receptor, beta polypeptide |
| GI_40317625-S | THBS1 | thrombospondin 1 |
| GI_30172563-S | VEGF | vascular endothelial growth factor |

Gap junction - *Homo sapiens* (human)

| | | |
|---|---|---|
| GI_5174476-S K-ALPHA-1 | | tubulin, alpha, ubiquitous |
| GI_17986282-S | TUBA3 | tubulin, alpha 3 |
| GI_31880337-S | TUBA6 | tubulin, alpha 6 |
| GI_15451788-S | PDGFRB | platelet-derived growth factor receptor, beta polypeptide |
| GI_6031163-S | EGF | epidermal growth factor (beta-urogastrone) |
| GI_15451785-A | PDGFB | platelet-derived growth factor beta polypeptide (simian sarcoma viral (v-sis) oncogene homolog) |

Glycolysis or Gluconeogenesis - *Homo sapiens* (human)

| | | |
|---|---|---|
| GI_16507965-S | ENO1 | enolase 1, (alpha) |
| GI_16507966-S | ENO2 | enolase 2 (gamma, neuronal) |
| GI_26024330-S | TPI1 | triosephosphate isomerase 1 |

TABLE D4-continued

Listing of 201 Genes in Each of the 30 Pathways (Genes of
Mesenchymal Stem Cell Conditioned Medium (MSC-CM))

| | | |
|---|---|---|
| GI_22095338-S | PGK1 | phosphoglycerate kinase 1 |
| GI_31543396-S | PGK2 | phosphoglycerate kinase 2 |

Hematopoietic cell lineage - *Homo sapiens* (human)

| | | |
|---|---|---|
| GI_21361192-S | CD44 | CD44 antigen (homing function and Indian blood group system) |
| GI_4503744-S | FLNA | filamin A, alpha (actin binding protein 280) |
| GI_40805871-S | THPO | thrombopoietin (myeloproliferative leukemia virus oncogene ligand, megakaryocyte growth and development factor) |
| GI_4507508-S | TIMP1 | TIMP metallopeptidase inhibitor 1 |
| GI_25952110-S | TNF | tumor necrosis factor (TNF superfamily, member 2) |
| GI_27262662-A | CSF1 | colony stimulating factor 1 (macrophage) |
| GI_27437048-A | CSF3 | colony stimulating factor 3 (granulocyte) |
| GI_38455415-S | FLT3LG | fms-related tyrosine kinase 3 ligand |
| GI_10834983-S | IL6 | interleukin 6 (interferon, beta 2) |
| GI_27437029-S | CSF2 | colony stimulating factor 2 (granulocyte-macrophage) |
| GI_27894329-S | IL1A | interleukin 1, alpha |
| GI_27894305-S | IL1B | interleukin 1, beta |
| GI_28416914-S | IL3 | interleukin 3 (colony-stimulating factor, multiple) |
| GI_28610152-S | IL7 | interleukin 7 |
| GI_4580419-A | KITLG | KIT ligand |

Inositol metabolism - *Homo sapiens* (human)

| | | |
|---|---|---|
| GI_26024330-S | TPI1 | triosephosphate isomerase 1 |

Insulin signaling pathway - *Homo sapiens* (human)

| | | |
|---|---|---|
| GI_31377794-S | CALM1 | calmodulin 1 (phosphorylase kinase, delta) |
| GI_41281560-S | CLSTN1 | calsyntenin 1 |

Jak-STAT signaling pathway - *Homo sapiens* (human)

| | | |
|---|---|---|
| GI_41281560-S | CLSTN1 | calsyntenin 1 |
| GI_27437029-S | CSF2 | colony stimulating factor 2 (granulocyte-macrophage) |
| GI_27437048-A | CSF3 | colony stimulating factor 3 (granulocyte) |
| GI_10835170-S | IFNG | interferon, gamma |
| GI_24430216-S | IL10 | interleukin 10 |
| GI_24497437-S | IL12B | interleukin 12B (natural killer cell stimulatory factor 2, cytotoxic lymphocyte maturation factor 2, p40) |
| GI_26787977-S | IL13 | interleukin 13 |
| GI_28178860-S | IL2 | interleukin 2 |
| GI_28416914-S | IL3 | interleukin 3 (colony-stimulating factor, multiple) |
| GI_10834983-S | IL6 | interleukin 6 (interferon, beta 2) |
| GI_28610152-S | IL7 | interleukin 7 |
| GI_4557714-S | LEP | leptin (obesity homolog, mouse) |
| GI_6006018-S | LIF | leukemia inhibitory factor (cholinergic differentiation factor) |
| GI_40805871-S | THPO | thrombopoietin (myeloproliferative leukemia virus oncogene ligand, megakaryocyte growth and development factor) |
| GI_4507508-S | TIMP1 | TIMP metallopeptidase inhibitor 1 |

Leukocyte transendothelial migration - *Homo sapiens* (human)

| | | |
|---|---|---|
| GI_4826835-S | MMP9 | matrix metallopeptidase 9 (gelatinase B, 92 kDa gelatinase, 92 kDa type IV collagenase) |
| GI_5453576-S | CXCL13 | chemokine (C—X—C motif) ligand 13 (B-cell chemoattractant) |
| GI_28610153-S | IL8 | interleukin 8 |
| GI_40316922-I | CXCL12 | chemokine (C—X—C motif) ligand 12 (stromal cell-derived factor 1) |
| GI_41281560-S | CLSTN1 | calsyntenin 1 |
| GI_5016088-S | ACTB | actin, beta |
| GI_10938011-S | ACTC | actin, alpha, cardiac muscle |
| GI_11038618-S | ACTG1 | actin, gamma 1 |

MAPK signaling pathway - *Homo sapiens* (human)

| | | |
|---|---|---|
| GI_34106709-A | BDNF | brain-derived neurotrophic factor |
| GI_6031163-S | EGF | epidermal growth factor (beta-urogastrone) |
| GI_4503692-S | FGF17 | fibroblast growth factor 17 |
| GI_4503700-S | FGF4 | fibroblast growth factor 4 (heparin secretory transforming protein 1, Kaposi sarcoma oncogene) |
| GI_10337586-S | FGF6 | fibroblast growth factor 6 |
| GI_15147344-S | FGF7 | fibroblast growth factor 7 (keratinocyte growth factor) |
| GI_4503706-S | FGF9 | fibroblast growth factor 9 (glia-activating factor) |
| GI_13186266-A | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| GI_4503744-S | FLNA | filamin A, alpha (actin binding protein 280) |
| GI_40549401-A | GDNF | glial cell derived neurotrophic factor |
| GI_24234685-A | HSPA8 | heat shock 70 kDa protein 8 |
| GI_27894329-S | IL1A | interleukin 1, alpha |
| GI_27894305-S | IL1B | interleukin 1, beta |
| GI_15451785-A | PDGFB | platelet-derived growth factor beta polypeptide (simian sarcoma viral (v-sis) oncogene homolog) |

TABLE D4-continued

Listing of 201 Genes in Each of the 30 Pathways (Genes of
Mesenchymal Stem Cell Conditioned Medium (MSC-CM))

| | | |
|---|---|---|
| GI_15451788-S | PDGFRB | platelet-derived growth factor receptor, beta polypeptide |
| GI_10863872-S | TGFB1 | transforming growth factor, beta 1 (Camurati-Engelmann disease) |
| GI_4507462-S | TGFB2 | transforming growth factor, beta 2 |
| GI_25952110-S | TNF | tumor necrosis factor (TNF superfamily, member 2) |

Methane metabolism - *Homo sapiens* (human)

| | | |
|---|---|---|
| GI_40805871-S | THPO | thrombopoietin (myeloproliferative leukemia virus oncogene ligand, megakaryocyte growth and development factor) |
| GI_32455261-A | PRDX5 | peroxiredoxin 5 | mTOR signaling pathway - *Homo sapiens* (human)

| | | |
|---|---|---|
| GI_30172563-S | VEGF | vascular endothelial growth factor |
| GI_41281560-S | CLSTN1 | calsyntenin 1 |
| GI_19923111-S | IGF1 | insulin-like growth factor 1 (somatomedin C) |

Phenylalanine, tyrosine and tryptophan biosynthesis - *Homo sapiens* (human)

| | | |
|---|---|---|
| GI_16507965-S | ENO1 | enolase 1, (alpha) |
| GI_16507966-S | ENO2 | enolase 2 (gamma, neuronal) |

Phenylalanine metabolism - *Homo sapiens* (human)

| | | |
|---|---|---|
| GI_4505184-S | MIF | macrophage migration inhibitory factor (glycosylation-inhibiting factor) |
| GI_40805871-S | THPO | thrombopoietin (myeloproliferative leukemia virus oncogene ligand, megakaryocyte growth and development factor) |
| GI_32455261-A | PRDX5 | peroxiredoxin 5 |

Regulation of actin cytoskeleton - *Homo sapiens* (human)

| | | |
|---|---|---|
| GI_5016088-S | ACTB | actin, beta |
| GI_10938011-S | ACTC | actin, alpha, cardiac muscle |
| GI_11038618-S | ACTG1 | actin, gamma 1 |
| GI_5031634-S | CFL1 | cofilin 1 (non-muscle) |
| GI_41281560-S | CLSTN1 | calsyntenin 1 |
| GI_6031163-S | EGF | epidermal growth factor (beta-urogastrone) |
| GI_4503692-S | FGF17 | fibroblast growth factor 17 |
| GI_4503700-S | FGF4 | fibroblast growth factor 4 (heparin secretory transforming protein 1, Kaposi sarcoma oncogene) |
| GI_10337586-S | FGF6 | fibroblast growth factor 6 |
| GI_15147344-S | FGF7 | fibroblast growth factor 7 (keratinocyte growth factor) |
| GI_4503706-S | FGF9 | fibroblast growth factor 9 (glia-activating factor) |
| GI_13186266-A | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| GI_16933543-A | FN1 | fibronectin 1 |
| GI_38044287-A | GSN | gelsolin (amyloidosis, Finnish type) |
| GI_22507396-S | MYH9 | myosin, heavy polypeptide 9, non-muscle |
| GI_15451785-A | PDGFB | platelet-derived growth factor beta polypeptide (simian sarcoma viral (v-sis) oncogene homolog) |
| GI_15451788-S | PDGFRB | platelet-derived growth factor receptor, beta polypeptide |
| GI_16753213-S | PFN1 | profilin 1 |
| GI_34328943-S | TMSB4X | thymosin, beta 4, X-linked |
| GI_34013529-S | TMSL3 | thymosin-like 3 |

Stilbene, coumarine and lignin biosynthesis - *Homo sapiens* (human)

| | | |
|---|---|---|
| GI_40805871-S | THPO | thrombopoietin (myeloproliferative leukemia virus oncogene ligand, megakaryocyte growth and development factor) |
| GI_32455261-A | PRDX5 | peroxiredoxin 5 |

T cell receptor signaling pathway - *Homo sapiens* (human)

| | | |
|---|---|---|
| GI_25952110-S | TNF | tumor necrosis factor (TNF superfamily, member 2) |
| GI_27437029-S | CSF2 | colony stimulating factor 2 (granulocyte-macrophage) |
| GI_10835170-S | IFNG | interferon, gamma |
| GI_24430216-S | IL10 | interleukin 10 |
| GI_28178860-S | IL2 | interleukin 2 |
| GI_41281560-S | CLSTN1 | calsyntenin 1 |

TGF-beta signaling pathway - *Homo sapiens* (human)

| | | |
|---|---|---|
| GI_4557730-S | LTBP1 | latent transforming growth factor beta binding protein 1 |
| GI_40317625-S | THBS1 | thrombospondin 1 |
| GI_10863872-S | TGFB1 | transforming growth factor, beta 1 (Camurati-Engelmann disease) |
| GI_4507462-S | TGFB2 | transforming growth factor, beta 2 |
| GI_25952110-S | TNF | tumor necrosis factor (TNF superfamily, member 2) |
| GI_10835170-S | IFNG | interferon, gamma |

Tight junction - *Homo sapiens* (human)

| | | |
|---|---|---|
| GI_5016088-S | ACTB | actin, beta |
| GI_10938011-S | ACTC | actin, alpha, cardiac muscle |
| GI_11038618-S | ACTG1 | actin, gamma 1 |
| GI_22507396-S | MYH9 | myosin, heavy polypeptide 9, non-muscle |

TABLE D4-continued

Listing of 201 Genes in Each of the 30 Pathways (Genes of Mesenchymal Stem Cell Conditioned Medium (MSC-CM))

Toll-like receptor signaling pathway - *Homo sapiens* (human)

| | | |
|---|---|---|
| GI_14790145-S | CXCL11 | chemokine (C—X—C motif) ligand 11 |
| GI_28610153-S | IL8 | interleukin 8 |
| GI_24497437-S | IL12B | interleukin 12B (natural killer cell stimulatory factor 2, cytotoxic lymphocyte maturation factor 2, p40) |
| GI_27894305-S | IL1B | interleukin 1, beta |
| GI_41281560-S | CLSTN1 | calsyntenin 1 |
| GI_10834983-S | IL6 | interleukin 6 (interferon, beta 2) |
| GI_22538813-S | CCL5 | chemokine (C-C motif) ligand 5 |
| GI_25952110-S | TNF | tumor necrosis factor (TNF superfamily, member 2) |

Type I diabetes mellitus - *Homo sapiens* (human)

| | | |
|---|---|---|
| GI_24497437-S | IL12B | interleukin 12B (natural killer cell stimulatory factor 2, cytotoxic lymphocyte maturation factor 2, p40) |
| GI_28178860-S | IL2 | interleukin 2 |
| GI_10835170-S | IFNG | interferon, gamma |
| GI_27894329-S | IL1A | interleukin 1, alpha |
| GI_27894305-S | IL1B | interleukin 1, beta |
| GI_25952110-S | TNF | tumor necrosis factor (TNF superfamily, member 2) |

593 Genes and 794 Gene Products

The particle may additionally, or alternatively, comprise any of the gene products of the 593 genes and/or 794 gene products listed below in Table D5.

Accordingly, the particle may be employed to affect, control or regulate any of the biological processes or pathways the genes or gene products are involved in.

TABLE D5

593 Additional Proteins in Mesenchymal Stem Cell Conditioned Medium (MSC-CM)
Total 593 unique gene products: set 1-4 (3 of 4 & 4 of 4) without common genes in 201 list

| | | | | | | | |
|---|---|---|---|---|---|---|---|
| 02-Sep | CAND1 | DDX17 | H2AFY | KRTHB4 | PCBP2 | QARS | STC1 |
| 07-Sep | CAP1 | DES | HADH | LAMA4 | PCDH18 | QPCT | STIP1 |
| AARS | CAP2 | DLD | HARS | LAMB1 | PCDHGB6 | RAB11B | SULF1 |
| ACAA2 | CAPG | DNAJC3 | HARS2 | LANCL1 | PCK2 | RAB1A | SYNCRIP |
| ACAT2 | CAPN1 | DPP3 | hCG_1641617 | LAP3 | PCMT1 | RAB6A | TALDO1 |
| ACO1 | CAPN2 | DPYSL2 | hCG_2023776 | LASP1 | PCNA | RAC1 | TARS |
| ACTN1 | CAPZA1 | DPYSL3 | HEXA | LDHA | PDCD6IP | RAN | TCN2 |
| ACTN2 | CAPZA2 | DSTN | HEXB | LDHAL6B | PDGFC | RANBP5 | TCP1 |
| ACTN3 | CAPZB | DYNLL1 | HIBCH | LDHB | PDIA3 | RARRES2 | TFPI |
| ACTN4 | CARS | ECHS1 | HINT1 | LEPRE1 | PDIA4 | RARS | THBS2 |
| ACTR1A | CBR1 | EEF1A1 | HIST1H4 | LGALS3 | PDIA6 | RBMX | THOP1 |
| ACTR1B | CBR3 | EEF1A2 | HIST1H4A | LOC196463 | PDLIM1 | RHOA | THY1 |
| ACTR2 | CCBL2 | EEF1B2 | HIST1H4B | LOC283523 | PDLIM5 | RNASE4 | TKT |
| ACTR3 | CCDC19 | EEF2 | HIST1H4C | LOC347701 | PDLIM7 | RNH1 | TLN1 |
| ACTR3B | CCT2 | EFEMP2 | HIST1H4D | LOC646821 | PEPD | RNPEP | TMOD2 |
| ADAM9 | CCT3 | EIF2S3 | HIST1H4E | LOC649125 | PFN2 | RPL10A | TMOD3 |
| ADSL | CCT4 | EIF3S9 | HIST1H4F | LOC653214 | PGCP | RPL11 | TNC |
| ADSS | CCT5 | EIF4A1 | HIST1H4H | LOC654188 | PGD | RPL12 | TNPO1 |
| AEBP1 | CCT6A | EIF4A2 | HIST1H4I | LOC728378 | PGLS | RPL14 | TP53I3 |
| AGA | CCT7 | EMILIN1 | HIST1H4J | LOXL2 | PGM1 | RPL18 | TPM1 |
| AHCY | CCT8 | ENO3 | HIST1H4K | LRP1 | PGRMC2 | RPL22 | TPM2 |
| AK1 | CD248 | EPPK1 | HIST1H4L | LTA4H | PHGDH | RPL30 | TPM3 |
| AK2 | CD59 | EPRS | HIST2H2AA3 | LTB4DH | PHPT1 | RPL5 | TRAP1 |
| AKR1A1 | CD81 | ESD | HIST2H2AA4 | LTBP2 | PICALM | RPL7 | TRHDE |
| AKR1B1 | CD9 | ETF1 | HIST2H2AA | M6PRBP1 | PKM2 | RPLP0 | TROVE2 |
| ALDH2 | CDC37 | ETFB | HIST2H4B | MACF1 | PLEKHC1 | RPLP1 | TSKU |
| ALDH7A1 | CDC42 | ETHE1 | HIST4H4 | MAP1B | PLOD1 | RPLP2 | TUBA1A |
| ALDOA | CFL2 | EXT1 | HLA-A | MAPK1 | PLOD2 | RPS10 | TUBA8 |
| ALDOC | CHID1 | FAH | HLA-B | MAPRE1 | PLOD3 | RPS15A | TUBB |
| ANXA1 | CLEC11A | FAHD1 | HMX1 | MAT2A | PLS1 | RPS16 | TUBB2C |
| ANXA5 | CLIC1 | FAM129B | HNRPA1 | MAT2B | PLS3 | RPS19 | TUBB3 |
| ANXA6 | CLIC4 | FAM3C | HNRPA1L-2 | MCTS1 | PLSCR3 | RPS2 | TUBB4 |
| AP1B1 | CLTC | FAM49B | HNRPA2B1 | MDH1 | POSTN | RPS20 | TUBB6 |
| AP1S1 | CLTCL1 | FAM62A | HNRPC | MFAP4 | PPCS | RPS23 | TUBB8 |
| AP2A1 | CLU | FBLN5 | HNRPD | MGAT5 | PPIB | RPS3 | TWF1 |
| AP2A2 | CMPK | FDPS | HNRPDL | MMP14 | PPP2R1A | RPS4X | TXNL5 |
| AP2B1 | CNDP2 | FH | HNRPH2 | MMP2 | PPP2R4 | RPS5 | UBE1 |
| AP3B1 | CNN2 | FKBP10 | HNRPK | MRLC2 | PPP5C | RPS7 | UBE2L3 |
| APEX1 | CNN3 | FKBP1A | HNRPL | MSN | PPP6C | RPS8 | UBE2N |

TABLE D5-continued

593 Additional Proteins in Mesenchymal Stem Cell Conditioned Medium (MSC-CM)
Total 593 unique gene products: set 1-4 (3 of 4 & 4 of 4) without common genes in 201 list

| | | | | | | | |
|---|---|---|---|---|---|---|---|
| API5 | COL18A1 | FKBP3 | HNRPR | MTAP | PRDX2 | RPS9 | UBE2V1 |
| APOA1BP | COL2A1 | FLNB | HNRPU | MTPN | PRDX3 | RPSA | UBE3B |
| APOE | COL4A2 | FLNC | HSP90AB1 | MVP | PRDX4 | RSU1 | UCHL3 |
| APP | COL5A1 | FLRT2 | HSP90B1 | MXRA5 | PRDX6 | S100A16 | UGDH |
| APRT | COL5A2 | FLT1 | HSPA1A | MXRA8 | PRG1 | SARS | UGP2 |
| ARCN1 | COL6A2 | FSCN1 | HSPA1B | MYH14 | PRKACA | SDC4 | UROD |
| ARHGAP1 | COL7A1 | FSTL5 | HSPA1L | MYL6 | PRKCSH | SDCBP | USP14 |
| ARPC1A | COL7A1 | FTL | HSPA4 | NAGK | PRNP | SEC22B | USP5 |
| ARPC1B | COL7A1 | G6PD | HSPA5 | NANS | PROCR | SEC23A | VARS |
| ARPC2 | COL7A1 | GALNT2 | HSPA6 | NARS | PROSC | SEC31A | VASN |
| ARPC3 | COPA | GANAB | HSPB1 | NEDD8 | PRSS23 | SEMA3C | VAT1 |
| ARPC4 | COPG | GAPDH | HSPD1 | NEFM | PRSS3 | SEMA7A | VCL |
| ARTS-1 | COPS3 | GARS | HSPH1 | NIT2 | PSAT1 | SERPINB1 | VCP |
| ATIC | COPS4 | GAS6 | HTRA1 | NME1 | PSMA1 | SERPINB6 | VIL2 |
| ATP5B | COPS8 | GBA | IDH1 | NPC2 | PSMA2 | SERPINE1 | VIM |
| ATP6AP1 | CORO1B | GBE1 | IGFBP3 | NPEPPS | PSMA3 | SERPINE2 | VPS26A |
| CORO1C | GDF15 | IGKC | NQO1 | PSMA6 | SERPINF1 | VTN | VPS35 |
| COTL1 | GDI1 | ILF2 | NRP1 | PSMA7 | SERPINH1 | WARS | VTN |
| CRIP2 | GDI2 | ILF3 | NRP2 | PSMB1 | SERPINI2 | WDR1 | WARS |
| CS | GLO1 | INHBA | NT5E | PSMB2 | SFRP1 | WNT5A | WDR1 |
| BASP1 | CSE1L | GLT8D3 | IQGAP1 | NUCB1 | PSMB3 | SIL1 | WNT5A |
| BAT1 | CSRP1 | GLUD1 | ISOC1 | OLFML3 | PSMB4 | SLC1A5 | WNT5B |
| BBS1 | CSRP2 | GM2A | ITGA2 | P4HA1 | PSMB5 | SLC3A2 | XPO1 |
| BCAT1 | CST3 | GNPDA1 | ITGB4BP | P4HB | PSMD11 | SND1 | YKT6 |
| BGN | CTGF | GNPNAT1 | KPNB1 | PABPC1 | PSMD13 | SNRPD1 | YWHAB |
| BLVRA | CTHRC1 | GOT1 | KRT1 | PABPC4 | PSMD5 | SNRPE | YWHAE |
| BPNT1 | CTSD | GOT2 | KRT14 | PAFAH1B1 | PSMD6 | SPOCK | YWHAG |
| BTD | CTSZ | GPC1 | KRT2 | PAFAH1B2 | PSMD7 | SPTAN1 | YWHAH |
| C14orf141 | CYCS | GPI | KRT27 | PAFAH1B3 | PSME2 | SPTBN4 | YWHAQ |
| C19orf10 | D4ST1 | GREM1 | KRT4 | PAICS | PTBP1 | SRP9 | |
| C1orf58 | DAG1 | GRHPR | KRT5 | PAM | PTPRCAP | SRPX | |
| C1orf78 | DCI | GSR | KRT6L | PAPPA | PTX3 | SRPX2 | |
| C1QBP | DCN | GSS | KRT7 | PARK7 | PURA | SSB | |
| C1S | DDAH2 | GSTK1 | KRT75 | PARP1 | PXDN | ST13 | |
| C21orf33 | DDB1 | GSTO1 | KRT77 | PARVA | PYCR1 | ST6GAL2 | |
| CALR | DDT | GTPBP9 | KRT9 | PCBP1 | PYGB | STAT1 | |

Exosome

The particle may in particular comprise a vesicle. The particle may comprise an exosome.

The Examples describe the isolation of the active component in the secretion that confers cardioprotection against the reperfusion injury. The active component may comprise an exosome secreted by the mesenchymal stem cells (MSCs).

Exosomes are small membrane vesicles formed in late endocytic compartments (multivesicular bodies) first described to be secreted by reticulocytes in 1983[21] and subsequently found to be secreted by many cells types including various haematopoietic cells, tumours of haematopoietic or non-haematopoietic origin and epithelial cells[22]. They are distinct entities from the more recently described 'ribonuclease complex' also named exosome[23].

Exosomes may be defined by morphological and biochemical parameters (see reviews[22, 24-35]). Accordingly, the particles described here may comprise one or more of these morphological or biochemical parameters.

Exosomes are classically defined as "saucer-like" vesicles or a flattened sphere limited by a lipid bilayer with diameters of 40-100 nm and are formed by inward budding of the endosomal membrane. Like all lipid vesicles and unlike protein aggregates or nucleosomal fragments that are released by apoptotic cells, exosomes have a density of ~1.13-1.19 g/ml and float on sucrose gradients. Exosomes are enriched in cholesterol and sphingomyelin, and lipid raft markers such as GM1, GM3, flotillin and the src protein kinase Lyn suggesting that their membranes are enriched in lipid rafts.

The molecular composition of exosomes from different cell types and of different species has been examined. In general, exosomes contain ubiquitous proteins that appear to be common to all exosomes and proteins that are cell-type specific. Also, proteins in exosomes from the same cell-type but of different species are highly conserved. The ubiquitous exosome-associated proteins include cytosolic proteins found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. The tetraspannins are highly enriched in exosomes and are known to be involved in the organization of large molecular complexes and membrane subdomains.

Examples of cell-type specific proteins in exosomes are MHC class II molecules in exosomes from MHC class II-expressing cells, CD86 in dendritic cell-derived exosomes, T-cell receptors on T-cell-derived exosomes etc. Notably, exosomes do not contain proteins of nuclear, mitochondrial, endoplasmic-reticulum or Golgi-apparatus origin. Also, highly abundant plasma membrane proteins are absent in exosomes suggesting that they are not simply fragments of the plasma membrane. Many of the reported ubiquitous exosome-associated proteins are also present in the proteomic profile of the hESC-MSC secretion.

Exosomes are also known to contain mRNA and microRNA, which can be delivered to another cell, and can be functional in this new location[36]. The physiological functions of exosome remain poorly defined. It is thought to help eradicate obsolete proteins, recycle proteins, mediate transmission of infectious particles such as prions and viruses, induce complement resistance, facilitate immune cell-cell communication and transmit cell signaling[1, 22, 25-28, 37-40]. Exosomes have been used in immunotherapy for treatment of cancer[34]

Uses of Particles from Mesenchymal Stem Cells

The particle may be used as a substitute for an MSC or MSC-CM, as described above In particular, the particle may be used for any of the therapeutic purposes that MSCs or MSC-CMs are currently being used, or in the future may be used.

It will be evident that the methods and compositions described here enable the production of particles from mesenchymal stem cells. Thus, any uses of mesenchymal stem cells will equally attach to particles from mesenchymal stem cells.

Mesenchymal stem cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer. Accordingly, particles from MSCs may be used to treat such diseases.

Particles from mesenchymal stem cells such as those made according to the methods and compositions described here may be used for a variety of commercially important research, diagnostic, and therapeutic purposes.

The particles from mesenchymal stem cells may in particular be used for the preparation of a pharmaceutical composition for the treatment of disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Mesenchymal stem cells made by the methods and compositions described here have similar or identical properties to bone marrow derived mesenchymal stem cells (BM-MSCs). Therefore, the mesenchymal stem cells, and any differentiated cells made from these, as well as particles derived therefrom, may be used in any of the applications for which BM-MSCs are known to be used, or in which it is possible for them to be used.

Diseases Treatable by Particles from Mesenchymal Stem Cells

Analysis of the proteome of MSCs shows that the proteins expressed are involved in three biological processes: metabolism, defense response, and tissue differentiation including vascularization, hematopoiesis and skeletal development. Accordingly, the particles from MSCs described here may be used to treat diseases which these functions may have a role in, or whose repair or treatment involves any one or more of these biological processes. Similarly, the proteins expressed by the MSCs, singly or in combination, preferably in the form of particles as described here, may be used to supplement the activity of, or in place of, the MSCs, or media conditioned by the MSCs, for the purpose of for example treating or preventing such diseases.

The 201 gene products expressed by the MSCs are shown to activate important signalling pathways in cardiovascular biology, bone development and hematopoiesis such as Jak-STAT, MAPK, Toll-like receptor, TGF-beta signalling and mTOR signaling pathways. Accordingly, the particles from the MSCs, etc, may be used to prevent or treat a disease in which any of these signalling pathways is involved, or whose aetiology involves one or more defects in any one or more of these signalling pathways.

Accordingly, such particles may be used to treat cardiac failure, bone marrow disease, skin disease, burns and degenerative diseases such as diabetes, Alzheimer's disease, Parkinson's disease and cancer.

Such particles may also be used to treat myocardial infarction, a cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterised by initial injury inducing inflammation and immune dysregulation leading to chronic tissue remodeling including fibrosis and loss of function, renal ischemic injury, cystic fibrosis, sinusitis and rhinitis or an orthopaedic disease.

The particles may be used to aid wound healing, scar reduction, bone formation, a bone graft or bone marrow transplantation in an individual.

Unless the context dictates otherwise, the term "conditioned medium" should be taken to include not only cell culture medium exposed to MSCs as well as such a composition comprising one or more, preferably substantially all, the polypeptides which are present in the conditioned medium.

The particles may also be used as sources for any of the proteins secreted or expressed by the MSCs. We therefore provide for a method of producing a polypeptide as shown in any of Tables D1 to D5, the method comprising obtaining a particle as described, and isolating the polypeptide from the particle.

Heart Disease

The mesenchymal stem cell particle methods and compositions described here may be used for treatment or prevention of heart disease.

Heart disease is an umbrella term for a variety for different diseases affecting the heart. As of 2007, it is the leading cause of death in the United States, England, Canada and Wales, killing one person every 34 seconds in the United States alone. Heart disease includes any of the following.

Coronary Heart Disease

Coronary artery disease is a disease of the artery caused by the accumulation of atheromatous plaques within the walls of the arteries that supply the myocardium. Angina pectoris (chest pain) and myocardial infarction (heart attack) are symptoms of and conditions caused by coronary heart disease. Over 459,000 Americans die of coronary heart disease every year. In the United Kingdom, 101,000 deaths annually are due to coronary heart disease.

Cardiomyopathy

Cardiomyopathy is the deterioration of the function of the myocardium (i.e., the actual heart muscle) for any reason. People with cardiomyopathy are often at risk of arrhythmia and/or sudden cardiac death. Extrinsic cardiomyopathies—cardiomyopathies where the primary pathology is outside the myocardium itself comprise the majority of cardiomyopathies. By far the most common cause of a cardiomyopathy is ischemia.

The World Health Organization includes as specific cardiomyopathies: Alcoholic cardiomyopathy, coronary artery disease, congenital heart disease, nutritional diseases affecting the heart, ischemic (or ischaemic) cardiomyopathy, hypertensive cardiomyopathy, valvular cardiomyopathy, inflammatory cardiomyopathy.

Also included are:

Cardiomyopathy secondary to a systemic metabolic disease

Intrinsic cardiomyopathies (weakness in the muscle of the heart that is not due to an identifiable external cause)

Dilated cardiomyopathy (DCM, the most common form, and one of the leading indications for heart transplantation. In DCM the heart (especially the left ventricle) is enlarged and the pumping function is diminished)

Hypertrophic cardiomyopathy (HCM or HOCM, a genetic disorder caused by various mutations in genes encoding sarcomeric proteins. In HCM the heart muscle is thickened, which can obstruct blood flow and prevent the heart from functioning properly), Arrhythmogenic right ventricular cardiomyopathy (ARVC, which arises from an electrical disturbance of the heart in which heart muscle is replaced by fibrous scar tissue. The right ventricle is generally most affected)

Restrictive cardiomyopathy (RCM, which is the least common cardiomyopathy. The walls of the ventricles are stiff, but may not be thickened, and resist the normal filling of the heart with blood).

Noncompaction Cardiomyopathy—the left ventricle wall has failed to properly grow from birth and such has a spongy appearance when viewed during an echocardiogram.

Cardiovascular Disease

Cardiovascular disease is any of a number of specific diseases that affect the heart itself and/or the blood vessel system, especially the veins and arteries leading to and from the heart. Research on disease dimorphism suggests that women who suffer with cardiovascular disease usually suffer from forms that affect the blood vessels while men usually suffer from forms that affect the heart muscle itself. Known or associated causes of cardiovascular disease include diabetes mellitus, hypertension, hyperhomocysteinemia and hypercholesterolemia.

Types of cardiovascular disease include atherosclerosis

Ischaemic Heart Disease

Ischaemic heart disease is disease of the heart itself, characterized by reduced blood supply to the organs. This occurs when the arteries that supply the oxygen and the nutrients gets stopped and the heart will not get enough of the oxygen and the nutrients and will eventually stop beating.

Heart Failure

Heart failure, also called congestive heart failure (or CHF), and congestive cardiac failure (CCF), is a condition that can result from any structural or functional cardiac disorder that impairs the ability of the heart to fill with or pump a sufficient amount of blood throughout the body. Cor pulmonale is a failure of the right side of the heart.

Hypertensive Heart Disease

Hypertensive heart disease is heart disease caused by high blood pressure, especially localised high blood pressure. Conditions that can be caused by hypertensive heart disease include: left ventricular hypertrophy, coronary heart disease, (Congestive) heart failure, hypertensive cardiomyopathy, cardiac arrhythmias, inflammatory heart disease, etc.

Inflammatory heart disease involves inflammation of the heart muscle and/or the tissue surrounding it. Endocarditis comprises inflammation of the inner layer of the heart, the endocardium. The most common structures involved are the heart valves. Inflammatory cardiomegaly. Myocarditis comprises inflammation of the myocardium, the muscular part of the heart.

Valvular Heart Disease

Valvular heart disease is disease process that affects one or more valves of the heart. The valves in the right side of the heart are the tricuspid valve and the pulmonic valve. The valves in the left side of the heart are the mitral valve and the aortic valve. Included are aortic valve stenosis, mitral valve prolapse and valvular cardiomyopathy.

[The above text is adapted from Heart disease. (2009, Feb. 3). In Wikipedia, The Free Encyclopedia. Retrieved 06:33, Feb. 20, 2009, from http://en.wikipedia.org/w/index.php?title=Heart_disease&oldid=268290924]

Delivery of Particles

The particles as described in this document may be delivered to the human or animal body by any suitable means.

We therefore describe a delivery system for delivering a particles as described in this document to a target cell, tissue, organ, animal body or human body, and methods for using the delivery system to deliver particles to a target.

The delivery system may comprise a source of particles, such as a container containing the particles. The delivery system may comprise a dispenser for dispensing the particles to a target.

Accordingly, we provide a delivery system for delivering a particles, comprising a source of particles as described in this document together with a dispenser operable to deliver the particles to a target.

We further provide for the use of such a delivery system in a method of delivering a particles to a target.

Delivery systems for delivering fluid into the body are known in the art, and include injection, surgical drips, catheters (including perfusion catheters) such as those described in U.S. Pat. No. 6,139,524, for example, drug delivery catheters such as those described in U.S. Pat. No. 7,122,019.

Delivery to the lungs or nasal passages, including intranasal delivery, may be achieved using for example a nasal spray, puffer, inhaler, etc as known in the art (for example as shown in U.S. Design Pat. D544,957.

Delivery to the kidneys may be achieved using an intra-aortic renal delivery catheter, such as that described in U.S. Pat. No. 7,241,273.

It will be evident that the particular delivery should be configurable to deliver the required amount of particles at the appropriate interval, in order to achieve optimal treatment.

The particles may for example be used for the treatment or prevention of atherosclerosis. Here, perfusion of particles may be done intravenously to stabilize atherosclerotic plaques or reduce inflammation in the plaques. The particles may be used for the treatment or prevention of septic shock by intravenous perfusion.

The particles may be used for the treatment or prevention of heart failure. This may be achieved by chronic intracoronary or intramyocardially perfusion of particles to retard remodeling or retard heart failure. The particles may be used for the treatment or prevention of lung inflammation by intranasal delivery.

The particles may be used for the treatment or prevention of dermatological conditions e.g. psoriasis. Long term delivery of particles may be employed using transdermal microinjection needles until the condition is resolved.

It will be evident that the delivery method will depend on the particular organ to which the particles is to be delivered, and the skilled person will be able to determine which means to employ accordingly.

As an example, in the treatment of cardiac inflammation, the particles may be delivered for example to the cardiac tissue (i.e., myocardium, pericardium, or endocardium) by direct intracoronary injection through the chest wall or using standard percutaneous catheter based methods under fluoroscopic guidance for direct injection into tissue such as the myocardium or infusion of an inhibitor from a stent or catheter which is inserted into a bodily lumen.

Any variety of coronary catheter, or a perfusion catheter, may be used to administer the compound. Alternatively the particles may be coated or impregnated on a stent that is placed in a coronary vessel.

Tissue Regeneration

Mesenchymal stem cells and differentiated cells made according to the methods and compositions described here, and particles derived therefrom, may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Mesenchymal stem cells and differentiated cells and particles derived therefrom may be used for tissue engineering, such as for the growing of skin grafts. Modulation of stem cell differentiation may be used for the bioengineering of artificial organs or tissues, or for prosthetics, such as stents.

Cancer

Mesenchymal stem cells and differentiated cells made by the methods and compositions described here and particles derived therefrom may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

The mesenchymal stem cells and differentiated cells made according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino)benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Obtaining Mesenchymal Stem Cells (MSC)

The particles described here may be isolated or produced from mesenchymal stem cell conditioned medium (MSC-CM). MSCs suitable for use in the production of conditioned media and particles may be made by any method known in the art.

In particular, MSCs may be made by propagating a cell obtained by dispersing a embryonic stem (ES) cell colony, or a descendent thereof, in the absence of co-culture in a serum free medium comprising FGF2. This is described in detail in the sections below.

The prior art methods of obtaining mesenchymal stem cells (MSC) or MSC-like cells from hESCs involve either transfection of a human telomerase reverse transcriptase (hTERT) gene into differentiating hESCs (Xu et al., 2004) or coculture with mouse OP9 cell line (Barberi et al., 2005). The use of exogenous genetic material and mouse cells in these derivation protocols introduces unacceptable risks of tumorigenicity or infection of xenozootic infectious agents.

The particles may therefore be made from MSCs derived by the use of a clinically relevant and reproducible protocol for isolating similar or identical (such as homogenous) MSC populations from differentiating hESCs. In general, the method comprises dispersing a embryonic stem (ES) cell colony into cells. The cells are then plated out and propagated. The cells are propagated in the absence of co-culture in a serum free medium comprising fibroblast growth factor 2 (FGF2), in order to obtain mesenchymal stem cells (MSCs).

Thus, the protocol does not require serum, use of mouse cells or genetic manipulations and requires less manipulations and time, and is therefore highly scalable. The protocol may be used for the isolation of MSCs from two different hESC lines, HuES9 and H-1 and also a third one, Hes-3. Human ES cell derived MSCs (hESC-MSCs) obtained by the methods and compositions described here are remarkably similar to bone-marrow derived MSCs (BM-MSCs).

The embryonic stem cell culture may comprise a human embryonic stem cell (hESC) culture.

In a one embodiment, a method of generating mesenchymal stem cells (MSC) comprises trypsinizing and propagating hESCs without feeder support in media supplemented with FGF2 and optionally PDGF AB before sorting for CD105+CD24− cells.

The method may comprise sorting for CD105+, CD24− cells from trypsinized hESCs one week after feeder-free propagation in a media supplemented with FGF2 and optionally PDGF AB will generate to generate a hESC-MSC cell culture in which at least some, such as substantially all, or all cells are similar or identical (such as homogenous) to each other.

The MSCs produced by this method may be used to produce mesenchymal stem cell conditioned medium (MSC-CM), from which the particles may be isolated.

Disaggregating Embryonic Stem Cell Colonies

One method of producing mesenchymal stem cells may comprise dispersing or disaggregating an embryonic stem cell colony into cells.

The embryonic stem cell colony may comprise a huES9 colony (Cowan Calif., Klimanskaya I, McMahon J, Atienza J, Witmyer J, et al. (2004) *Derivation of embryonic stem-cell lines from human blastocysts*. N Engl J Med 350: 1353-1356) or a H1 ESC colony (Thomson J A, Itskovitz-Eldor J, Shapiro S S, Waknitz M A, Swiergiel J J, et al. (1998) *Embryonic Stem Cell Lines Derived from Human Blastocysts*. Science 282: 1145-1147).

The cells in the colony may be disaggregated or dispersed to a substantial extent, i.e., at least into clumps. The colony may be disaggregated or dispersed to the extent that all the cells in the colony are single, i.e., the colony is completely disaggregated.

The disaggregation may be achieved with a dispersing agent.

The dispersing agent may be anything that is capable of detaching at least some embryonic stem cells in a colony from each other. The dispersing agent may comprise a reagent which disrupts the adhesion between cells in a colony, or between cells and a substrate, or both. The dispersing agent may comprise a protease.

The dispersing agent may comprise trypsin. The treatment with trypsin may last for example for 3 minutes or thereabouts at 37 degrees C. The cells may then be neutralised, centrifuged and resuspended in medium before plating out.

The method may comprise dispersing a confluent plate of human embryonic stem cells with trypsin and plating the cells out.

The disaggregation may comprise at least some of the following sequence of steps: aspiration, rinsing, trypsinization, incubation, dislodging, quenching, re-seeding and aliquoting. The following protocol is adapted from the Hedrick Lab, UC San Diego (http://hedricklab.ucsd.edu/Protocol/COSCell.html).

In the aspiration step, the media is aspirated or generally removed from the vessel, such as a flask. In the rinsing step, the cells are rinsed with a volume, for example 5-10 mls, of a buffered medium, which is may be free from $Ca^{2+}$ and $Mg^{2+}$. For example, the cells may be rinsed with calcium and magnesium free PBS. In the trypsinization step, an amount of dispersing agent in buffer is added to the vessel, and the vessel rolled to coat the growing surface with the dispersing agent solution. For example, 1 ml of trypsin in Hank's BSS may be added to a flask.

In the incubation step, the cells are left for some time at a maintained temperature. For example, the cells may be left at 37° C. for a few minutes (e.g., 2 to 5 minutes). In the dislodging step, the cells may be dislodged by mechanical action, for example by scraping or by whacking the side of the vessel with a hand. The cells should come off in sheets and slide down the surface.

In the quenching step, a volume of medium is added to the flask. The medium may comprise a neutralising agent to stop the action of the dispersing agent. For example, if the dispersing agent is a protease such as trypsin, the medium may contain a protein, such as a serum protein, which will mop up the activity of the protease. In a particular example, 3 ml of serum containing cell culture medium is added to the flask to make up a total of 4 mls. The cells may be pipetted to dislodge or disperse the cells.

In the re-seeding step, the cells are re-seeded into fresh culture vessels and fresh medium added. A number of re-seedings may be made at different split ratios. For example, the cells may be reseeded at 1/15 dilution and 1/5 dilution. In a particular example, the cells may be re-seeded by adding 1 drop of cells into a 25 $cm^2$ flask and 3 drops into another to re-seed the culture, and 7-8 mls media is then added to each to provide for 1/15 dilution and 1/5 dilution from for example a 75 $cm^2$ flask. In the aliquoting step, the cells may be aliquoted into new dishes or whatever split ratio is desired, and media added.

In a specific embodiment, the method includes the following steps: human ES cells are first grown suspended in non-adherent manner to form embryoid bodies (EBs). 5-10 day old EBs are then trypsinized before plating as adherent cells on gelatine coated tissue culture plates.

Maintenance as Cell Culture

The disaggregated cells may be plated and maintained as a cell culture.

The cells may be plated onto a culture vessel or substrate such as a gelatinized plate. Crucially, the cells are grown and propagated without the presence of co-culture, e.g., in the absence of feeder cells.

The cells in the cell culture may be grown in a serum-free medium which is supplemented by one or more growth factors such as fibroblast growth factor 2 (FGF2) and optionally platelet-derived growth factor AB (PDGF AB), at for example 5 ng/ml. The cells in the cell culture may be split or subcultured 1:4 when confluent, by treatment with trypsin, washing and replating.

Absence of Co-Culture

The cells may be cultured in the absence of co-culture. The term "co-culture" refers to a mixture of two or more different kinds of cells that are grown together, for example, stromal feeder cells.

Thus, in typical ES cell culture, the inner surface of the culture dish is usually coated with a feeder layer of mouse embryonic skin cells that have been treated so they will not divide. The feeder layer provides an adherent surface to enable the ES cells to attach and grow. In addition, the feeder cells release nutrients into the culture medium which are required for ES cell growth. In the methods and compositions described here, the ES and MSC cells may be cultured in the absence of such co-culture.

The cells may be cultured as a monolayer or in the absence of feeder cells. The embryonic stem cells may be cultured in the absence of feeder cells to establish mesenchymal stem cells (MSC).

The dissociated or disaggregated embryonic stem cells may be plated directly onto a culture substrate. The culture substrate may comprise a tissue culture vessel, such as a Petri dish. The vessel may be pre-treated. The cells may be plated onto, and grow on, a gelatinised tissue culture plate.

An example protocol for the gelatin coating of dishes follows. A solution of 0.1% gelatin in distilled water is made and autoclaved. This may be stored at room temp. The bottom of a tissue culture dish is covered with the gelatin solution and incubated for 5-15 min. Remove gelatin and plates are ready to use. Medium should be added before adding cells to prevent hypotonic lysis.

Serum Free Media

The dissociated or disaggregated embryonic stem cells may be cultured in a medium which may comprise a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may comprise or be supplemented with 10% serum replacement media from Invitrogen-Gibco (Grand Island, N.Y.).

Growth Factor

The serum-free medium in which the dissociated or disaggregated embryonic stem cells are cultured may comprise one or more growth factors. A number of growth factors are known in the art, including PDGF, EGF, TGF-a, FGF, NGF, Erythropoietin, TGF-b, IGF-I and IGF-II.

The growth factor may comprise fibroblast growth factor 2 (FGF2). The medium may also contain other growth factors such as platelet-derived growth factor AB (PDGF AB). Both of these growth factors are known in the art. The method may comprise culturing cells in a medium comprising both FGF2 and PDGF AB.

Alternatively, or in addition, the medium may comprise or further comprise epidermal growth factor (EGF). Use of EGF may enhance growth of MSCs. EGF may be used at any suitable concentration, for example 5-10 ng/ml EGF. EGF may be used in place of PDGF. EGF is a protein well known in the art, and is referred to as symbol EGF, Alt. Symbols URG, Entrez 1950, HUGO 3229, OMIM 131530, RefSeq NM_001963, UniProt P01133.

Thus, we disclose the use of media comprising (i) FGF2, (ii) FGF2 and PDGF and (iii) FGF2 and EGF and other combinations.

FGF2 is a wide-spectrum mitogenic, angiogenic, and neurotrophic factor that is expressed at low levels in many tissues and cell types and reaches high concentrations in brain and pituitary. FGF2 has been implicated in a multitude of physiologic and pathologic processes, including limb development, angiogenesis, wound healing, and tumor growth. FGF2 may be obtained commercially, for example from Invitrogen-Gibco (Grand Island, N.Y.).

Platelet Derived Growth Factor (PDGF) is a potent mitogen for a wide range of cell types including fibroblasts, smooth muscle and connective tissue. PDGF, which is composed of a dimer of two chains termed the A chain and B chain, can be present as AA or BB homodimers or as an AB heterodimer. Human PDGF-AB is a 25.5 kDa homodimer protein consisting of 13.3 kDa A chain and 12.2 B chain. PDGF AB may be obtained commercially, for example from Peprotech (Rocky Hill, N.J.).

The growth factor(s), such as FGF2 and optionally PDGF AB, may be present in the medium at concentrations of about 100 pg/ml, such as about 500 pg/ml, such as about 1 ng/ml, such as about 2 ng/ml, such as about 3 ng/ml, such as about 4 ng/ml, such as about 5 ng/ml. In some embodiments, the medium contains FGF2 at about 5 ng/ml. The medium may also contain PDGF AB, such as at about 5 ng/ml.

Splitting Cells

Cells in culture will generally continue growing until confluence, when contact inhibition causes cessation of cell division and growth. Such cells may then be dissociated from the substrate or flask, and "split", subcultured or passaged, by dilution into tissue culture medium and replating.

The methods and compositions described here may therefore comprise passaging, or splitting during culture. The cells in the cell culture may be split at a ratio of 1:2 or more, such as 1:3, such as 1:4, 1:5 or more. The term "passage" designates the process consisting in taking an aliquot of a confluent culture of a cell line, in inoculating into fresh medium, and in culturing the line until confluence or saturation is obtained.

Selection, Screening or Sorting Step

The method may further comprise a selection or sorting step, to further isolate or select for mesenchymal stem cells.

The selection or sorting step may comprise selecting mesenchymal stem cells (MSC) from the cell culture by means of one or more surface antigen markers. The use of a selection or sorting step further enhances the stringency of sorting and selection specificity for MSCs and furthermore potentially reduces possible contamination from embryonic stem cells such as hESCs and other hESC-derivatives from the starting material. This would then further reduce the risk of teratoma formation and further increase the clinical relevance of the protocol we describe.

A number of methods are known for selection or sorting based on antigen expression, and any of these may be used in the selection or sorting step described here. The selection or sorting may be achieved by means of fluorescence activated cell sorting (FACS). Thus, as known in the art, FACS involves exposing cells to a reporter, such as a labelled antibody, which binds to and labels antigens expressed by the cell. Methods of production of antibodies and labelling thereof to form reporters are known in the art, and described for example in Harlow and Lane. The cells are then passed through a FACS machine, which sorts the cells from each other based on the labelling. Alternatively or in addition, magnetic cell sorting (MACS) may be employed to sort the cells.

We have realised that while a number of candidate surface antigens known to be associated with MSCs e.g. CD105, CD73, ANPEP, ITGA4 (CD49d), PDGFRA, some of the MSC associated surface antigens e.g. CD29 and CD49e are also highly expressed in ES cells such as hESCs and their expression are verified by FACS analysis. The association of a surface antigen with MSCs may not be sufficient to qualify the antigen as a selectable marker for isolating MSCs from ES cells such as hESC. Accordingly, the selection or sorting step may employ antigens which are differentially expressed between MSCs and ES cells.

The selection or sorting step of our method may positively select for mesenchymal stem cells based on the expression of antigens. Such antigens may be identified by, for example, comparing the gene expression profiles of hESCs and hESC-MSCs. In particular embodiments, the selection or sorting may specifically make use of any of the antigens shown in Table E1A and E1B below.

The selection or sorting step of our method may positively select for mesenchymal stem cells based on the expression of antigens which are identified as expressed on MSCs, but not expressed on ES cells such as hESCs.

CD73 is highly expressed on MSCs, while being not highly expressed on hESCs. Both CD73 and CD105 are highly expressed surface antigens in MSCs and are among the top 20 highly expressed surface antigens in hESC-MSCs relative to hESC, the use of either CD73 or CD105 (or both) as selectable marker for putative MSCs will be equally effective in sorting for putative MSCs generated by differentiating hESCs.

Alternatively, or in addition, the selection or sorting step may negatively select against antigens based on surface antigens that are highly expressed as surface antigen on embryonic stem cells (ES cells) such as hESCs, and not mesenchymal stem cells e.g., hESC-MSC. Selection or sorting may be based on known or previously identified hESC-specific surface antigens such as MIBP, ITGB1BP3 and PODXL, and CD24.

FACS analysis confirms the expression of CD24 on hESC but not hESC-MSCs. Therefore, CD24 may be used as a negative selection or sorting marker either on its own, or in conjunction with CD105 as a positive selectable marker for isolating putative MSCs from differentiating hESC cultures.

EXAMPLES

Mesenchymal stem cells (MSCs) derived from adult bone marrow have emerged as one of the most promising stem cell types for treating cardiovascular disease (Pittenger and Martin, 2004). Although the therapeutic effects of autologous MSCs have been attributed to their potential to differentiate into many different reparative or replacement cell types such as cardiomyocytes, endothelial cells and vascular smooth cells (Minguell and Erices, 2006; Zimmet and Hare, 2005), the differentiation efficiency of transplanted MSCs into therapeutically relevant numbers of functional reparative cells in injured tissues remains to be established.

Recent reports suggest that some of these reparative effects are mediated by paracrine factors secreted by MSCs (Caplan and Dennis, 2006a; Gnecchi et al., 2005; Gnecchi et al., 2006; Schafer and Northoff, 2008). This paracrine hypothesis introduces a radically different dimension to the use of stem cells, particularly MSCs, in regenerative medicine. Potential mechanisms of MSC paracrine actions include endogenous regenerative capacity, angio- and arteriogenesis, attenuating remodeling, and reducing apoptosis. If the therapeutic effects of MSCs are partly mediated by their secretions, the repertoire of stem cell-based therapies could be extended by application of their secreted factors. Such an approach could potentially provide an "off-the-shelf" MSC-based therapeutic option, which is a requisite for time-sensitive protection against reperfusion injury in patients with acute MI, at affordable costs and with excellent quality control and consistency.

In support of this paracrine hypothesis, many studies have identified the presence of cytokines, chemokines and growth factors that could potentially repair injured cardiac tissues mainly through cardiac and vascular tissue growth and regeneration (Caplan and Dennis, 2006b; Liu and Hwang, 2005). We further supported this hypothesis by performing the first in-depth proteomic analysis of the MSC paracrine secretion (Sze et al., 2007). This was facilitated by our derivation of highly expandable and identical MSC cultures from human ESCs (Lian et al., 2007) and the use of a chemically defined medium to culture the cells and harvest the secretion via the conditioned medium (CM). Surprisingly, many of the secreted proteins were intracellular proteins and are not known to be secreted or transported across plasma membrane. Computational analysis of the secretome predicted that collectively, the secretome has the potential to repair injured tissues such as myocardial ischemia/reperfusion (MI/R) injury (Sze et al., 2007).

To test the computational prediction, the secretion in the form of CM was administered to a pig model of MI/R injury (Timmers et al., 2008). During myocardial ischemia caused by occlusion of a coronary artery, reperfusion therapy is currently the most effective treatment modality. However, reperfusion which involves the opening of the blocked artery to restore blood flow or reperfusion also induces injury to the newly perfused ischemic tissues (Saraste et al., 1997). Therefore the effectiveness of reperfusion therapy could be greatly improved if reperfusion injury could be neutralized immediately at the point of reperfusion. When the CM was delivered intra-coronary to the pig model of MI/R injury immediately after reperfusion, there was a 60% reduction in myocardial infarction, preservation of cardiac function and reduced oxidative stress as early as 4 hours after reperfusion. This confirmed that the paracrine secretion of MSC can ameliorate MI/R injury in a clinically relevant animal model (Timmers et al., 2008).

However, the mechanism by which the secretion mediates this immediate effect on MI/R injury is not clear. It is obvious that the immediacy of this protective effect precludes the relatively lengthy process of tissue regeneration as part of the mechanism. Also, many of the secreted proteins are intracellular proteins and are not known to cross plasma membranes readily. To better understand the paracrine effects of MSCs, we systematically fractionated the CM using membranes with different molecular weights cut-off (MWCO) to identify and profile the composition of the active fraction. We previously showed that CM filtered through 0.2 μM membrane but not 1000 kDa MWCO was cardioprotective (Timmers et al., 2008). However, CM partially concentrated against membrane with 1000 kDa MWCO was cardioprotective. This suggested that the cardioprotective effect was mediated by large complexes with diameter of 50–100 nm.

Here we extended our previously reported list of proteins in the secretion to >700 proteins and these proteins include many proteins that are commonly found in exosomes. We also identified the presence of RNA (<300 nts) in the secretion. Furthermore, the proteins and RNA were encapsulated in phospholipid vesicles and the only detectable particles in the secretion within the hydrodynamic radius ($r_h$) range of 1-1000 nm were of $r_h$=45-55 nm. These particles eluted as a single peak on HPLC fractionation. Together, these studies demonstrate that the large cardioprotective complex in the secretion carry many of the distinctive feature of an exosome leading to our hypothesis that the active cardioprotective component in the secretion is an exosome.

Example 1

Materials and Methods: MSC-CM Preparation

The protocols for MSC generation and CM preparation have been described previously[15, 16].

In short, a chemically defined serum free culture medium is conditioned by MSCs derived from human embryonic stem cells (hESCs), using a clinically compliant protocol. Three polyclonal, karyotypically stable, and phenotypically MSC-like cultures, that do not express pluripotency-associated markers but displayed MSC-like surface antigens (CD29+, CD44+, CD49a+/e+, CD105+, CD166+, CD34−, CD45−) and gene expression profile, are generated by trypsinization and propagation of hESCs from either HuES9 hESC line or H1 hESC line in feeder- and serum-free selection media[15].

One of these cultures, HuES9.E1 can be stably expanded for at least 80 population doublings. To harvest MSC secretion, hESC-derived MSC cultures are transferred to a chemically defined, serum free culture medium to condition the medium for three days before the media containing MSC secretions are collected, clarified by centrifugation, concentrated 25 times using 10 kDa MW cut-off ultrafiltration membranes and sterilized by filtration through a 220 nm filter.

The secretory proteome is analyzed by multidimensional protein identification technology (MuDPIT) and cytokine antibody array analysis, and revealed the presence of 201 unique gene products. Computational analyses disclosed that this CM holds potential cytoprotective properties[16].

Example 2

Materials and Methods: Animals

All experiments are performed in accordance with the "Guide for the Care and Use of Laboratory Pigs" prepared by the Institute of Laboratory Animal Resources and with prior approval by the Animal Experimentation Committee of the Faculty of Medicine, Utrecht University, the Netherlands.

Example 3

Materials and Methods: Study Design

Thirty female Dalland Landrace pigs (60-70 kg; IDDLO, Lelystad, The Netherlands), all pretreated with clopidogrel 75 mg/day for 3 days and amiodarone 400 mg/day for 10 days, are randomly assigned to MSC-CM, non-CM, or saline treatment.

The saline group is added to assess a potential effect of fresh, non-conditioned culture medium. In all pigs, MI is induced by 75 minutes of proximal left circumflex coronary artery (LCxCA) ligation and 4 hours of subsequent reperfusion. An ischemic period of 75 minutes is selected to inflict severe myocardial injury without inducing completely transmural myocardial infarction. The 4 hour reperfusion period is used, because infarct size measurement using TTC staining is most reliable after 3 hours of reperfusion[17]. After longer periods of reperfusion, it becomes more difficult to assess oxidative stress status and apoptotic mechanisms.

Treatment is initiated 5 minutes before the onset of reperfusion by intravenous infusion of MSC-CM (1.0 ml, 2.0 mg protein) non-CM or saline. Immediately following reperfusion, an additional intracoronary bolus MSC-CM (4.0 ml, 8.0 mg protein), non-CM or saline is given. Myocardial infarct size and function are assessed 4 hours after reperfusion.

Example 4

Materials and Methods: MI and Operational Procedure

During the entire operation, ECG, Systemic Arterial Pressure, and capnogram are monitored continuously. Under general anesthesia as described before[18], a median sternotomy is performed and two introduction sheets are inserted in the carotid arteries for a 6 Fr guiding catheter and an 8 Fr conductance catheter (CD Leycom, Zoetermeer, the Netherlands).

The distal tip of a Swan Ganz catheter is placed into the pulmonary artery via the internal jugular vein. Transonic flow probes (Transonic Systems Inc, Ithaca, N.Y.) are placed around the proximal aorta and LCxCA to measure cardiac output and coronary flow, and a wire is placed around the inferior caval vein to enable functional measurements under varying loading conditions for PV loops.

After functional measurements, 10.000 IU of heparin are administered intravenously and sutures are tightened to occlude the proximal LCxCA. Internal defibrillation with 50 J is used when ventricular fibrillation occurred. After 75 minutes of ischemia, the LCxCA is reopened by release of the suture. Immediately following reperfusion, Nitroglycerine (0.1 mg to prevent no-reflow) is infused through the LCxCA via the guiding catheter, followed by intracoronary treatment with MSC-CM, non-CM or saline. After 4 hours of reperfusion, the final functional measurements are performed and the heart is explanted for infarct size analysis.

Example 5

Materials and Methods: Functional Measurements

Left ventricular (LV) pressure and volume are measured using the conductance catheter method, as described previously[18]. LV pressure and volume signals derived from the conductance catheter are displayed and acquired at a 250-Hz sampling rate with a Leycom CFL-512 (CD Leycom).

Data are acquired during steady state and during temporal caval vein occlusion, all with the ventilator turned off at end expiration. Analysis of the pressure-volume loops is performed with custom software as described previously[19]. In addition, short-axis epicardial ultrasound images (Prosound SSD-5000, 5-MHz probe UST-5280-5, Aloka Holding Europe AG, Zug, Switzerland) are obtained at the midpapillary muscle level. Wall thickness (WT) of the infarct area, remote area (septum) and LV internal area (LVia) are measured at end diastole (ED) and end systole (ES). Systolic wall thickening (SWT) is calculated as [(WT(ES)−WT(ED))/WT(ED)]*100%, fractional area shortening (FAS) as [(LVia(ES)−LVia (ED))/LVia (ED)]*100%, and left ventricular ejection fraction (LVEF) as [(EDV−ESV)/EDV] *100%.

The end-diastolic chamber stiffness is quantified by means of linear regression of the end-diastolic pressure-volume relationship. Echocardiography and PV loops are measured before MI, 1 hour after ischemia and 4 hours after reperfusion. To challenge stunned myocardium, additional measurements are performed during pharmaceutically induced stress by intravenous dobutamine infusion (2.5 µg/kg/min and 5.0 µg/kg/min).

Example 6

Materials and Methods: Infarct Size

Just prior to excision of the heart, the LCxCA (pigs) or LCA (mice) is religated at exactly the same spot as for the induction of the MI. Evans blue dye is infused through the coronary system to delineate the area at risk (AAR).

The heart is then excised, the LV is isolated and cut into 5 slices from apex to base. The slices are incubated in 1% triphenyltetrazolium chloride (TTC, Sigma-Aldrich Chemicals, Zwijndrecht, the Netherlands) in 37° C. Sorensen buffer (13.6 g/L $KH_2PO_4$+17.8 g/L $Na_2H\ PO_4.2H_2O$, pH 7.4) for 15 minutes to discriminate infarct tissue from viable myocardium.

All slices are scanned from both sides, and in each slide, the infarct area is compared with area at risk and the total area by use of digital planimetry software (Image J). After correction for the weight of the slices, infarct size is calculated as a percentage of the AAR and of the LV.

Example 7

Materials and Methods: Oxidation Induced Cell Death Assay

Human leukemic CEM cells are incubated in either CM or non-CM, and treated with 50 µM $H_2O_2$ to induce oxidative stress. Cell viability is assessed using Trypan Blue exclusion at 12, 24, 36 and 48 hours after $H_2O_2$ treatment.

Example 8

Materials and Methods: Immunostaining

Nuclear oxidative stress in the ischemia and reperfusion area is assessed by immunostaining for 8-hydroxy-2'-deoxyguanosine (8-OHdG), a product of oxidative stress to DNA. Tissue samples are fixed in 4% formalin before being embedded in paraffin. Following antigen retrieval in 10 mM citric acid, the tissue sections are incubated with 10% normal horse serum for 30 minutes, mouse-anti-8-OHdG (OXIS international, Foster City, Calif., USA) 1:20 in 0.1% PBSA over night at 4° C., biotin labeled horse-anti-mouse (Vector laboratories, Burlingame, Calif., USA) 1:500 for 1 hour and with streptavidin-HRPO 1:1000 for 1 hour.

Finally, the sections are incubated with $H_2O_2$-diaminobenzidine for 10 minutes. The amount of 8-OHdG positive nuclei is quantified in 4 randomly picked fields per section with digital image microscopy software Analysis (Olympus, Munster, Germany) at 200× magnification.

Example 9

Materials and Methods: Western Blotting

Protein is isolated from frozen tissue samples collected from the ischemia/reperfusion area of pigs using 1 ml Tripure Isolation Reagent (Boehringer, Mannheim, Germany) according to the manufacturer's protocol. For western blotting, 8 µg total protein is separated on a 10% SDS-PAGE gel, transferred onto a Nitrocellulose C membrane (Amersham, Buckinghamshire, UK) and blocked using Phosphate Buffered Saline (PBS)-0.1% Tween-5% Protifar (Nutricia, Netherlands).

The membrane is incubated with a rabbit antibody for phosphoSMAD2 1:1000 (Cell Signalling Technology), for active caspase 3 1:100 (Chemicon, Germany), or for beta-tubulin 1:5000 (Abcam, Cambridge, UK), and subsequently with goat-anti-rabbit HRP 1:2000 (DAKO, Glostrup, Denmark). Chemiluminescence substrate (NENk Life Science Products) is used for detection; the bands are analyzed using the Gel Doc 1000 system (Biorad, Veenendaal, Netherlands).

Example 10

Materials and Methods: MSC-CM Fractionation

The MSC-CM is prepared by sterile filtration through a 220 nm filter and concentrated through a 10 nm filter and therefore contains components between 10 and 220 nm. Subsequently, a <1000 kDa fraction is prepared by filtering the MSC-CM through a 1000 kDa MW cut-off membrane with a 100 nm nominal pore size (Pall Corporation, Singapore), generating a fraction containing products between 10 and 100 nm.

To identify the fraction containing the factor(s) within the medium that confers cardioprotection (10-100 nm or 100-220 nm), a mouse or pig model of ischemia and reperfusion injury is used. MI is induced by 30 minutes left coronary artery (LCA) occlusion and subsequent reperfusion. Mice are treated with 20 µl unfractionated MSC-CM (10-220 nm), the <1000 kDa fraction (10-100 nm), or saline intravenously via the tail vein, 5 minutes before reperfusion. Infarct size is assessed 24 hours later using Evans blue and TTC as described previously.

Example 11

Materials and Methods: Data Analysis

Data are presented as mean±SEM. Values are collected in a blinded fashion and compared using one-way ANOVA with post hoc bonferroni tests in SPSS 11.5. P-value<0.05 is considered significant.

Example 12

Results: Mortality

Four pigs died due to refractory ventricular fibrillation during the ischemia, before treatment, and are therefore excluded from the study. All pigs that are treated with CM (n=9), non-CM (n=9) or saline (n=8) also survived the follow up period.

Example 13

Results: Infarction Size

Infarct size, compared to the area at risk (AAR) as well as compared to the LV, is markedly reduced in pigs treated with MSC-CM compared to those treated with non-CM and saline (FIG. 1). MSC-CM treatment resulted in approximately 60% reduction of infarct size. Importantly, the AAR is similar in all pigs, which indicates that the initial ischemic injury is similar in all pigs (Table E1 below).

TABLE E1

Hemodynamic and Functional Parameters. Baseline values and myocardial infarction values of pigs treated with non-CM, CM or saline, determined with echocardiography and conductance catheters based LV pressure and volume measurements.

| parameter | baseline | | | myocardial infarction | | |
|---|---|---|---|---|---|---|
| | non-CM | CM | Saline | non-CM | CM | Saline |
| AAR | — | — | — | 35.1 ± 2.9 | 30.7 ± 1.6 | 32.4 ± 2.3 |
| IS (% of AAR) | — | — | — | 62.2 ± 5.0 | 25.4 ± 4.8 †‡ | 62.5 ± 8.4 |
| IS (% of LV) | — | — | — | 22.3 ± 2.9 | 7.6 ± 1.4 †‡ | 20.5 ± 3.1 |
| HR, bpm | 83.5 ± 5.5 | 76.4 ± 5.7 | 77.6 ± 8.1 | 111.6 ± 6.3 * | 86 ± 7.5 † | 97 ± 5.5 |
| MAP, mmHg | 93.7 ± 10.2 | 94.0 ± 5.4 | 100.9 ± 4.9 | 70.8 ± 9.1 * | 95.8 ± 4.3 ‡ | 68.5 ± 7.3 * |
| QLCx, ml/min | 31.9 ± 2.8 | 28.7 ± 2.9 | 28.4 ± 4.1 | 29.9 ± 2.6 | 25.1 ± 2.6 | 25.6 ± 3.3 |
| CO, l/min | 3.60 ± 0.14 | 3.25 ± 0.17 | 3.79 ± 0.23 | 2.61 ± 0.35 * | 3.15 ± 0.27 ‡ | 2.04 ± 0.20 * |
| WT infarct, cm | 0.71 ± 0.04 | 0.64 ± 0.04 | 0.71 ± 0.03 | 1.23 ± 0.09 * | 0.93 ± 0.09 *‡ | 1.30 ± 0.09 * |
| SWT infarct, % | 56.3 ± 5.6 | 56.9 ± 4.8 | 61.8 ± 4.3 | −6.1 ± 1.4 * | 18.7 ± 4.1 *†‡ | −7.0 ± 1.5 * |
| SWT remote, % | 43.1 ± 3.3 | 43.0 ± 3.0 | 40.9 ± 4.2 | 43.7 ± 7.4 | 41.4 ± 6.1 | 37.8 ± 4.4 |
| FAS, % | 42.7 ± 2.9 | 38.8 ± 2.9 | 41.3 ± 2.7 | 24.7 ± 2.6 * | 36.5 ± 2.0 †‡ | 21.7 ± 1.2 * |
| EDV, ml | 90.3 ± 8.2 | 86.2 ± 9.1 | 101.5 ± 7.1 | 70.2 ± 8.3 | 69.7 ± 5.2 * | 69.1 ± 11.6 |
| ESV, ml | 47.8 ± 8.2 | 43.9 ± 6.2 | 53.0 ± 4.7 | 44.2 ± 6.0 | 31.4 ± 1.4 * | 47.5 ± 9.6 |
| SV, ml | 44.5 ± 3.2 | 43.3 ± 5.0 | 49.6 ± 3.6 | 24.5 ± 4.0 * | 38.5 ± 4.2 †‡ | 21.9 ± 2.7 * |
| EF, % | 52.5 ± 5.0 | 51.7 ± 3.1 | 49.0 ± 2.7 | 38.8 ± 3.5 * | 54.2 ± 2.6 †‡ | 34.7 ± 4.4 * |
| dP/dtmax, mmHg/s | 1290 ± 118 | 1093 ± 83 | 1299 ± 76 | 1592 ± 226 | 1528 ± 130 | 1075 ± 68 * |
| dP/dtmin, mmHg/s | −1614 ± 143 | −1329 ± 113 | −1650 ± 89 | −983 ± 130 * | −1031 ± 116 * | −910 ± 102 * |
| Stiffness, mmHg/ml | 0.13 ± 0.03 | 0.15 ± 0.03 | 0.14 ± 0.01 | 0.29 ± 0.06 * | 0.13 ± 0.01 †‡ | 0.29 ± 0.05 * |

AAR indicates area at risk; IS, infarct size; LV, left ventricle; HR, heart rate; QLCx, left circumflex coronary artery flow; CO, cardiac output; WT, wall thickness; SWT, systolic wall thickening; FAS, fractional area shortening; EDV, end-diastolic volume; ESV, end-systolic volume; SV, stroke volume; EF, ejection fraction; Ees, end-systolic elastance. Non-CM, n = 9; CM, n = 9; saline, n = 8.
* $p < 0.05$ vs. baseline;
† $p < 0.05$ vs. non-CM;
‡ $p < 0.05$ vs. saline.

Example 14

Results: Cardiac Function

Figure 2A:
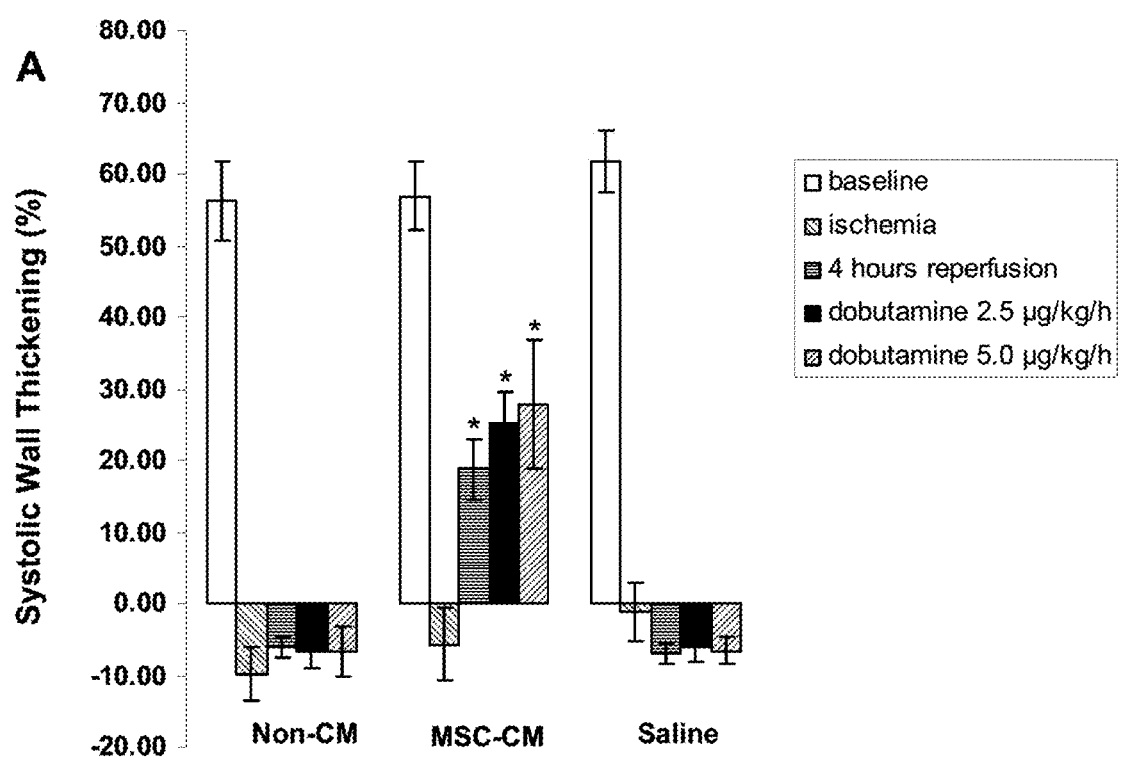
FIGS. 2A-2B show Local and Global systolic function. Local systolic wall thickening as assessed with echocardiography of the infarct area in pigs treated with Non-CM, CM or saline (FIG. 2A). Global systolic function, echocardiographic fractional area shortening (FAS) is shown in FIG. 2B. Non-CM, n=9; CM, n=9; saline, n=8. $*p<0.05$ vs. Non-CM and saline.

Baseline parameters are similar in all groups (Table E1 above). During ischemia, the posterolateral wall became completely dyskinetic in all groups, as is observed by negative values of echocardiographic systolic wall thickening (SWT, FIG. 2A). Four hours after reperfusion, the reperfused posterolateral wall of both non-CM and saline control groups, is still dyskinetic. In the pigs treated with MCS-CM, however, SWT partly recovered (FIG. 2A).

Figure 2B:
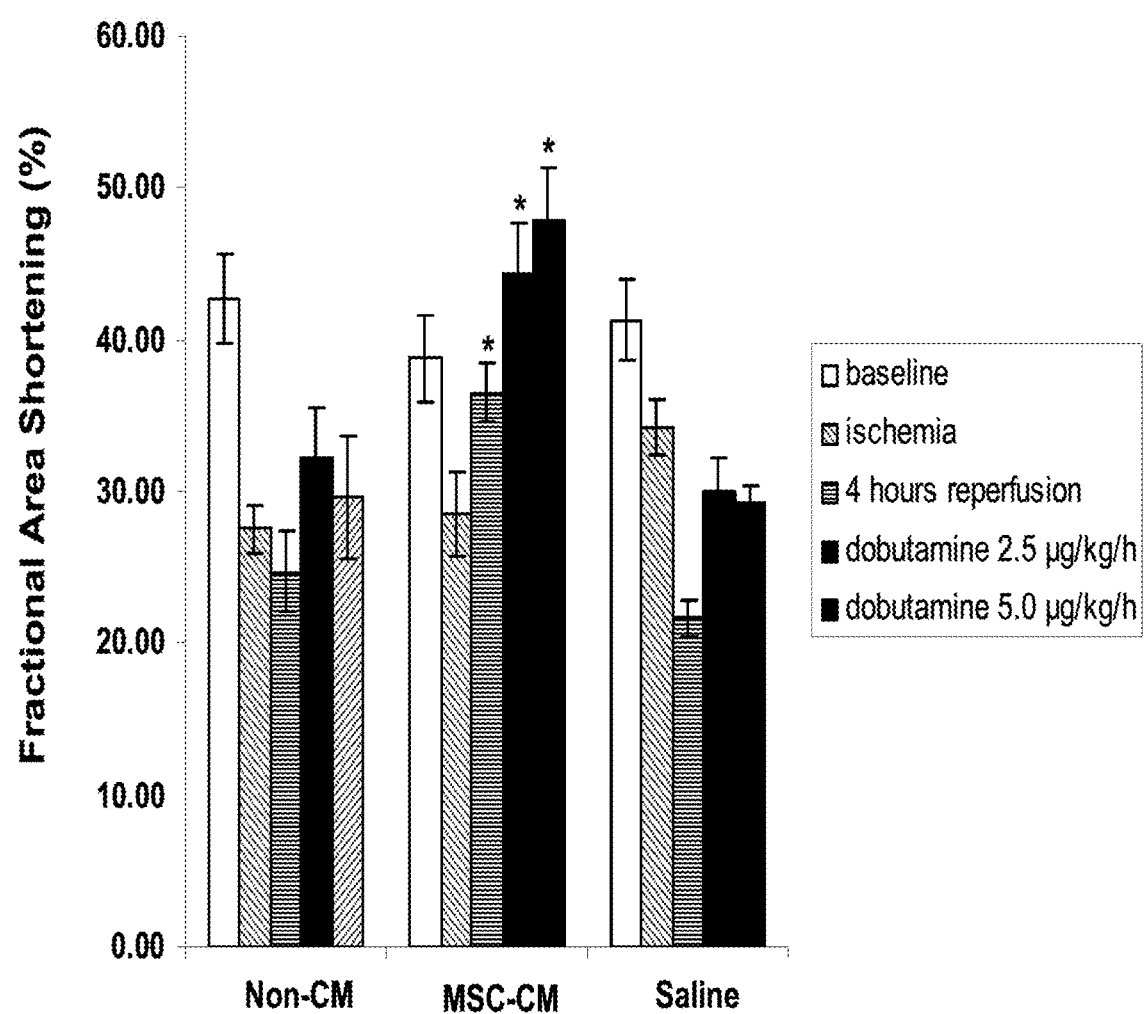

Intravenous infusion of the $\beta_1$-adrenergic receptor agonist dobutamine further increased systolic wall thickening in the MCS-CM treated pigs, whereas no improvement is seen in the control groups. Also global left ventricular systolic function decreased due to the ischemia (FIG. 2B). In the pigs treated with CM, the fractional area shortening increased after reperfusion, almost back to the baseline level, and increased above baseline level during dobutamine infusion.

In control pigs, global systolic function remained impaired. Improved cardiac function also became evident from the PV-loop derived indices (Table E1). Left ventricular EF and stroke volume are significantly higher in CM treated pigs. This translated into improved hemodynamic parameters such as cardiac output, mean arterial pressure and heart rate.

Diastolic function decreased in control groups following ischemia and reperfusion injury, as observed by increased end-diastolic myocardial stiffness. In the CM treated pigs however diastolic function is not impaired.

Example 15

Results: Oxidative Stress

Having demonstrated the reduction in infarct size and improvement of function, we used an in vitro assay of hydrogen peroxide ($H_2O_2$)-induced cell death to determine the effects of CM and non-CM on oxidative stress, a major cause of ischemia reperfusion injury.

Figure 3A:
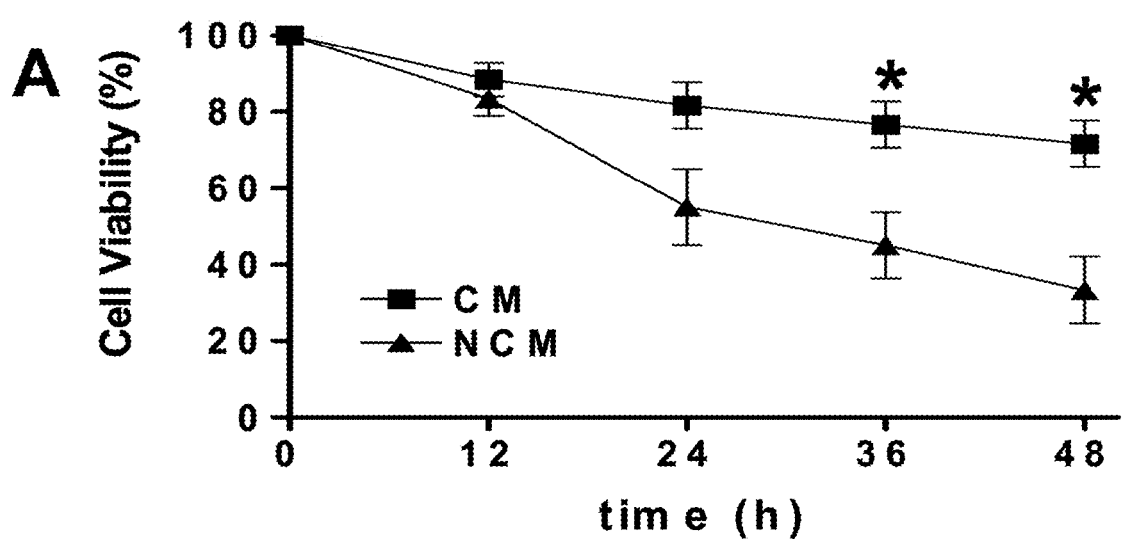
FIGS. 3A-3E show Oxidative Stress. Viability of CEM cells in either CM or Non-CM and treated with $H_2O_2$. ($*p<0.05$, FIG. 3A). Conditioned medium protects cells from death induced by $H_2O_2$. To assess oxidative stress in vivo, infarct area sections from pigs treated with Non-CM (FIG. 3B), CM (FIG. 3C), or saline (FIG. 3D) were stained for 8-OHdG, a product of nuclear oxidative stress. Quantification of 8-OHdG positive nuclei was assessed at 200× magnification and is depicted in FIG. 3E. Also in vivo, CM reduces oxidative stress. Non-CM, n=9; CM, n=9; saline, n=8.

We induced hydrogen peroxide ($H_2O_2$)-mediated oxidative stress in human leukemic CEM cells in the presence of either CM or non-CM and monitored cell viability by Trypan blue-exclusion. Results showed that CM significantly protected against ($H_2O_2$)-induced loss of cell viability compared to non-CM ($p<0.05$) (FIG. 3A).

Figure 3B:
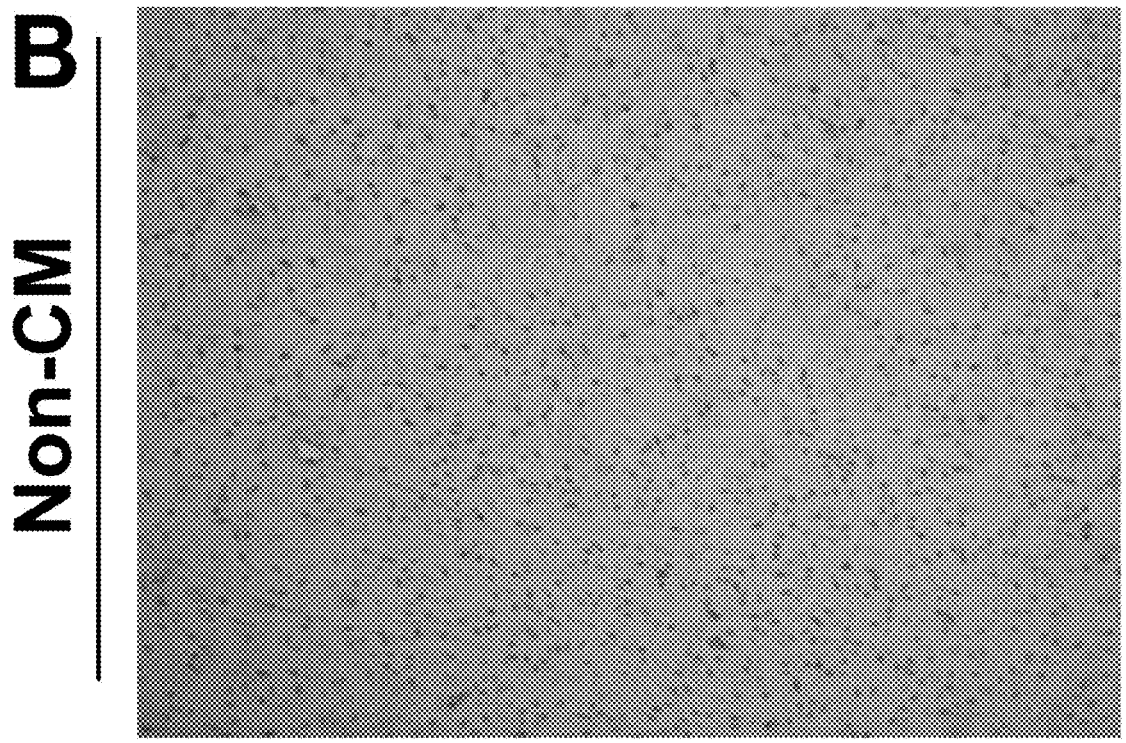
Figure 3C:
Figure 3D:
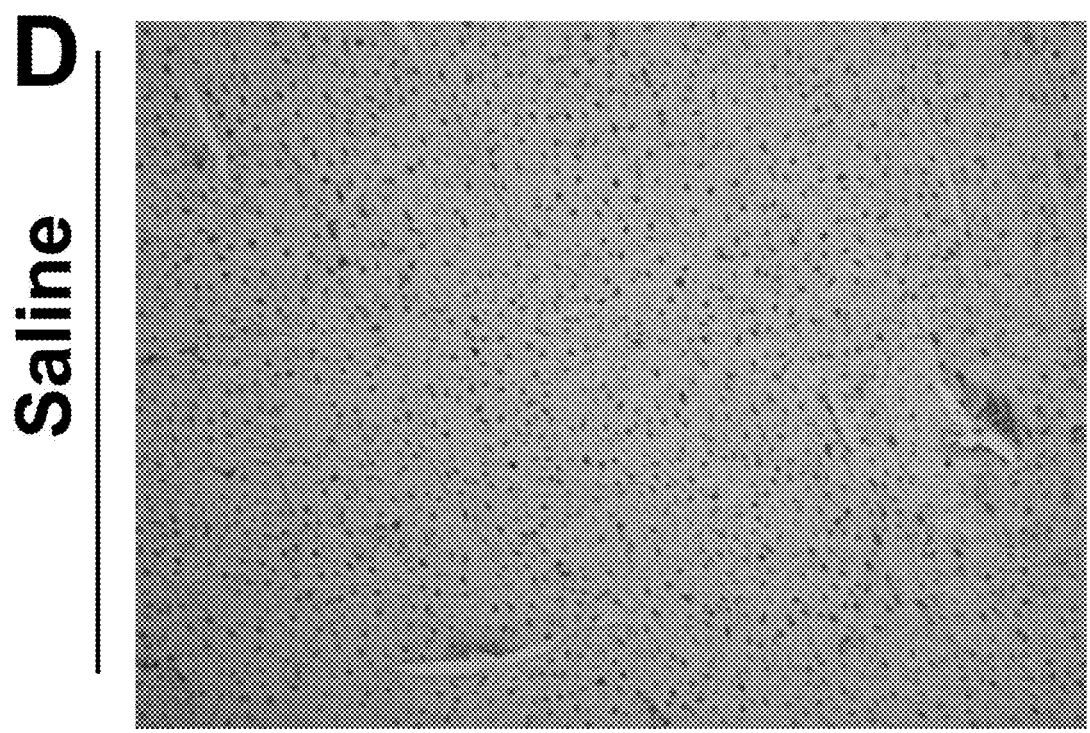
Figure 3E:
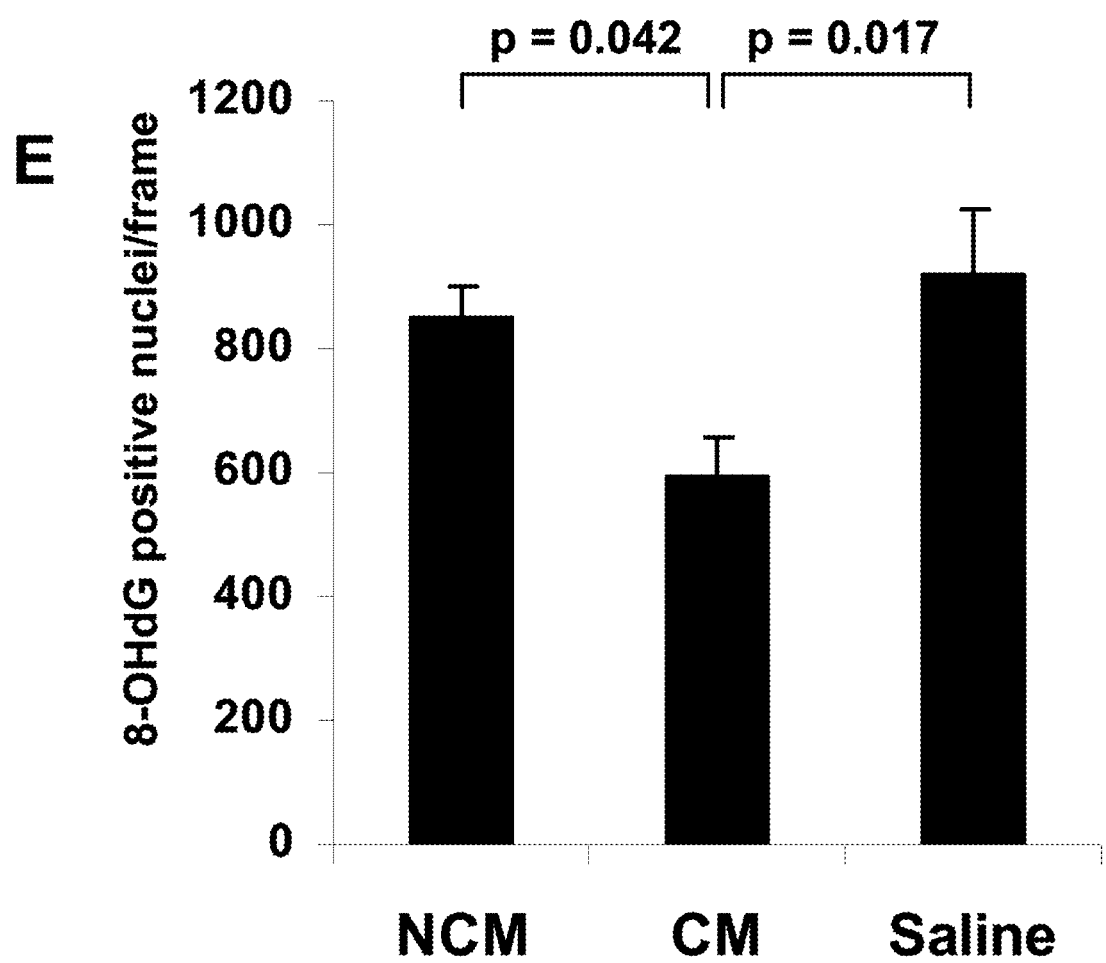

To determine if CM also reduces oxidative stress in the hearts of CM-treated pigs, nuclear oxidative stress in tissue sections of pigs treated with CM, non-CM or saline is quantified by 8-OHdG immunostaining for oxidized DNA. Intense nuclear staining indicative of DNA oxidation is observed in sections of non-CM or saline-treated pigs compared to CM-treated pigs (FIGS. 3B-D). In addition, there are also significantly more positive nuclei in non-CM or saline-treated pigs (FIG. 3E).

Therefore, CM can confer cytoprotection against oxidative stress in vitro and in vivo.

Example 16

Results: TGF-β Signaling

Figure 4A:
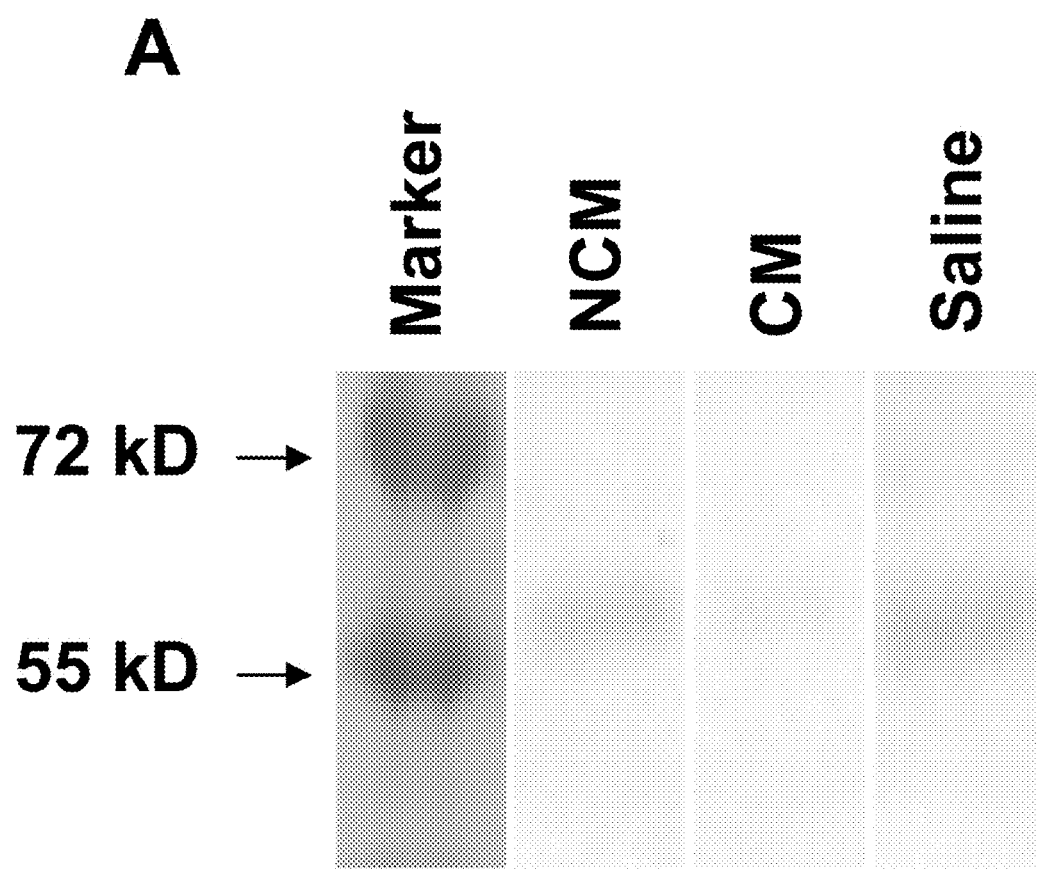
FIGS. 4A-4E show TGF-β Signaling and Apoptosis. Western blot for phosphorylated SMAD 2 (FIG. 4A, FIG. 4B) and active caspase 3 (FIG. 4C, FIG. 4D) in pigs treated with non-CM, CM or saline. Beta-tubulin was assessed as a loading control, and no differences were found in beta-tubulin expression between the groups (FIG. 4E). Non-CM, n=9; CM, n=9; saline, n=8.
Figure 4B:
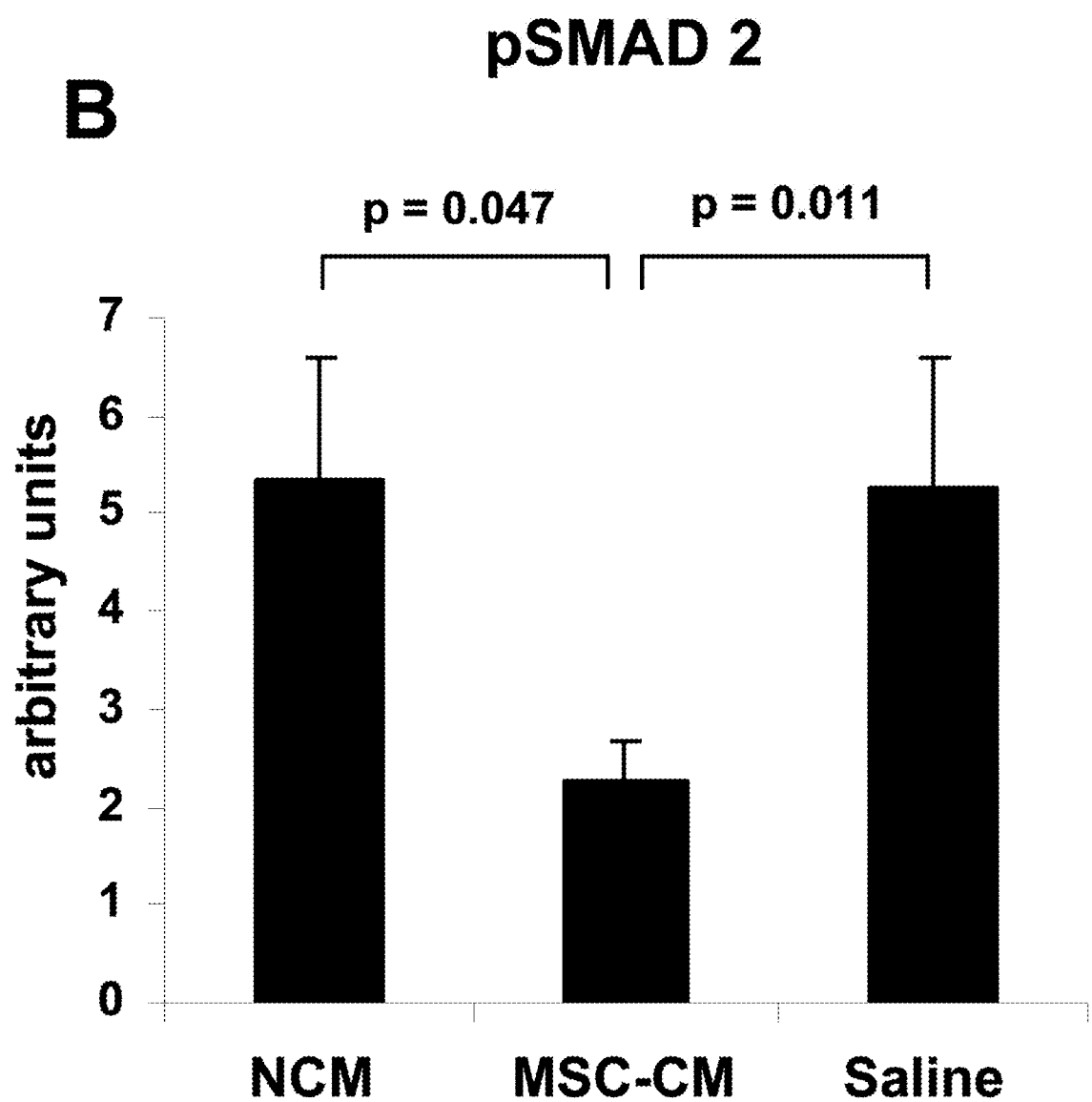

The secretions of the MSCs contained many proteins involved in TGF-β signaling[16]. To assess the influence of CM treatment on TGF-β signaling in vivo, we quantified phosphorylated SMAD-2 in the myocardial tissue samples of CM treated pigs and control pigs by Western blotting. CM treatment resulted in reduced pSMAD2 expression, indicating that TGF-β signaling via ALK-5 is reduced (FIGS. 4A, B).

Example 17

Results: Apoptosis

Figure 4C:
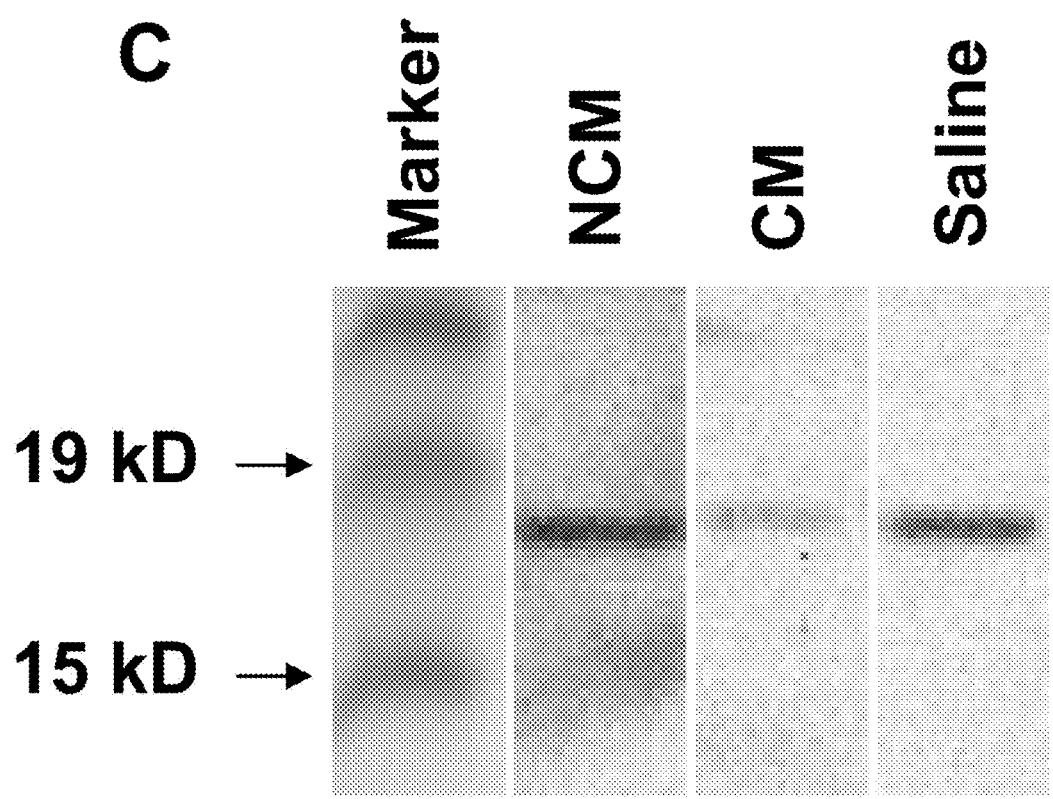
Figure 4D:
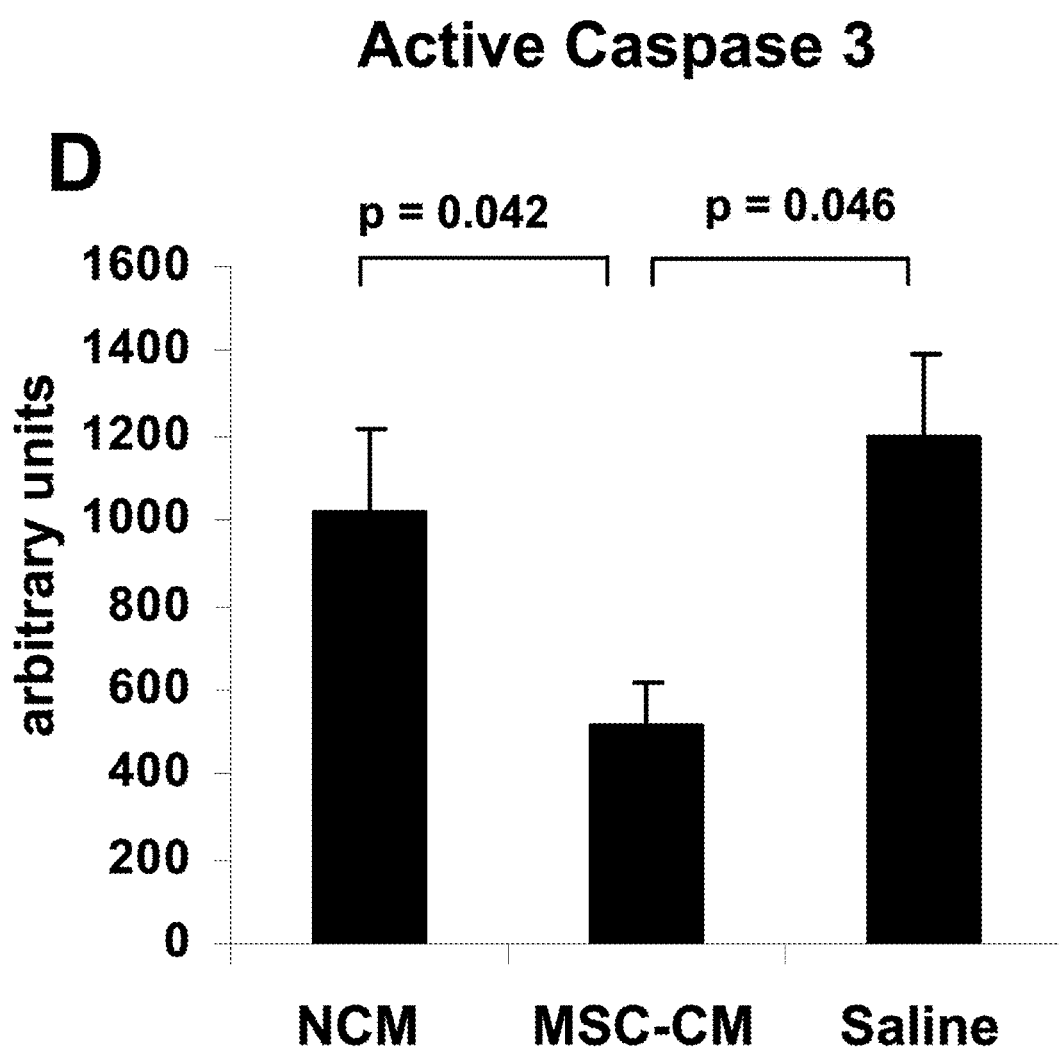
Figure 4E:
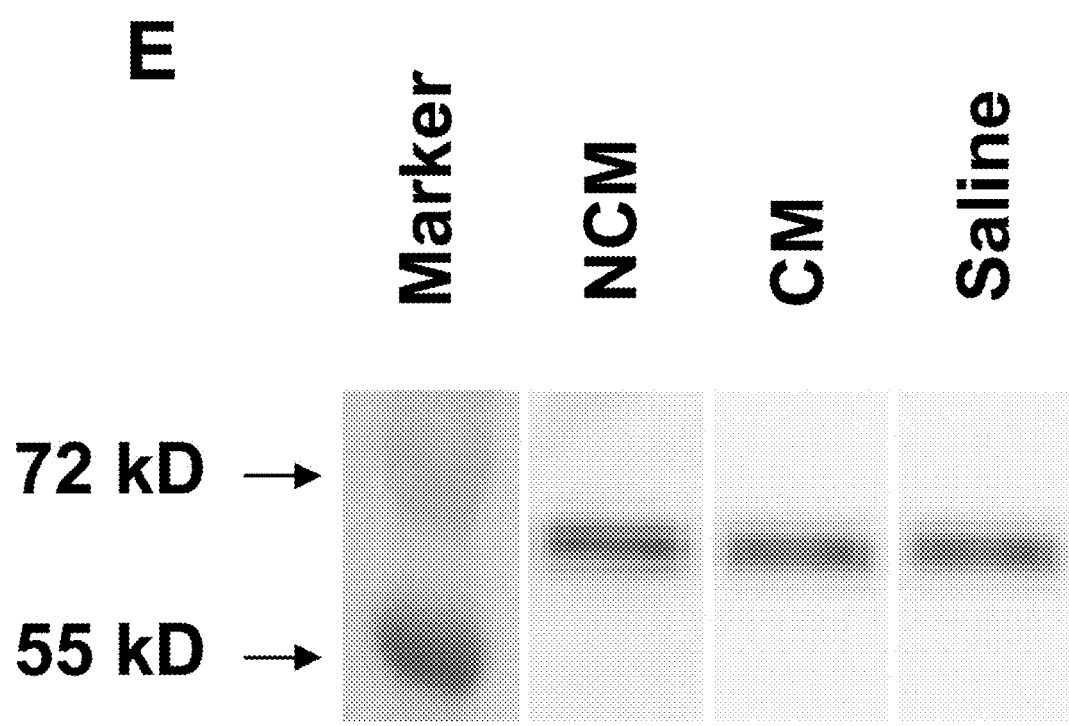

Reperfusion injury causes cell death through apoptosis rather than necrosis[20-22]. To verify that CM treatment reduces apoptosis during reperfusion, we quantified the level of active caspase 3, a key mediator of apoptosis, by western blotting. In the pigs treated with MSC-CM, active caspase-3 levels are lower compared to both non-CM control and saline control suggesting that CM inhibits apoptosis in vivo (FIGS. 4C, D).

Example 18

Results: MSC-CM Fractionation

Figure 5:
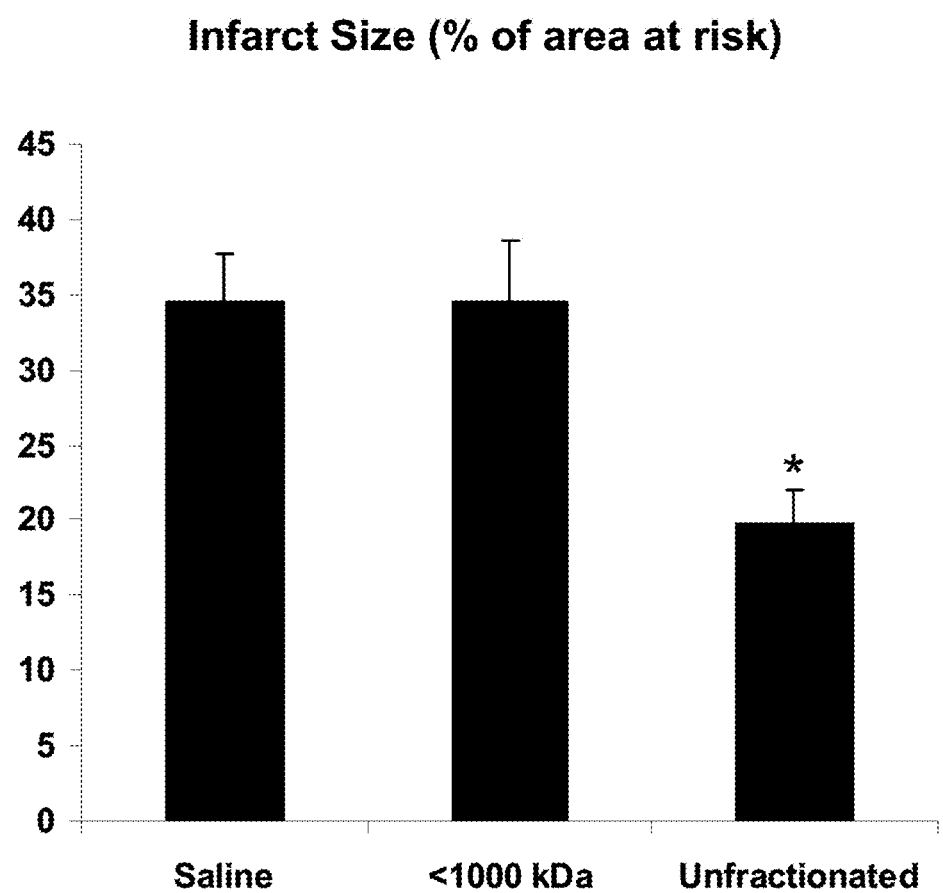
FIG. 5 shows Cardioprotective Properties of CM Fractions. Myocardial infarct size quantification in mice treated with saline, <1000 kD fraction of CM or unfractionated CM. Unfractionated conditioned medium significantly reduces myocardial infarct size compared to saline treated animals. The <1000 kDa fraction, however does not, indicating that the cardioprotective factor(s) is/are larger than 1000 kDa. Saline, n=10; <1000 kD, n=8; unfractionated, n=12. $*p<0.01$ vs. saline.

Unfractionated MSC-CM contains products between 10 and 220 nm. In order to come closer to identifying the cardioprotective factor(s) within the MSC-CM, a <1000 kDa fraction is generated containing products ranging in size from 10-100 nm. Unfractionated MSC-CM confers cardioprotection, whereas the <1000 kDa fraction does not (FIG. 5), indicating that the cardioprotective factor(s) are in the >1000 kDa fraction with size ranging from 100 to 220 nm.

Example 19

Results: Size Fractionation Did not Segregate Secreted Proteins According to Molecular Weights To identify the active component in the Conditioned Medium, we attempted to size-fractionate the Conditioned Medium into distinct MW fractions by filtering the Conditioned Medium through membranes with different MW cut-offs.

Figure 6:
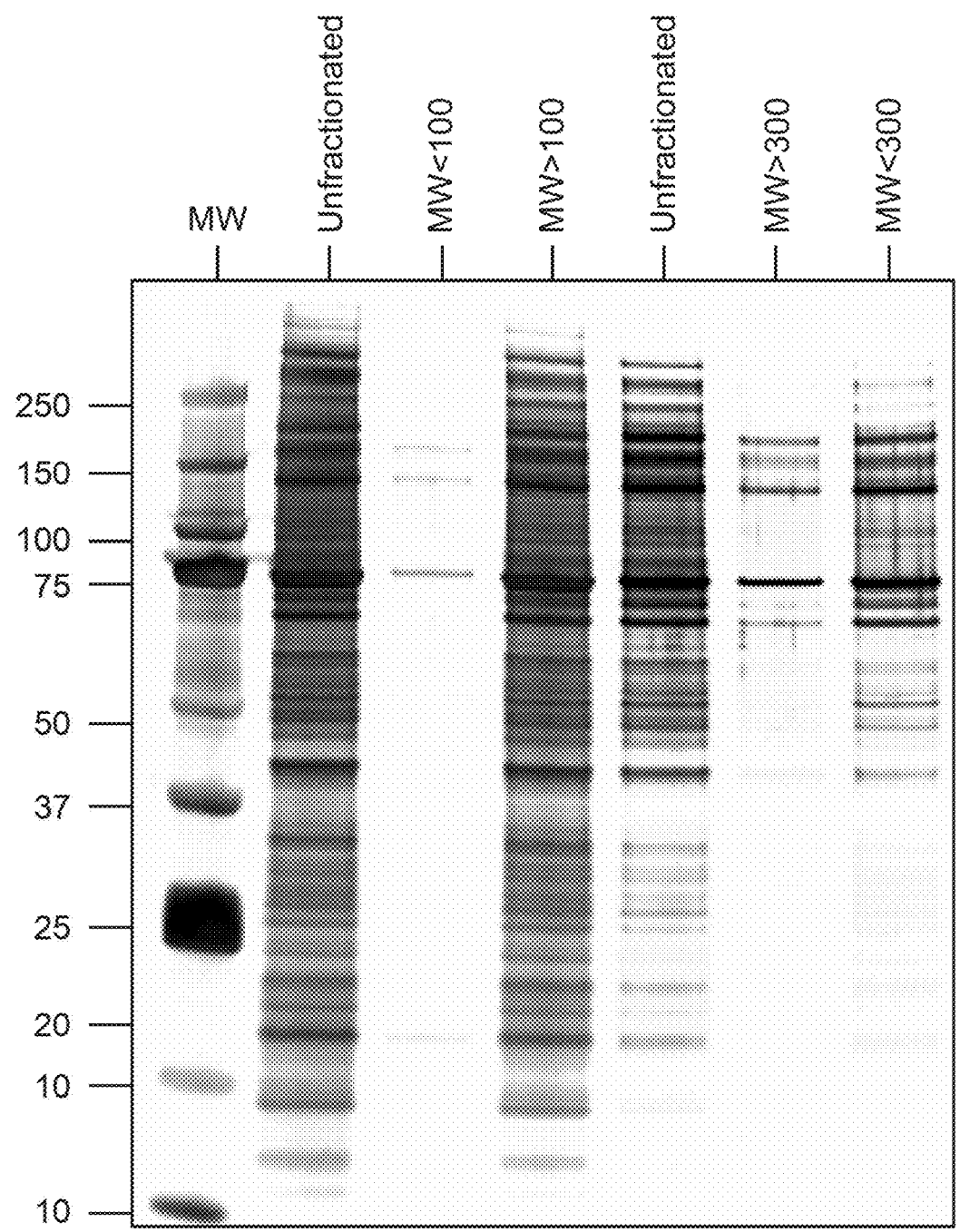
FIG. 6 shows Chemically defined medium conditioned by hESC-MSC HuES9.E1 cells for three days was filtered through a 0.22 µfilter. The conditioned medium (CM) was concentrated 25 times by filtering through a membrane with a 10 kD MW cut-off. The concentrated CM was then centrifuged through a membrane with either a 100 kD or a 300 kD MW cut-off resulting in a 4:1 (vol:vol) filtrate to retentate ratio. The unfractionated CM, filtrate and retentate samples were loaded in the volume ratio of 5:4:1

When the Conditioned Medium is filtered through a membrane of MW cut-off of 100 kD to generate a retentate to filtrate volume ratio of 4:1, most proteins <100 kD segregated into the >100 kD fraction, and not into the expected <100 kD fraction (FIG. 6). The ratio of the individual protein bands in both unfractionated Conditioned Medium and the >100 kD fraction are similar.

Figure 7A:
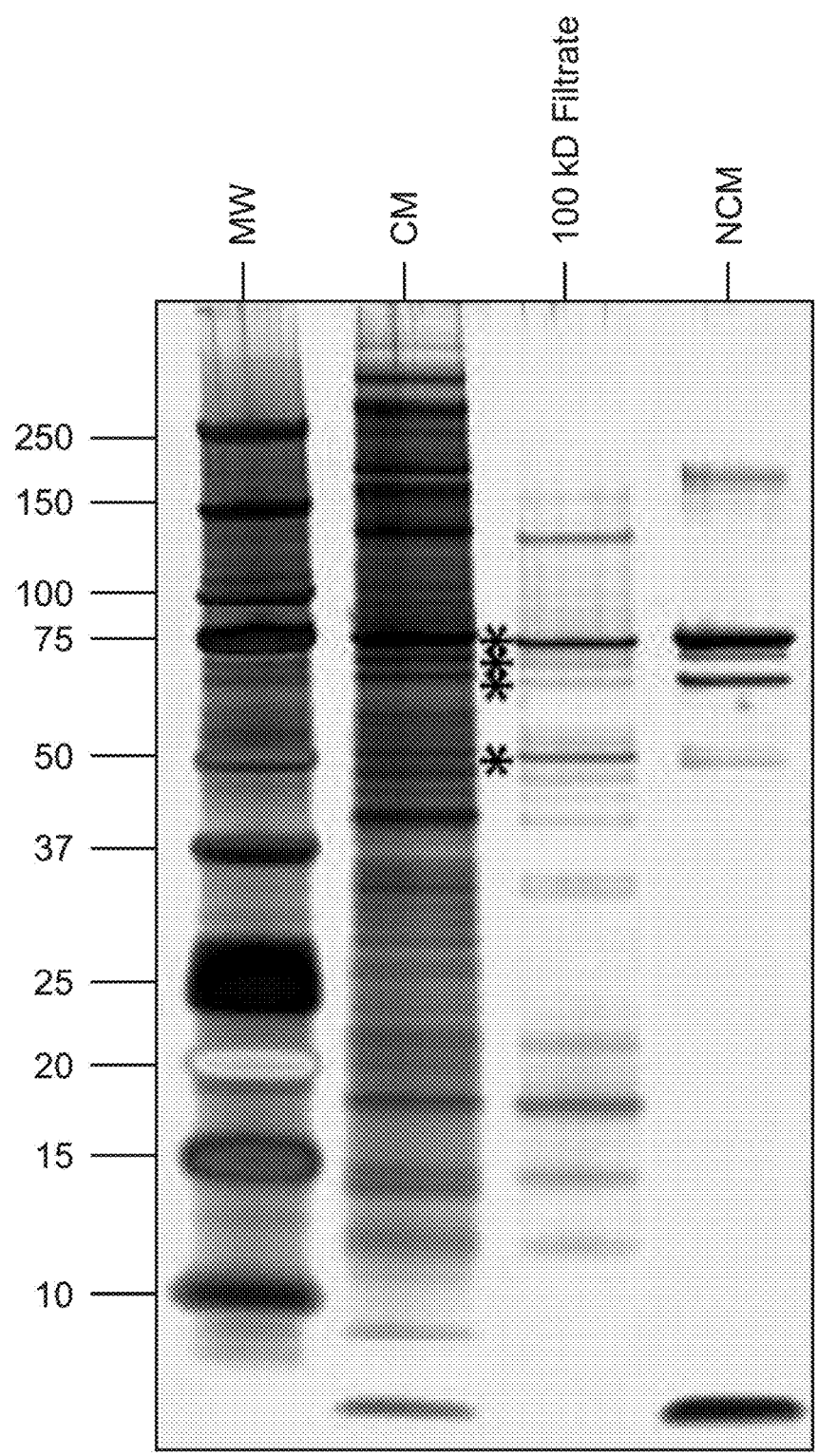
FIGS. 7A-7B show Identity of components in the filtrate after filtration through a membrane with a 100 kD MW cut-off.
Figure 7B:
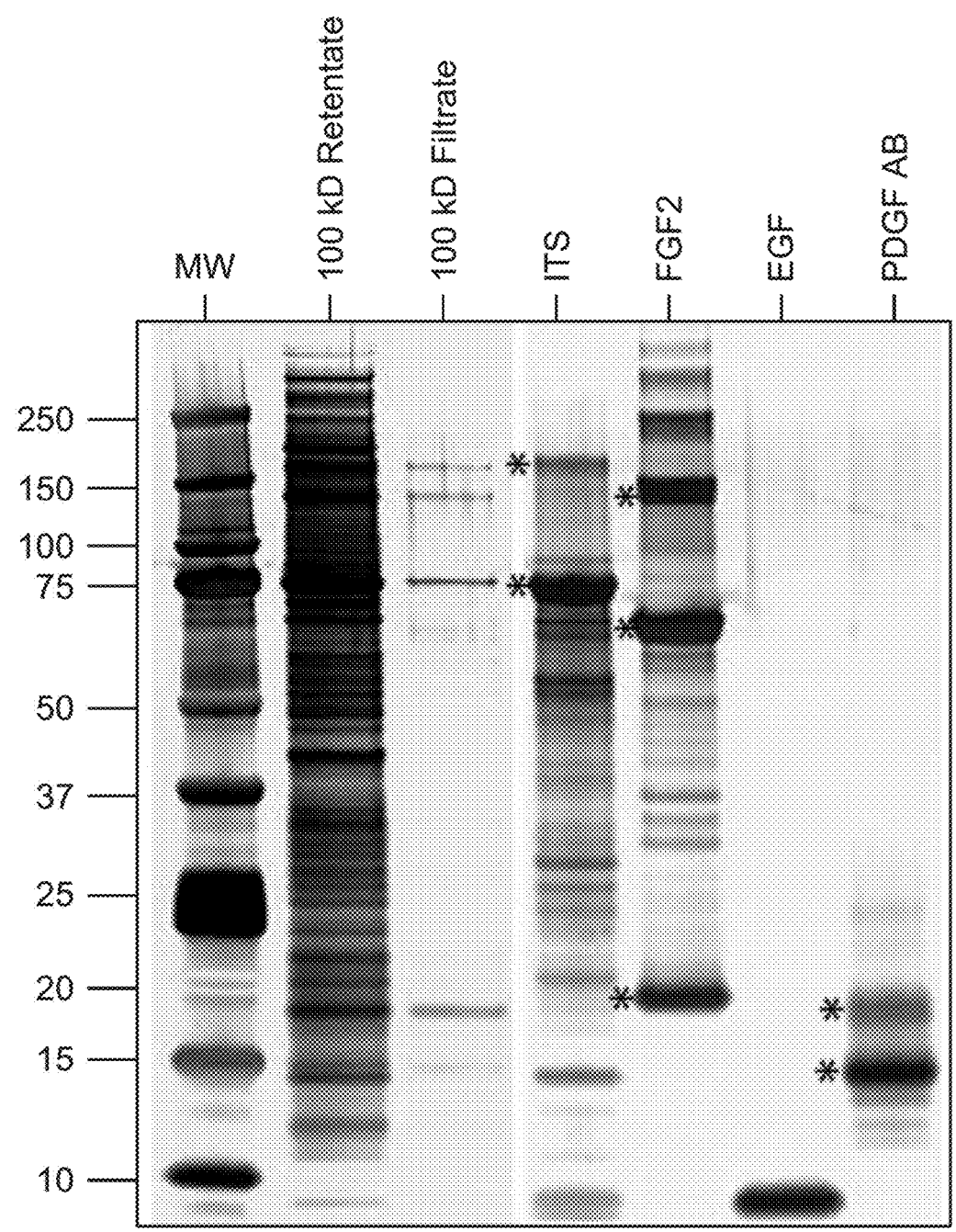

Most proteins with MW <300 kD also did not filter through membrane with a MW cut-off of 300 kD (FIG. 6). The MW sizes of some of the major protein bands in the filtrate are similar to that in the non-conditioned medium (NCM), and to exogenously added protein supplements in the culture media: insulin-transferrin-selenoprotein supplement (ITS), FGF2, EGF and PDGF AB (FIG. 7).

Together these observations suggest that proteins secreted by the cells are in complexes, and these secretion complexes are larger than 100 kD Proteins that are added exogenously to the culture medium as supplements, and that are less than 100 kD are readily filtered through membranes with MW cut off of 100 kD.

Example 20

Figure 8:
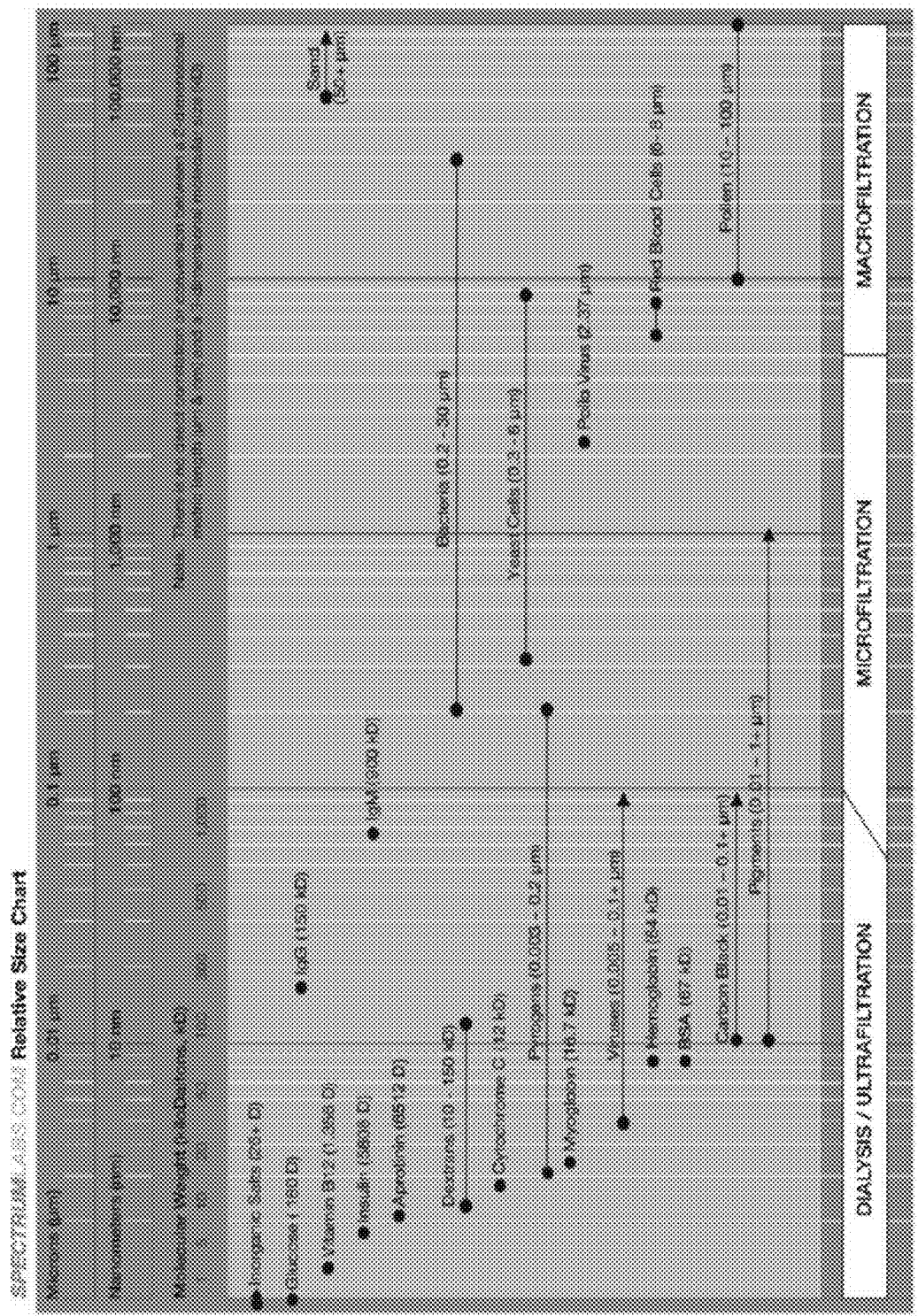
FIG. 8 shows Relative sizes of biological materials and pore sizes in membranes. Reprint from Spectrum© Laboratory.

Results: Biological Activity in Size-Fractionated Conditioned Medium with MW >1,000 kD or Diameter of 50-150 nm To determine the upper and lower size limits of the putative secretion complex, we performed size fractionation of the Conditioned Medium and tested the biological activity in a mouse of ischemia reperfusion injury. As the Conditioned Medium is filtered through 0.2 μM filter and concentrated against a membrane with a MW cut-off of 10 kD, this effectively placed the putative secretion complex in the size range of between 2 to 200 nm (FIG. 8).

To narrow this size range further, we determine if there are biological activity in the filtrate from filtering the Conditioned Medium completely through membrane with a MW cut-off of 100 kD or 1000 kD, retentate from filtering the Conditioned Medium through membrane with a MW cut-off of 1000 kD. The volume of the retentate is ⅕ of the input volume. The fractions are tested on a mouse or pig model of myocardial ischemia (MI) and reperfusion injury.

In this model, MI is induced by 30 minutes left coronary artery (LCA) occlusion by suture ligation and reperfusion is initiated by removal of suture. Mice are treated with 20 μl unfractionated MSC-CM (10-220 nm), 20 μl of <100 or 1,000 kD fraction, 4 μl of >1000 kD retentate or saline intravenously via the tail vein, 5 minutes before reperfusion. 24 hours later, the hearts are excised. Before excision, the Area At Risk (AAR) is determined by religating the LCA and then perfusing Evans blue through the aorta. AAR is defined as the area not stained by the dye and is expressed as a percentage of the left ventricular wall area. Infarct size is assessed 24 hours later using Evans blue and TTC as described previously.

Figure 9:
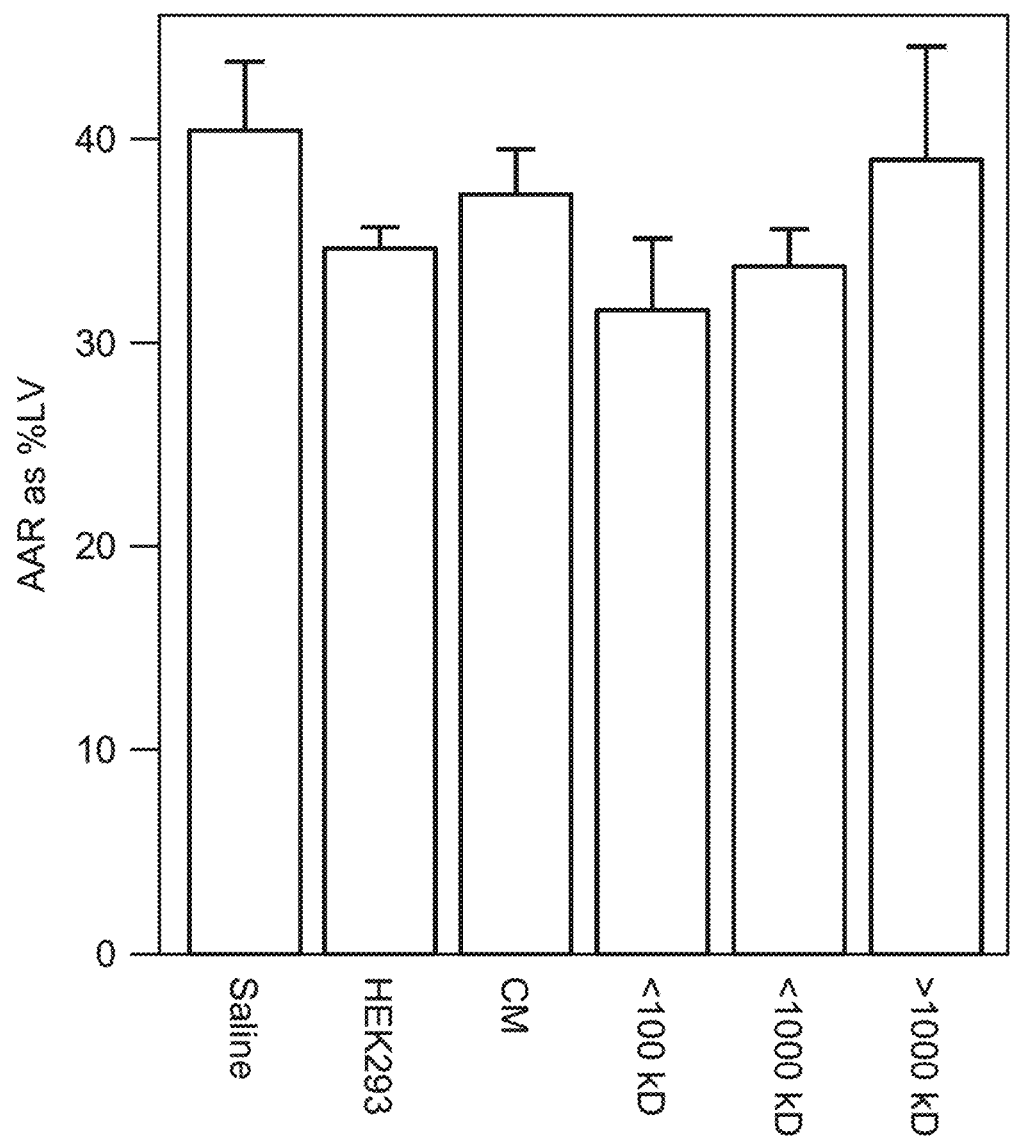
FIG. 9 shows Relative AAR in mice after ischemia/reperfusion. Myocardial infarction was induced by left coronary artery (LCA) occlusion by suture ligation for 30 minutes, and reperfusion was initiated by removal of suture. Five minutes before reperfusion, mice were treated with tail vein injection of 20 µl unfractionated MSC-CM (10-220 nm), 20 µl of <100 or 1,000 kD fraction, 4 µl of >1000 kD retentate or saline. 24 hours later, the hearts were excised. Before excision, the Area At Risk (AAR) was determined by religating the LCA and then perfusing Evans blue through the aorta. AAR was defined as the area not stained by the dye and was expressed as a percentage of the left ventricular wall area.
Figure 10:
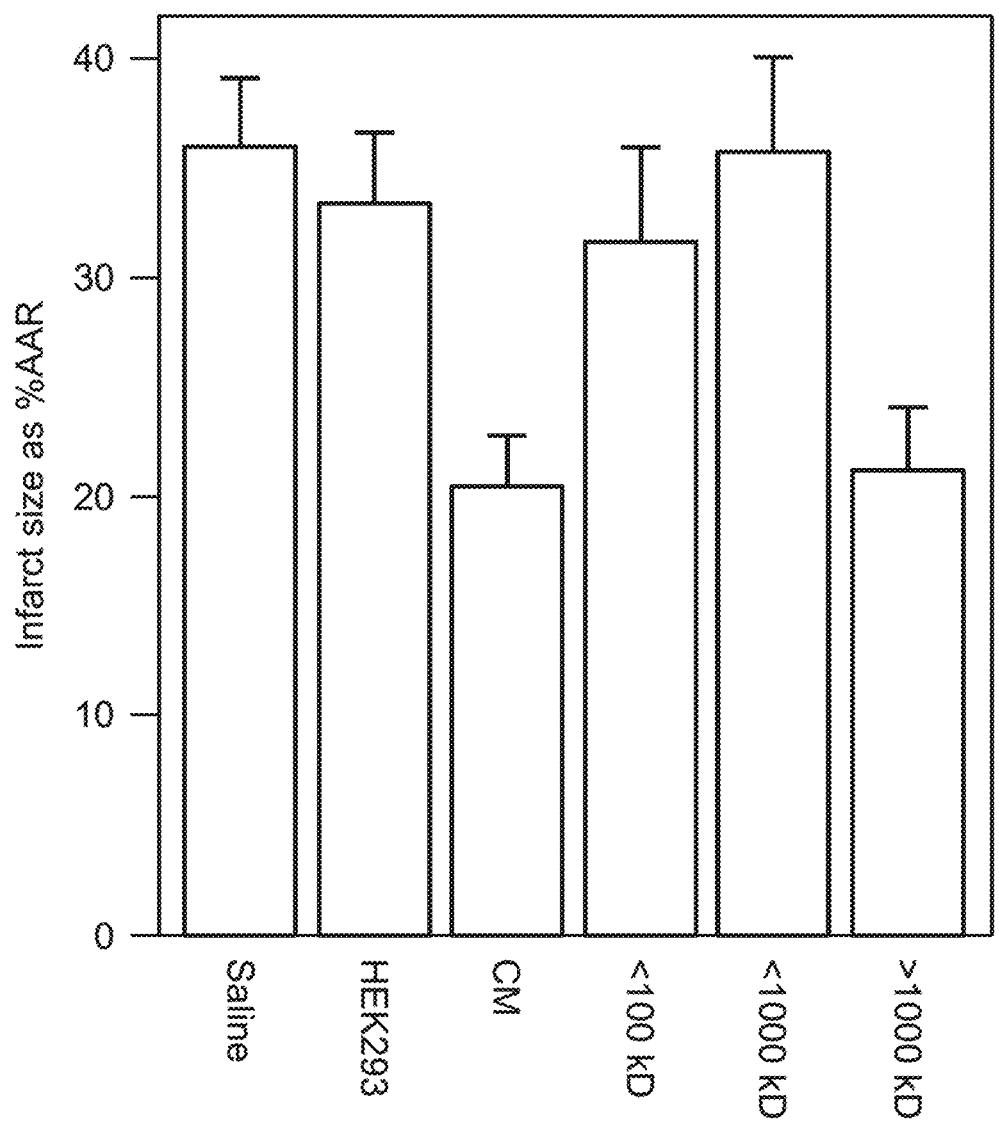
FIG. 10 shows Effects of conditioned media and fractionated conditioned media on relative infarct size in mice after ischemia/reperfusion. After excision of the heart, infarct size was assessed 24 hours later using TTC and expressed as a percentage of AAR.

The relative AAR in all animals are not significantly different (FIG. 9). However the relative infarct size is significantly reduced in animals treated with Conditioned Medium and the >1000 kD fraction when compared to saline ($p=0.01$ and 0.05, respectively) (FIG. 10). The <100 and <1000 kD fractions are not biologically active, suggesting that the putative active complex is >1000 kD. It is, however still possible that the complex is <1000 kD, and that passing the Conditioned Medium through the filters inactivates the complex Example 21

Figure 11:
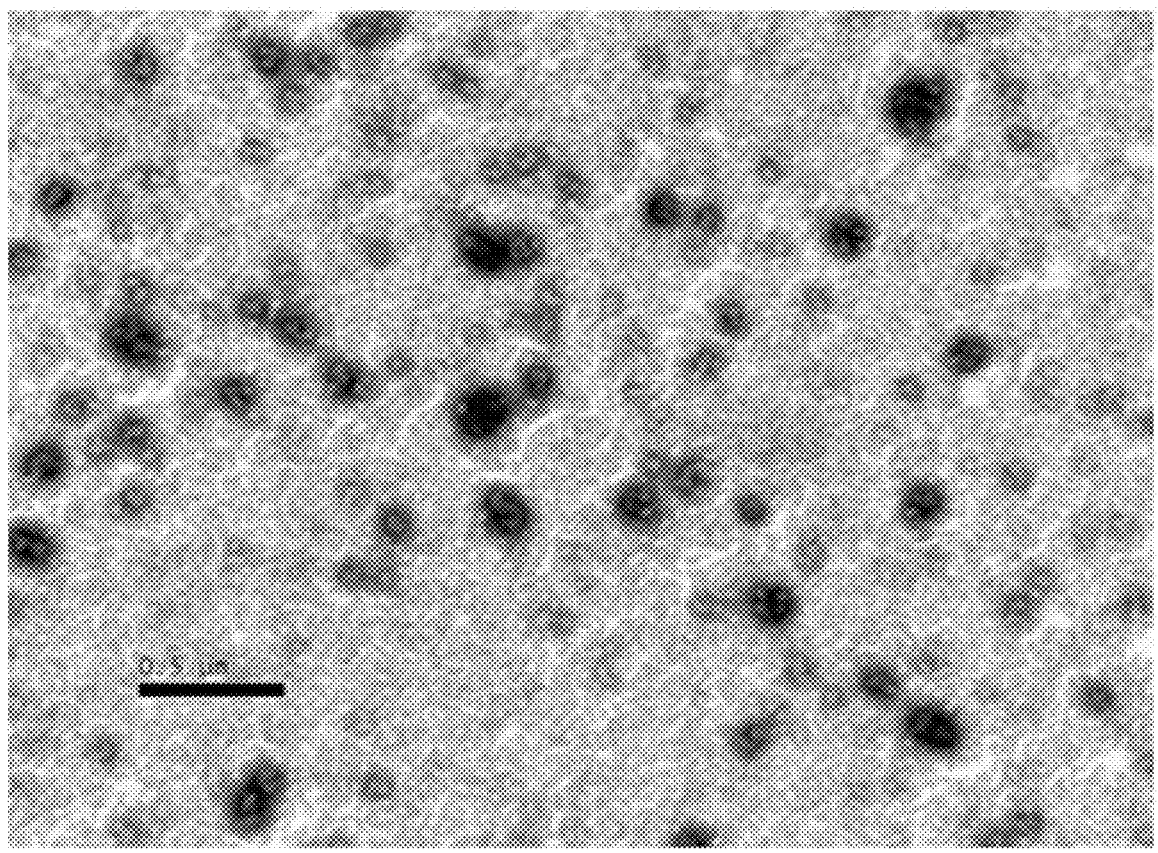
FIG. 11 shows Physical entities of between 50-100 nm in diameter were observed using electron microscopy.

Results: Electron Microscopy of Conditioned Medium Revealed the Presence of 50 to 200 nm Particles Electron microscopy analysis of the Conditioned Medium is performed using standard methodology. Briefly, the Conditioned Medium in PBS is loaded onto formwar carbon coated grids (Ted Pella Inc, Redding, Calif., USA cat no 01800N-F), fixed in 2.5% glutaraldehyde, washed, contrasted in 2% uranyl acetate, embedded in a mixture of uranyl acetate (0.8%) and methyl cellulose (0.13%), and examined under an electron microscope. Consistent with the size fractionation studies above, we observed the presence of numerous vesicles of ~50-150 nm, suggesting that these vesicles are the putative active complexes in the secretion (FIG. 11).

The hypothesis is supported by the observation that when the Conditioned Medium is ultracentrifuged of 200,000×g for an hour, the pellet when assayed by LC/LC-MS as previously described[20] contained at least 70% of the proteins found in the secretion.

Example 22

Results: Lipid Composition of Conditioned Medium

To analyze the lipid composition of the Conditioned Medium, the hydrophobic lipid/steroid components of Conditioned Medium and NCM are extracted by Folch procedure. Briefly, 50 ml of Conditioned Medium or NCM is vigorously mixed with 5 ml of chloroform and 2 ml of methanol. The organic and aqueous phases are allowed to separate. The bottom chloroform layer is removed and evaporated to dryness by speedvac.

The residue is reconstituted in methanol for LC-MS/MS analysis. The sample is then injected to a normal-phase (silica phase) HPLC column with dichloromethane/methanol/water/ethylamine mobile phase. The eluate is then ionized online by nanospray to LTQ-FTMS/Orbitrap. The LTQ-FTMS/Orbitrap is run at alternate positive and negative modes for detection of lipid/steroid with different chemical properties. The top 5 precursor ions of each MS scan are further analyzed by MS/MS scan The molecules are therefore characterized by a combination of FTMS and LTQ. The precursor mass of each tandem mass spectrum is first matched to a candidate in a lipid and metabolic database. MS/MS spectra of ions that have a <5 pmm mass error to any molecule in the database are then compared to known standard spectra or spectra predicted by Mass Frontier program Mass spectrometry analysis of chloroform extract from the Conditioned Medium revealed the presence of lipids commonly found in plasma membrane, namely phospholipids, glycolipids, and steroids and also in exosomes[35]. The phospholipids include phosphatidyl serine and phosphatidyl inositol, phosphatidyl choline, shingomyelin, ceramides; glycolipid such as cerebroside and steroids such as cholesterol.

It has been observed that exosomes has microdomains known as lipid rafts in their lipid membranes[22, 24-35 41, 42]. Exosomes are cholesterol-rich and their cholesterol-phospholipid ratio generally exceed the ratio of 0.3-0.4 (mol/mol) ratio found in plasma membrane[35]. These rafts are characterized by their resistance to dissolution by non-ionic detergents such as Triton X-100 or Brij-98 at low temperatures, and their sensitivity to cyclodextrin that binds cholesterol. Generally insoluble in detergents such as triton X-100 and detergent insolubility is often used to identify the presence of lipid rafts.

Figure 12:
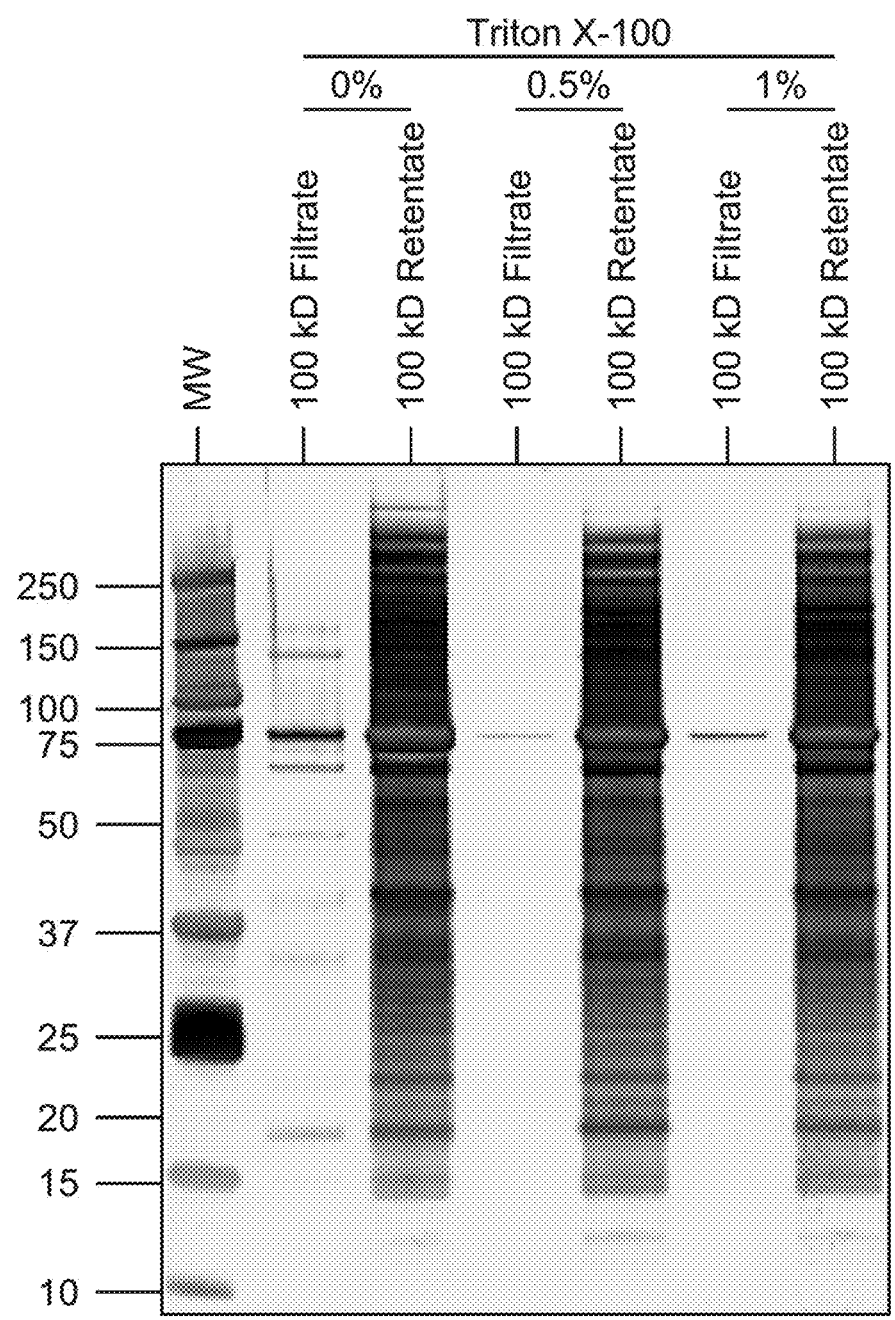
FIG. 12 shows Size fractionation of CM after treatment with Triton X-100, CM was treated with a final 0.5 or 1.0% (v/v) TritonX-100 for 30 minutes and then fractionate by filtration through a membrane with MW cut-off of 100 kD to generate a filtrate:retentate volume ratio of 4:1.

When the Conditioned Medium is treated with Triton X-100, the secreted proteins continued to segregate as a complex independent of their size fractionation experiments using membrane filtration (FIG. 12), suggesting that the putative complex is resistant to dissolution by triton X-100, consistent with the presence of lipid rafts[43].

We determine if the complex is sensitive to dissolution in the presence of 20 mM cyclodextrin. If the putative complex has lipid rafts in the membrane, extraction of cholesterol by cyclodextrin caused dissolution and release the proteins which can then be size fractionated according to their molecular sizes. The relative quantitative composition of lipids in the putative complex is estimated using chromatographic and mass spectrometry techniques as previously outlined[35]. This determines if the lipid composition can support the presence of lipid rafts.

Example 23

Results: RNA Composition of Conditioned Medium

Trizol extraction of the Conditioned Medium followed by isopropanol precipitation as commonly used in the extraction of RNA from cells produces a pellet that in water has an 260:280 nm absorbance ratio of 1.9, suggesting that it may be RNA.

This is consistent with a previous report that exosomes contain mRNAs and microRNAs[36]. This pellet is assayed for sensitivity to RNase activity. The Conditioned Medium will also treated with RNases before extraction with trizol. These assays determine if the pellet is RNA, and if the RNA is sequestered in lipid vesicles such as exosomes.

If so, the RNA is assayed by generic gene expression assays such as microarray, sequencing, RT-PCR and in vitro translation assays to determine the composition and functions of RNA. The RNAs are translated in vitro using standard commercially available reticulocyte lysate system with and without $^{15}$N-leucine. The translated protein products are identified by mass spectrometry.

Example 24

Results: Proteomic Profile

Of the ~700 proteins described to be present in the secretion (U.S. Provisional Patent Application No. 60/878, 222 and International Application PCT/SG2006/000232. Mesenchymal Stem Cell Conditioned Medium), there are many proteins found to be commonly present in the proteome of other exosomes (FIG. 13)[44]. There are also many proteins in the list of ~700 proteins that have not been described to be present in exosomes. Some notable but not exhaustive examples are Thy1, Wnt 5a, Wnt 5b, inhibin A (or activin A)

Example 25

Results: Surface Antigen Profile

The proteomic profile of the Conditioned Medium also describes the presence of proteins that are known to be membrane-bound. Some notable but not exhaustive examples include CD9, CD109, thy-1[20]. Other known surface antigen of exosome such as CD24 that is found on the surface of exosomes secreted in the urine[45] is not expressed in MSCs[19] or its secretion[20].

Additionally, many of these surface antigens are expressed in a cell-type specific manner. Together, these observations suggest that the surface antigen profile will define and distinguish exosomes from different cell source. To characterize the surface antigen profile of these putative secretion complex, the Conditioned Medium is biotinylated using standard commercially available biotinylation kits. The proteins is separated on standard SDS-PAGE, transferred on nylon or nitrocellulose, and probed with avidin-peroxidase using standard protocols in western blot analysis. In this protocol, only proteins that are on the surfaces on the complexes and are physically accessible to biotin are biotinlyated. All the proteins that are within the complex and are therefore not physically accessible are be biotinylated. The biotinylated proteins are also isolated using avidin-affinity chromatography and identify using LC/MS. The identity of these proteins is confirmed by western blot analysis, immunoelectron microscopy and gene expression of MSCs.

Example 26

Exosomes

Based on the above observations, we hypothesize that the smallest active cardioprotective unit in the Conditioned Medium is an exosome.

To prove this hypothesis, we concentrate the Conditioned Medium using membrane filtration technology with membrane of MW cut-off of 100 kD. The concentrated Conditioned Medium is then utlracentrifuged at ~150-200 000 g for 1-2 hours. The pellet is resuspended in PBS, analysed by electron microscopy to confirm the presence of particles with a size range of 50-150 nm, and assayed for its protein, lipid and RNA contents.

The suspension is assayed for the biological activities that are computationally predicted for the Conditioned Medium[20], and is tested for cardioprotective effects in the mouse and pig models as described above or below, respectively.

Example 27

Study Design for Pig Study

Thirty female Dalland Landrace pigs (60-70 kg; IDDLO, Lelystad, The Netherlands), all pretreated with clopidogrel 75 mg/day for 3 days and amiodarone 400 mg/day for 10 days, are randomly assigned to MSC-CM, non-CM, or saline treatment. The saline group is added to assess a potential effect of fresh, non-conditioned culture medium. In all pigs, MI is induced by 75 minutes of proximal left circumflex coronary artery (LCxCA) ligation and 4 hours of subsequent reperfusion. An ischemic period of 75 minutes is selected to inflict severe myocardial injury without inducing completely transmural myocardial infarction. The 4 hour reperfusion period is used, because infarct size measurement using TTC staining is most reliable after 3 hours of reperfusion[46].

After longer periods of reperfusion, it becomes more difficult to assess oxidative stress status and apoptotic mechanisms. Treatment is initiated 5 minutes before the onset of reperfusion by intravenous infusion of MSC-CM (1.0 ml, 2.0 mg protein) non-CM or saline. Immediately following reperfusion, an additional intracoronary bolus MSC-CM (4.0 ml, 8.0 mg protein), non-CM or saline is given. Myocardial infarct size and function are assessed 4 hours after reperfusion.

To identify the factor(s) within the medium that confer cardioprotection, we used a mouse or pig model of ischemia and reperfusion injury. MI is induced by 30 minutes left coronary artery (LCA) occlusion and subsequent reperfusion. Mice are treated with unfractionated conditioned medium, <1000 kD fraction, <500 kD fraction, <300 fraction kD, <100 kD fraction or saline intravenously via the tail vein, 5 minutes before reperfusion. Infarct size is assessed the following day (24 hours after reperfusion).

Example 28

MI and Operational Procedure

During the entire operation, ECG, Systemic Arterial Pressure, and capnogram are monitored continuously. Under general anesthesia as described before[47], a median sternotomy is performed and two introduction sheets are inserted in the carotid arteries for a 6 Fr guiding catheter and an 8 Fr conductance catheter (CD Leycom, Zoetermeer, the Netherlands).

The distal tip of a Swan Ganz catheter is placed into the pulmonary artery via the internal jugular vein. Transonic flow probes (Transonic Systems Inc, Ithaca, N.Y.) are placed around the proximal aorta and LCxCA to measure cardiac output and coronary flow, and a wire is placed around the inferior caval vein to enable functional measurements under varying loading conditions for PV loops. After functional measurements, 10.000 IU of heparin are administered intravenously and sutures are tightened to occlude the proximal LCxCA. Internal defibrillation with 50 J is used when ventricular fibrillation occurred. After 75 minutes of ischemia, the LCxCA is reopened by release of the suture. Immediately following reperfusion, Nitroglycerine (0.1 mg to prevent no-reflow) is infused through the LCxCA via the guiding catheter, followed by intracoronary treatment with MSC-CM, non-CM or saline. After 4 hours of reperfusion, the final functional measurements are performed and the heart is explanted for infarct size analysis.

Mice are anesthetized with Fentanyl (0.05 mg/kg), Dormicum (5 mg/kg) and Domitor (0.5 mg/kg) and intubated using a 24-gauge intravenous catheter with a blunt end. Mice are artificially ventilated at a rate of 105 strokes/min using a rodent ventilator with a mixture of $O_2$ and $N_2O$ (1:2 vol/vol) to which isoflurane (2.5-3.0% vol/vol) is added. The mouse is placed on a heating pad to maintain the body temperature at 37° C. The chest is opened in the third intercostal space and an 8-0 prolene suture is used to occlude the left coronary artery (LCA) for 30 minutes. The chest is closed and the following day (24 hours later), the hearts are explanted for infarct size analysis.

Example 29

Functional Measurements

The ECG, arterial pressure and cardiac output, are digitized at a sampling rate of 250 Hz and stored for offline analysis (Leycom CFL-512, CD Leycom). Left ventricular (LV) pressure and volume are measured using the conductance catheter method, as described previously[47]. LV pressure and volume signals derived from the conductance catheter are displayed and acquired at a 250-Hz sampling rate with a Leycom CFL-512 (CD Leycom).

Data are acquired during steady state and during temporal caval vein occlusion, all with the ventilator turned off at end expiration. Analysis of the pressure-volume loops is performed with custom software as described previously[48]. In addition, short-axis epicardial ultrasound images (Prosound SSD-5000, 5-MHz probe UST-5280-5, Aloka Holding Europe AG, Zug, Switzerland) are obtained at the midpapillary muscle level. Wall thickness (WT) of the infarct area, remote area (septum) and LV internal area (LVia) are measured at end diastole (ED) and end systole (ES).

Systolic wall thickening (SWT) is calculated as [(WT (ES)−WT(ED))/WT(ED)]*100%, fractional area shortening (FAS) as [(LVia(ES)−LVia (ED))/LVia (ED)]*100%, and left ventricular ejection fraction (LVEF) as [(EDV−ESV)/EDV]*100%. The end-diastolic chamber stiffness is quantified by means of linear regression of the end-diastolic pressure-volume relationship. Echocardiography and PV loops are measured before MI, 1 hour after ischemia and 4 hours after reperfusion. To challenge stunned myocardium, additional measurements are performed during pharmaceutically induced stress by intravenous dobutamine infusion (2.5 µg/kg/min and 5.0 µg/kg/min).

Example 30

Infarct Size

Just prior to excision of the heart, the LCxCA (pigs) or LCA (mice) is religated at exactly the same spot as for the induction of the MI. Evans blue dye is infused through the coronary system to delineate the area at risk (AAR). The heart is then excised, the LV is isolated and cut into 5 slices from apex to base.

The slices are incubated in 1% triphenyltetrazolium chloride (TTC, Sigma-Aldrich Chemicals, Zwijndrecht, the Netherlands) in 37° C. Sorensen buffer (13.6 g/L $KH_2PO_4$+ 17.8 g/L $Na_2H\ PO_4.2H_2O$, pH 7.4) for 15 minutes to discriminate infarct tissue from viable myocardium.

All slices are scanned from both sides, and in each slide, the infarct area is compared with area at risk and the total area by use of digital planimetry software (Image J). After correction for the weight of the slices, infarct size is calculated as a percentage of the AAR and of the LV.

Example 31

Materials and Methods: Preparation of Conditioned Medium

HuES9.E1 cells are cultured as described previously (Lian et al., 2007; Sze et al., 2007).

Briefly, 80% confluent HuES9.E1 cell cultures are washed three times with PBS and cultured overnight in a chemically defined medium consisting of DMEM without phenol red (catalog number 31053, Invitrogen) and supplemented with insulin, transferrin, and selenoprotein (ITS) (Invitrogen), 5 ng/ml FGF2 (Invitrogen), 5 ng/ml PDGF AB (Peprotech, Rocky Hill, N.J.), glutamine-penicillin-streptomycin, and -mercaptoethanol. The cultures are then rinsed three times with PBS, and then fresh defined medium is added.

After 3 days, the medium is collected, centrifuged at 500×g and concentrated. >100 kDa CM sample is prepared by concentrating CM 50× using 100 kDa MWCO tangential force filtration (TFF). All other concentrations are performed using ultrafiltration membrane. All CM and other differently processed CMs are 0.2 micron filtered after all procedures and before being stored or used.

Example 32

Materials and Methods: LC MS/MS Analysis

Proteins in two ml of dialyzed conditioned (CM) or non-conditioned media (NCM) are reduced, alkylated, and tryptic digested as described previously described (Sze et al., 2007). The samples are then desalted by passing the digested mixture through a conditioned Sep-Pak C-18 SPE cartridge (Waters, Milford, Mass., USA), washed twice with a 3% acetonitrile (ACN) (JT Baker, Phillipsburg, N.J.) and 0.1% formic acid (FA) buffer, and eluted with a 70% ACN and 0.1% FA buffer. The eluted samples are then dried to about 10% of their initial volumes by removing organic solvent in a vacuum centrifuge.

To reduce the sample complexity, offline peptide fractionation is carried out with a HPLC system (Shimadzu, Japan) through a Polysulfoethyl SCX column (200 mm×4.6 mm) (PolyLC, USA). Mobile phase A (5 mM KH4PO4+30% acetonitrile) and mobile phase B (5 mM KH4PO4+30% acetonitrile+350 mM KCl) at 1 ml/min. Eight fractions are collected and dried with a vacuum centrifuge. Fractionated samples are loaded into the autosampler of a Shimadzu DGU-20A3 C18 reverse phase HPLC system coupled online to a LTQ-FT ultra linear ion trap mass spectrometer (Thermo Electron, San Jose, Calif.) fitted with a nano-spray source. Injected peptides are trapped in a Zorvax 300SB-C18 enrichment column (5 mm×03 mm, Agilent Technologies, Germany) and eluted into a nano-bored C18 packed column (75 μm×1001, Michrom Bioresources, Auburn, Calif.).

A 90 minute gradient at 200 nl/min flow rate is used to elute the peptides into the mass spectrometer. The LTQ is operated in a data-dependent mode by performing MS/MS scans for the 8 of the most intense peaks from each MS scan in the FTMS. For each experiment, MS/MS (dta) spectra of the eight SCX fractions are combined into a single mascot generic file by a home-written program. Protein identification is achieved by searching the combined data against the IPI human protein database (version 3.34; 67,758 sequences) via an in-house Mascot server (Version 2.2, Matrix Science, UK). The search parameters are: a maximum of 2 missed cleavages using trypsin; fixed modification is carbaminomethylation of cysteine and variable modifications is oxidation of methionine. The mass tolerances are set to 20 ppm and 0.8 Da for peptide precursor and fragment ions respectively. Protein identifications are accepted as true positive if two different peptides are found to be with scores greater than the homology scores.

Example 33

Materials and Methods: HPLC Fractionation and Dynamic Light Scattering Using a Quasi-Elastic Light Scattering (QELS) Detector The instrument setup consisted of a liquid chromatography system with a binary pump, an auto injector, a thermostated column oven and a UV-visible detector operated by the Class VP software from Shimadzu Corporation (Kyoto, Japan). The Chromatography columns used are TSK Guard column SWXL, 6×40 mm and TSK gel G4000 SWXL, 7.8×300 mm from Tosoh Corporation (Tokyo, Japan). The following detectors, Dawn 8 (light scattering), Optilab (refractive index) and QELS (dynamic light scattering) are connected in series following the UV-visible detector. The last three detectors are from Wyatt Technology Corporation (California, USA) and are operated by the ASTRA software.

The components of the sample are separated by size exclusion i.e. the larger molecules will elute before the smaller molecules. The eluent buffer used is 20 mM phosphate buffer with 150 mM of NaCl at pH 7.2. This buffer is filtered through a pore size of 0.1 μm and degassed for 15 minutes before use. The chromatography system is equilibrated at a flow rate of 0.5 ml/min until the signal in Dawn 8 stabilized at around 0.3 detector voltage units. The UV-visible detector is set at 220 nm and the column is oven equilibrated to 25° C. The elution mode is isocratic and the run time is 40 minutes. The volume of sample injected ranged from 50 to 100 μl. The % area of the exosome peak vs. all other peaks is integrated from the UV-visible detector. The hydrodynamic radius, $R_h$ is computed by the QELS and Dawn 8 detectors. The highest count rate (Hz) at the peak apex is taken as the $R_h$.

Peaks of the separated components visualized at 220 nm are collected as fractions for further characterization studies.

Example 34

Materials and Methods: Sucrose Gradient Density Equilibrium Centrifugation

For sucrose gradient density equilibrium centrifugation, 14 sucrose solutions with concentrations from 22.8-60% (w/v) are prepared. The most concentrated solution is layered at the bottom of SW60Ti ultracentrifuge tube (Beckman Coulter Inc., Fullerton Calif., USA), followed by the next highest sucrose concentration. CM is carefully loaded on top before ultracentrifuged for 16.5 hours at 200,000×g, 4° C. in a SW60Ti rotor (Beckman Coulter Inc.). 16 fractions are collected from top to the bottom of the sucrose gradient. The densities of all the sucrose fractions are calculated using a microbalance, and consolidated into to 13 fractions. For some CM, the CM is pretreated with a cell lysis buffer (Cell Extraction Buffer, Biovision, www.BioVision.com) before being loaded on sucrose gradient density equilibrium centrifugation. The lysis buffer is added to CM in a 1:1 volume ratio with cocktail of protease inhibitors (Halt Protease Inhibitor Cocktail, EDTA-Free, Thermo Scientific, www.thermofisher.com). The mixture is incubated for 30 min at room temperature with gentle shaking.

Example 35

Materials and Methods: Protein Quantitation

Protein concentration of CM is quantified using NanoOrange Protein Quantification kit (Invitrogen) according to the manufacturer's instructions.

Example 36

Materials and Methods: SDS-PAGE and Western Blot Analysis

Total proteins of CM are separated on polyacrylamide gels, before transfer to a nitrocellulose membrane (Amersham Biosciences, Uppsala, Sweden). The membrane is blocked, incubated with mouse antibodies against human CD9, CD81, SOD-1, pyruvate kinase, Alix, Tsp-1 followed by horseradish peroxidase-coupled secondary antibodies against the mouse primary antibody. The blot is then incubated with a chemiluminescent HRP substrate to detect bound primary antibody, and therefore the presence of the antigen.

Example 37

Materials and Methods: Sphingomyelin, Phosphatidylcholine and Cholesterol Assay

Cholesterol, sphingomyelin and phosphatidylcholine concentrations in two independent preparations of CM and pellet from the ultracentrifugation of CM at 100,000×g for 2 hours at 4° C. are measured using commercially available assay kits. Cholesterol is measured using Amplex® Red Cholesterol Assay kit (Molecular Probes, USA), sphingomyelin by the Sphingomyelin Assay Kit (Cayman Chemical Company, Ann Arbor, Mich., USA) and phosphatidylcholine is measured using the Phosphatidylcholine Assay Kit (Cayman Chemical Company, Ann Arbor, Mich., USA).

Example 38

Materials and Methods: Limited Trypsinization of Conditioned Medium

CM is treated with/without triton x or lysis buffer for 30 min at 4° C. with gentle shaking Proteolytic digestion is allowed to carry out by adding trypsin to the treated CM for 3 seconds to 20 minutes at room temperature with gentle shaking. The digestion is stopped using a trypsin inhibitor, PMSF.

Example 39

Materials and Methods: miRNA Microarray Analysis

Two biological replicates of total cellular RNA from MSCs and two biological replicates of secreted RNA from CM are analysed by miRNA microarray. The hybridization and data analysis is outsourced to LC Sciences, LLC (www.LCsciences.com). The chip contained probes for miRNA transcripts listed in Sanger miRBase Release 10.1 (http://www.sanger.ac.uk/Software/Rfam/mirna/).

Example 40

Figure 14:
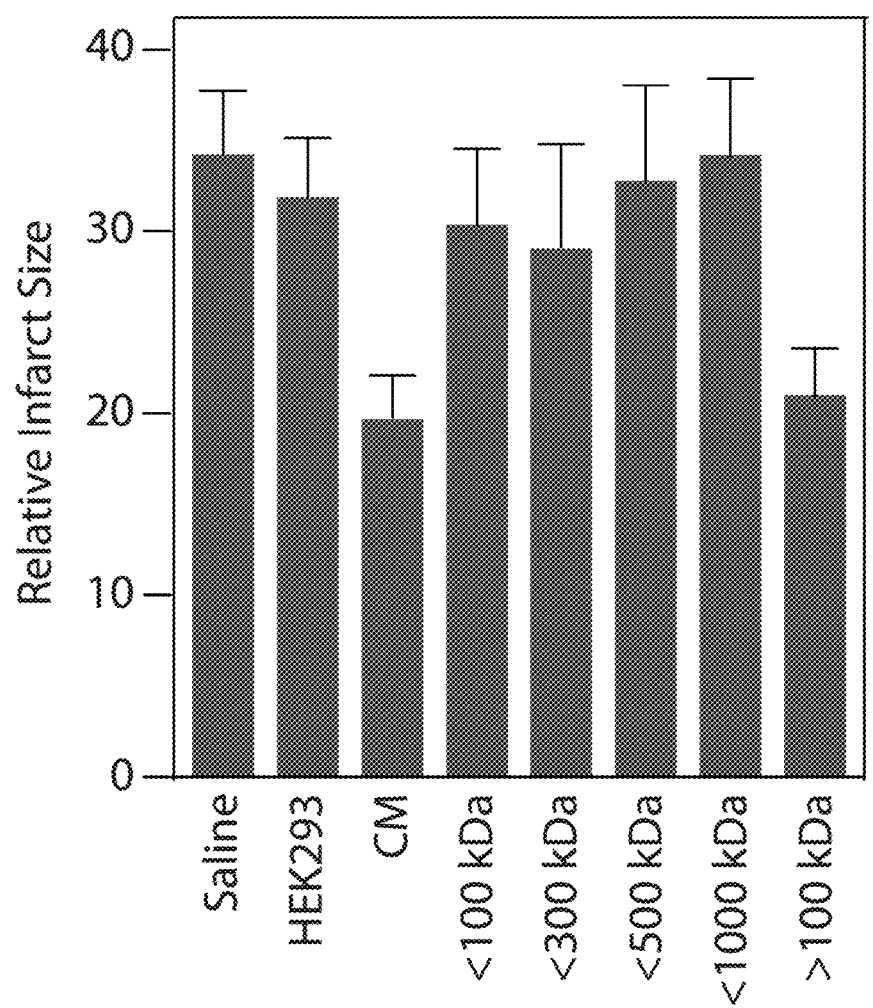
FIG. 14 shows Cardioprotective Properties of CM Fractions. Myocardial infarct size quantification in mice treated with saline, HEK293 conditioned medium, unfractionated hESC-CM, CM filtered with MWCO of 100 kDa, 300 kDa, 500 kDa, and 1000 kDa or CM concentrated 50 times against membrane with MWCO of 100 kDa fraction of CM or unfractionated CM.

Results: Cardioprotective Secretion Contains Exosome-Associated Proteins that Form Multiprotein Complexes To identify the active component, we have previously fractionated the CM by ultrafiltration through membranes with different MWCO. It is shown that when CM is filtered through a membrane with MWCO of 1000 kDa, the filtrate is not protective. However, CM that is concentrated by ~125 times against a similar membrane is cardioprotective in a mouse model of ischemia/reperfusion injury. In summary, filtration through filters with a MWCO smaller than 0.2 µm such as 100 kDa, 300 kDa, 500 kDa or 1000 kDa are not cardioprotective (FIG. 14) but CM that is concentrated against a 1000 kDa membrane (Timmers et al., 2008) or a 100 kDa membrane is cardioprotective (FIG. 14). These observations suggested then that the active fraction consisted of large complexes of >1000 kDa or having a diameter of 50-100 nm. Based on the size range of the particles, we postulated that the particles in the CM are exosomes. Exosomes are formed from multivesicular bodies (Fevrier and Raposo, 2004; Keller et al., 2006) with a bilipid membrane that has the same orientation as plasma membrane. They are known to be produced by many cell types and are thought to be important in intercellular communications. Exosomes have diameters of 40-100 nm. Exosomes have been shown to be secreted by many cell types and the protein composition of these exosomes appeared to be cell specific. However, some proteins such as CD9, pyruvate kinase and alix appear to be commonly expressed in the exosomes (Sze et al., 2007). We have previously identified about 201 proteins in the secretion (Sze et al., 2007).

Figure 15:
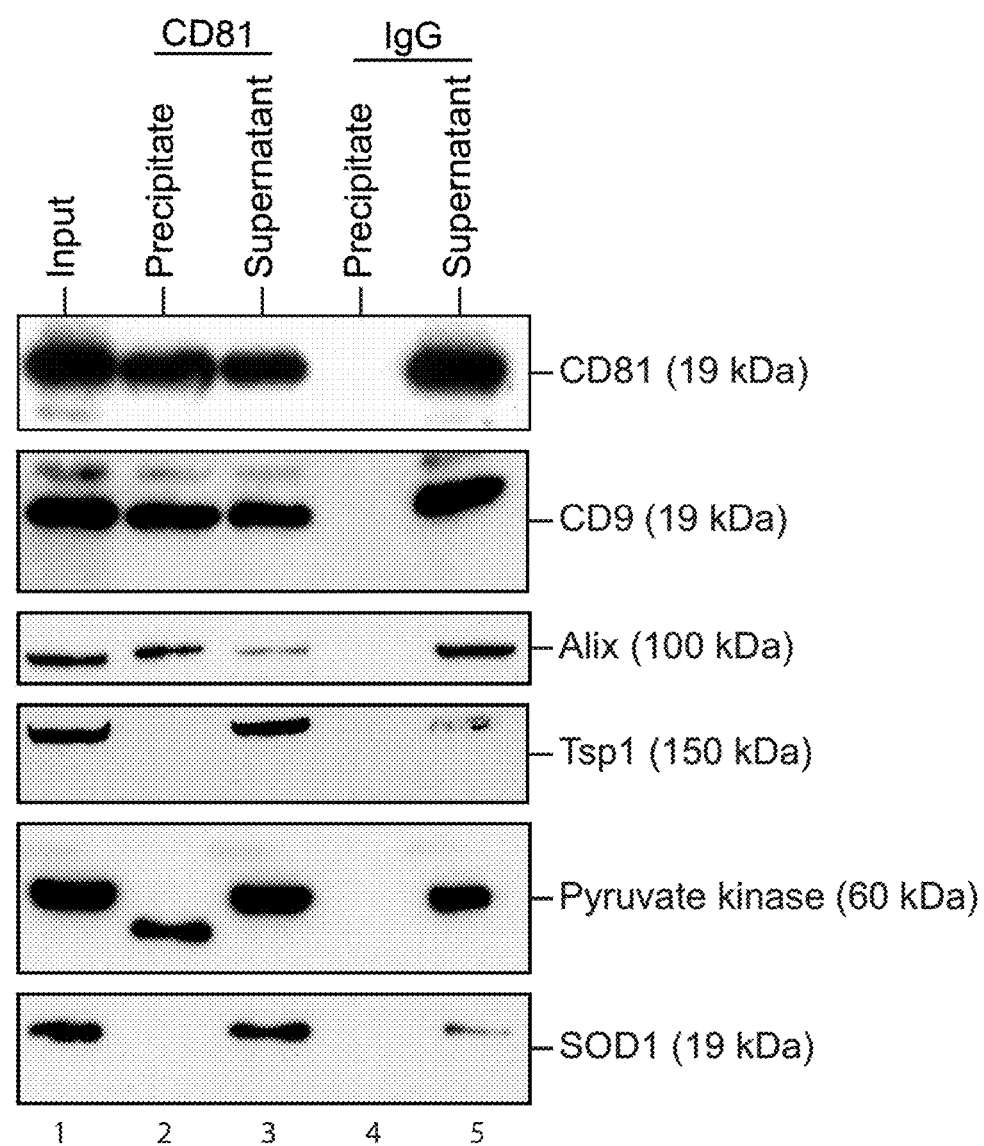
FIG. 15 shows Immunoprecipitation. CM immunoprecipitated with anti-CD81 or mouse IgG as negative control. The immunoprecipitate and supernatant were analysed by western blot hybridization using antibody against CD9, Alix, Tsp-1, pyruvate kinase and SOD1.

Here we extended the list to 793 proteins (Table E2) by making modifications to our previously described methodology in our proteomic analysis as detailed in the Materials and Methods. The 793 contained many of the exosome-associated proteins such as CD9, CD81, Alix, TSP-1, SOD-1 and pyruvate kinase (Olver and Vidal, 2007). We confirmed the presence of these proteins in the secretion by western blot analysis (Lane1, FIG. 15). Co-immunoprecipitation of CD81, CD9 and Alix supported their association with an exosome and the presence of exosome in the secretion. TSP-1, SOD-1 and pyruvate kinase did not co-immunoprecipitated with CD81, suggesting that these proteins are not present in CD81+ exosomes or not present in exosomes at all. (FIG. 15).

Table E2 (below). Alphabetical list of 739 unique gene products identified by LC-MS/MS and antibody array

TABLE E2

Proteomic profile of CM as determined by LC MS/MS and antibody arrays. Four independent samples were analyzed. Each protein in the table was detected in at least 3 of 4 samples.

| | | | | | | | | | |
|---|---|---|---|---|---|---|---|---|---|
| 02-Sep | BPNT1 | COL5A3 | FAM3C | HINT1 | ITGB4BP | MYH9 | PPIA | RPLP2 | THBS2 |
| 07-Sep | BTD | COL6A1 | FAM49B | HIST1H4 | K-ALPHA-1 | MYL6 | PPIB | RPS10 | THOP1 |
| AARS | C14orf141 | COL6A2 | FAM62A | HIST1H4A | KPNB1 | NAGK | PPP2R1A | RPS15A | THY1 |
| ACAA2 | C19orf10 | COL6A3 | FBLN1 | HIST1H4B | KRT1 | NANS | PPP2R4 | RPS16 | TIMP1 |
| ACAT2 | C1orf58 | COL7A1 | FBLN5 | HIST1H4C | KRT14 | NARS | PPP5C | RPS19 | TIMP2 |
| ACO1 | C1orf78 | COPA | FBN1 | HIST1H4D | KRT2 | NEDD8 | PPP6C | RPS2 | TIMP3 |
| ACTB | C1QBP | COPG | FBN2 | HIST1H4E | KRT27 | NEFM | PRDX1 | RPS20 | TKT |
| ACTC1 | C1R | COPS3 | FDPS | HIST1H4F | KRT4 | NIT2 | PRDX2 | RPS23 | TLN1 |
| ACTN1 | C1S | COPS4 | FGF16 | HIST1H4H | KRT5 | NME1 | PRDX3 | RPS3 | TMOD2 |
| ACTN2 | C21orf33 | COPS8 | FGFRL1 | HIST1H4I | KRT6L | NPC2 | PRDX4 | RPS4X | TMOD3 |
| ACTN3 | CALR | CORO1B | FH | HIST1H4J | KRT7 | NPEPPS | PRDX5 | RPS5 | TNC |
| ACTN4 | CAND1 | CORO1C | FKBP10 | HIST1H4K | KRT75 | NPM1 | PRDX6 | RPS7 | TNFRSF11B |
| ACTR1A | CAP1 | COTL1 | FKBP1A | HIST1H4L | KRT77 | NQO1 | PRG1 | RPS8 | TNFRSF12A |
| ACTR1B | CAP2 | CRIP2 | FKBP3 | HIST2H2AA3 | KRT9 | NRP1 | PRKACA | RPS9 | TNFSF12 |
| ACTR2 | CAPG | CS | FLNA | HIST2H2AA4 | KRTHB4 | NRP2 | PRKCSH | RPSA | TNPO1 |
| ACTR3 | CAPN1 | CSE1L | FLNB | HIST2H4A | LAMA4 | NT5E | PRNP | RSU1 | TP53I3 |
| ACTR3B | CAPN2 | CSRP1 | FLNC | HIST2H4B | LAMB1 | NUCB1 | PROCR | RTN4 | TPI1 |
| ADAM9 | CAPZA1 | CSRP2 | FLRT2 | HIST4H4 | LAMC1 | OLFML3 | PROSC | S100A11 | TPM1 |
| ADSL | CAPZA2 | CST3 | FLT1 | HLA-A | LANCL1 | P4HA1 | PRSS23 | S100A16 | TPM2 |
| ADSS | CAPZB | CTGF | FN1 | HLA-B | LAP3 | P4HB | PRSS3 | SARS | TPM3 |
| AEBP1 | CARS | CTHRC1 | FSCN1 | HMX1 | LASP1 | PABPC1 | PSAP | SDC4 | TPM4 |
| AGA | CBR1 | CTSB | FSTL1 | HNRPA1 | LDHA | PABPC4 | PSAT1 | SEC22B | TRAP1 |
| AGRN | CBR3 | CTSD | FSTL5 | HNRPA1L-2 | LDHAL6B | PAFAH1B1 | PSMA1 | SEC23A | TRHDE |
| AHCY | CCBL2 | CTSZ | FTL | HNRPA2B1 | LDHB | PAFAH1B2 | PSMA2 | SEC31A | TROVE2 |
| AK1 | CCDC19 | CXCL1 | G6PD | HNRPC | LEPRE1 | PAFAH1B3 | PSMA3 | SEMA3C | TSKU |
| AK2 | CCL18 | CXCL12 | GALNT2 | HNRPA1 | LGALS1 | PAICS | PSMA6 | SEMA7A | TUBA1A |
| AKR1A1 | CCL2 | CXCL16 | GALNT5 | HNRPD | LGALS3 | PAM | PSMA7 | SERPINB1 | TUBA6 |
| AKR1B1 | CCL7 | CXCL2 | GANAB | HNRPDL | LGALS3BP | PAPPA | PSMB1 | SERPINB6 | TUBA8 |
| ALCAM | CCN4 | CXCL9 | GAPDH | HNRPH2 | LMNA | PARK7 | PSMB2 | SERPINE1 | TUBB |
| ALDH2 | CCR4 | CYCS | GARS | HNRPK | LOC196463 | PARP1 | PSMB3 | SERPINE1 | TUBB2C |
| ALDH7A1 | CCR5 | D4ST1 | GAS6 | HNRPL | LOC283523 | PARVA | PSMB4 | SERPINE2 | TUBB3 |
| ALDOA | CCT2 | DAG1 | GBA | HNRPR | LOC347701 | PCBP1 | PSMB5 | SERPINF1 | TUBB4 |
| ALDOC | CCT3 | DCI | GBE1 | HNRPU | LOC646821 | PCBP2 | PSMD11 | SERPINH1 | TUBB6 |
| ANGPT | CCT4 | DCN | GDF1 | HNT | LOC649125 | PCDH18 | PSMD13 | SERPINI2 | TUBB8 |
| ANP32B | CCT5 | DDAH2 | GDF11 | HSP90AB1 | LOC653214 | PCDHGB6 | PSMD5 | SFRP1 | TWF1 |
| ANXA1 | CCT6A | DDB1 | GDF15 | HSP90B1 | LOC654188 | PCK2 | PSMD6 | SFRP4 | TXN |
| ANXA2 | CCT7 | DDT | GDF3 | HSPA1A | LOC728378 | PCMT1 | PSMD7 | SH3BGRL3 | TXNL5 |
| ANXA5 | CCT8 | DDX17 | GDF5 | HSPA1B | LOXL2 | PCNA | PSME1 | SIL1 | TXNRD1 |
| ANXA6 | CD109 | DES | GDF8 | HSPA1L | LRP1 | PCOLCE | PSME2 | SLC1A5 | UBE1 |
| AP1B1 | CD248 | DKK1 | GDI1 | HSPA4 | LTA | PDCD6IP | PTBP1 | SLC3A2 | UBE2L3 |
| AP1S1 | CD44 | DLD | GDI2 | HSPA5 | LTA4H | PDGFA | PTK7 | SND1 | UBE2N |
| AP2A1 | CD59 | DNAJC3 | GLO1 | HSPA6 | LTB | PDGFC | PTPRCAP | SNRPD1 | UBE2V1 |
| AP2A2 | CD81 | DPP3 | GLRX | HSPA8 | LTB4DH | PDGFRB | PTX3 | SNRPE | UBE3B |
| AP2B1 | CD9 | DPYSL2 | GLT8D3 | HSPB1 | LTBP1 | PDIA3 | PURA | SOD1 | UCHL1 |
| AP3B1 | CDC37 | DPYSL3 | GLUD1 | HSPD1 | LTBP2 | PDIA4 | PXDN | SPARC | UCHL3 |
| APEX1 | CDC42 | DSTN | GM2A | HSPE1 | LUM | PDIA6 | PYCR1 | SPOCK | UGDH |
| API5 | CDH11 | DYNLL1 | GNPDA1 | HSPG2 | M6PRBP1 | PDLIM1 | PYGB | SPTAN1 | UGP2 |
| APOA1BP | CDH13 | ECHS1 | GNPNAT1 | HSPH1 | MACF1 | PDLIM5 | QARS | SPTBN1 | UROD |
| APOE | CDH2 | ECM1 | GOT1 | HTRA1 | MADH4 | PDLIM7 | QPCT | SPTBN4 | USP14 |
| APP | CFL1 | EEF1A1 | GOT2 | IDH1 | MAP1B | PEPD | QSCN6 | SRP9 | USP5 |
| APRT | CFL2 | EEF1A2 | GPC1 | IFNG . . . | MAPK1 | PFN1 | RAB11B | SRPX | VARS |
| ARCN1 | CHID1 | EEF1B2 | GPC5 | IGF2R | MAPRE1 | PFN2 | RAB1A | SRPX2 | VASN |
| ARHGAP1 | CHRDL1 | EEF1G | GPI | IGFBP2 | MAT2A | PGCP | RAB6A | SSB | VAT1 |
| ARHGDIA | CLEC11A | EEF2 | GREM1 | IGFBP3 | MAT2B | PGD | RAC1 | ST13 | VCL |
| ARPC1A | CLIC1 | EFEMP1 | GRHPR | IGFBP4 | MCTS1 | PGK1 | RAN | ST6GAL2 | VCP |
| ARPC1B | CLIC4 | EIF2S3 | GRN | IGFBP5 | MDH1 | PGK2 | RANBP5 | STAT1 | VEGFC |
| ARPC2 | CLSTN1 | EIF3S9 | GSN | IGFBP7 | MDH2 | PGLS | RARRES2 | STC1 | VIL2 |
| ARPC3 | CLTC | EIF4A1 | GSR | IGKC | MFAP4 | PGM1 | RARS | STC2 | VIM |
| ARPC4 | CLTCL1 | EIF4A2 | GSS | IL13 | MGAT5 | PGRMC2 | RBMX | STIP1 | VPS26A |
| ARTS-1 | CLU | EMILIN1 | GSTK1 | IL15 | MIF | PHGDH | RHOA | SULF1 | VPS35 |
| ATIC | CMPK | EML2 | GSTO1 | IL15RA | MMP1 | PHPT1 | RNASE4 | SVEP1 | VTN |
| ATP5B | CNDP2 | ENO1 | GSTP1 | IL1RAP | MMP10 | PICALM | RNH1 | SYNCRIP | WARS |
| ATP6AP1 | CNN2 | ENO2 | GTPBP9 | IL2 | MMP14 | PKM2 | RNPEP | TAGLN | WDR1 |
| ATP6AP2 | CNN3 | ENO3 | GZMA | IL21R | MMP2 | PLAU | RPL10A | TAGLN2 | WNT5A |
| ATP6V1B2 | COL12A1 | EPPK1 | H2AFY | IL3 | MRC2 | PLEC1 | RPL11 | TALDO1 | WNT5B |
| ATP6V1G2 | COL18A1 | EPRS | HADH | IL6 | MRLC2 | PLEKHC1 | RPL12 | TARS | XPO1 |
| B2M | COL1A1 | ESD | HARS | IL6ST | MSN | PLOD1 | RPL14 | TCN2 | YKT6 |
| B4GALT1 | COL1A2 | ETF1 | HARS2 | IL8 | MTAP | PLOD2 | RPL18 | TCP1 | YWHAB |
| BASP1 | COL2A1 | ETFB | hCG_1641617 | ILF2 | MTPN | PLOD3 | RPL22 | TFPI | YWHAE |
| BAT1 | COL3A1 | ETHE1 | hCG_2023776 | ILF3 | MVP | PLS1 | RPL30 | TGFB1 | YWHAG |
| BBS1 | COL4A1 | EXT1 | HEXA | INHBA | MXRA5 | PLS3 | RPL5 | TGFB2 | YWHAH |
| BCAT1 | COL4A2 | FAH | HEXB | IQGAP1 | MXRA8 | PLSCR3 | RPL7 | TGFBI | YWHAQ |
| BGN | COL5A1 | FAHD1 | HGF | ISOC1 | MYH11 | POSTN | RPLP0 | THBS | YWHAZ |
| BLVRA | COL5A2 | FAM129B | HIBCH | ITGA2 | MYH14 | PPCS | RPLP1 | THBS1 | |

Of the above proteins in Table E2, TIMP1, TIMP2, TNFRSF11B, LGALS3, ALCAM, DCN, SFRP1, GDF15, PDGFC, PTX3, LTBP1, IGFBP2, GREM1, IGFBP7, MIF, MMP1, PLAU, INHBA and THBS1 were identified by LC MS/MS and antibody array, PPIA, HIST1H4, PPIB, HIST1H4A, HIST1H4B, HIST1H4C, HIST1H4D, HIST1H4E, HIST1H4F, HIST1H4H, HIST1H4I, HIST1H4J, HIST1H4K, HIST1H4L, HIST2H2AA3, HIST2H2AA4, HIST2H4A, HIST2H4B, HIST4H4, HLA-A, HLA-B, SDCBP, TUBA1A, TUBAE, TUBA8, GAPDH, TUBB, TUBB2C, TUBB3, TUBB4, TUBB6, TUBB8, HSP90AB1, ANXA1, HSP90B1, ANXA2, ANXA5, ANXA6, PDCD6IP, CD9, CFL1, CLTC, ENOL, PKM2, MSN, and YWHAG are identified by LC MS/MS and at least 4 studies on exosomes secreted by cultured cells. FGF16, FGFRL1, TNFRSF12A, TNFSF12, CXCL1, CCL18, CXCL12, CCL2, CXCL16, CCL7, CXCL2, CCN4, CXCL9, CCR4, CCR5, ANGPT4, GDF1, GDF11, SFRP4, GDF3, GDF5, GDF8, DKK1, LTA, PDGFA, LTB, MADH4, IFNG . . . , GPC5, IGF2R, CHRDL1, GRN, VEGFC, IL13, IL15, EML2, IL15RA, IL1RAP, MMP10, IL2, GZMA, IL21R, IL3, IL6, IL6ST, IL8, HGF and THBS are identified by antibody array. The remaining proteins are identified by LC MS/MS.

Example 41

Results: Exosome-Associated Proteins are Localized in Phospholipid Vesicles

Figure 16:
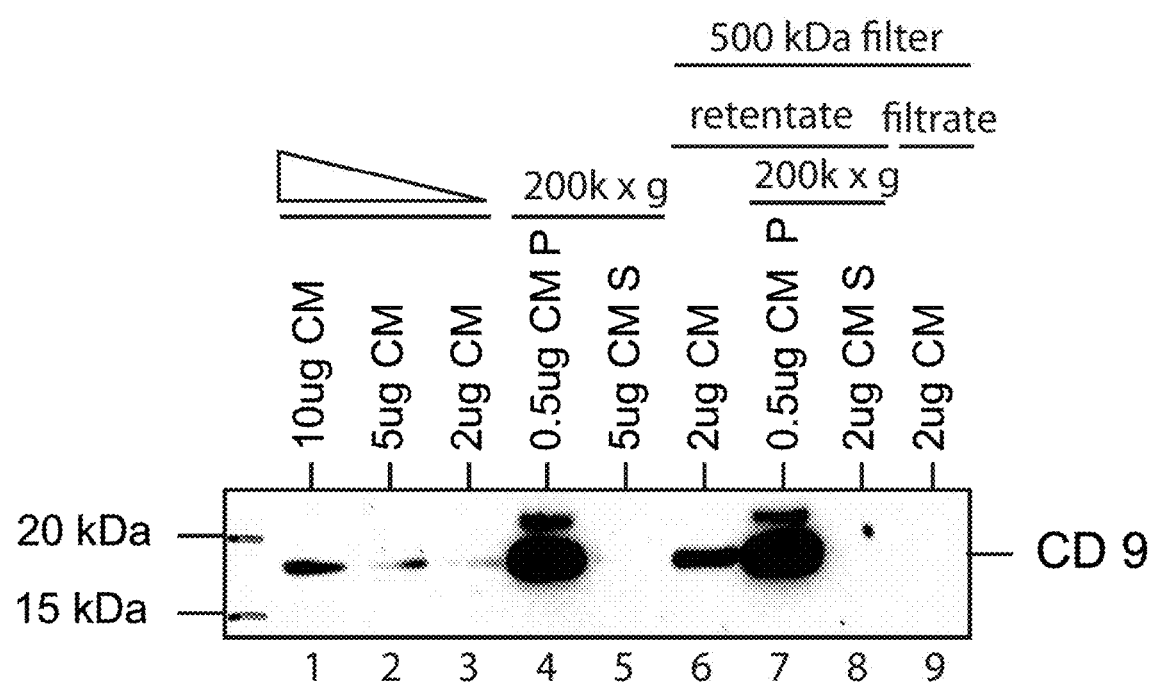
FIG. 16 shows Ultracentrifugation of CM. CM was concentrated five times by filtering through a membrane with MWCO of 500 kDa. The retentate, and the unfiltered CM were ultracentrifuged at 200,000 g for 2 hour. The supernatant and the pellet were analysed by western blotting for the presence of CD9. Lane 1-3: different protein concentration of CM. Lane 4 and 5: The pellet (P) and supernatant (S) after ultracentrifugation of unfiltered CM. Lane 6: Retentate after filtration of CM through a membrane with MWCO of 500 kDa. Lane 7-8: The pellet (P) and supernatant (S) after ultracentrifugation of retentate. Lane 9: Filtrate after filtration of CM through a membrane with MWCO of 500 kDa.

To verify the presence of exosome in the CM, the CM is ultracentrifuged at 200,000 g for two hours. There is a >200 fold enrichment of CD9 an exosome-associated protein in the pellet with no detectable level of CD9 in the supernatant (FIG. 16). Ultracentrifugation at 100,000 g for one hour is not sufficient to sediment all the CD9 (FIG. 16). Filtration of the CM through a filter with a MWCO of 500 kDa followed by centrifugation of either the filtrate or retentate at 200,000 g for 2 hours generated a pellet in the retentate fraction (FIG. 16). CD9 which had MW of 19 kDa respectively are highly enriched in this pellet. However, this pellet did not confer any cardioprotection in a mouse model of ischemia/reperfusion injury and we postulated that this is due to the need for vigorous vortexing and pipetting to resuspend the pellet. We observed that only a fraction of CD9 sedimented at 100,000 g and 200,000 g for one hour and most sedimented at 200,000 g for two hours. A small fraction sedimented at 200,000 g for four hours. Together, these observations support our hypothesis that the active component is relatively large complex that can be sedimented by ultracentrifugation.

Figure 17:
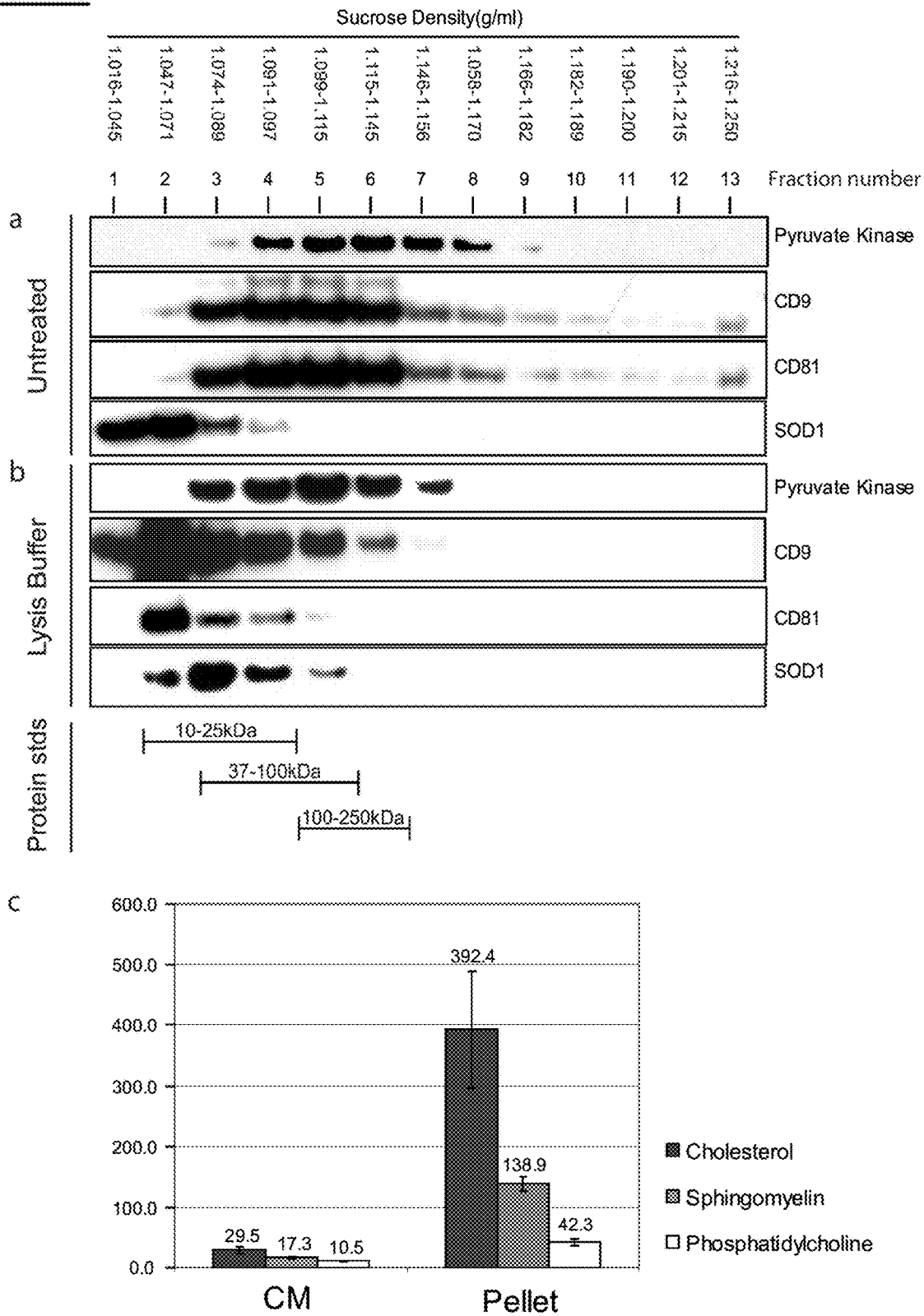
FIGS. 17A-17C show Fractionation on sucrose gradient density. A sucrose density gradient was prepared by layering 14 sucrose solutions of concentrations from 22.8-60% (w/v) in a SW60Ti centrifuge tube with the most concentrated solution at the bottom of the ultracentrifuge tube. The sample was loaded on top of the gradient and ultracentrifuged for 16.5 hours at 200,000×g, 4° C. in a SW60Ti rotor (Beckman Coulter Inc.). 13 fractions were collected from top to the bottom of the sucrose gradient. The density of each fraction was calculated by weighing a fixed volume of each fraction. The fractions were then analysed by western blot analysis and probed for pyruvate kinase, CD9, CD81 and SOD1. Protein standard molecular weight markers were fractionated on a similar gradient and the distribution of the markers in the different fractions of the sucrose gradient were denoted at the bottom of the figure.

To confirm that the exosome-associated proteins are indeed in exosomes i.e. phospholipid vesicles, the CM is fractionated on a sucrose density gradient by equilibrium ultracentrifugation. Like lipid vesicles, the density of exosomes ranges from 1.13 g ml$^{-1}$ to 1.19 g ml-1 and float on sucrose gradients. Flotation on sucrose gradients readily separate exosomes from contaminating material such as protein aggregates or nucleosomal fragments (Thery et al., 2002). Fractions from the sucrose gradient are then analysed for the presence CD9, CD81, Tsp1, SOD-1 and pyruvate kinase along the gradient (FIG. 17A). A notable feature is that the proteins did not sediment to the expected density of proteins that is correlated to their molecular weight. To determine if these apparent densities are due to the proteins being contained in lipid vesicles, CM is treated with a cell lysis buffer (FIG. 17B) before being fractionated on a sucrose density gradient. This pre-treatment with a plasma membrane solubilization reagent restored each of the apparent densities to the expected density of proteins that correlated to their molecular weight. Therefore, the exosome-associated proteins are localized in lipid vesicles, consistent with our exosome hypothesis.

To confirm that there are lipid vesicles in the CM, the concentration of sphingomyelin and phosphatidylcholine, the major phospholipids of the plasma membrane, and cholesterol is determined (FIG. 17C). As expected, the relative concentration of these lipids per µg protein is higher in the CM relative to the non-conditioned medium. Furthermore, ultracentrifugation of the CM at 200,000 g for 2 hours significantly increased the concentration of the lipids (FIG. 17C).

Example 42

Results: Exosomal Proteins are Either Membrane Bound or Encapsulated

Figure 18:
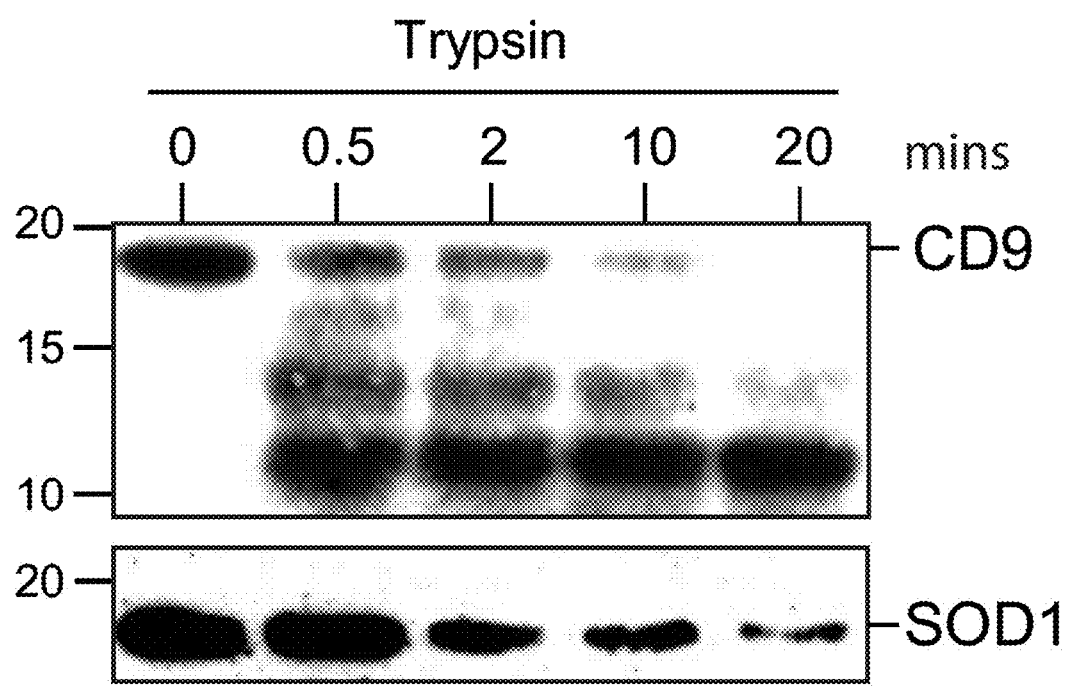
FIG. 18 shows Trypsinization of CM. CM was digested with trypsin for 0, 0.5, 2, 10 and 20 mins. The partially digested CM was analysed for the presence of CD9 and SOD1.

As the exosome-associated proteins include many known membrane proteins such as CD9 and cytosolic proteins such as SOD1, we therefore determined if these proteins are similarly localized on the lipid membrane and lumen of the vesicles. CM is subjected to limited trypsinization over time (FIG. 18A). CD9 which has a similar MW as SOD1 is relatively more susceptible to trypsin digest than SOD1. Digestion of SOD1 is observed only after more than 50% of CD9 had been digested (FIG. 18A). Unlike tryptic digestion of SOD1 which generated no detectable intermediates, tryptic digestion of CD9 generated three tryptic peptide intermediates, suggesting that CD9 has domains with different trypsin-sensitivity. Based on the length of peptide intermediates and known tryptic sites of CD9, the three susceptible tryptic peptide intermediates are mapped to the transmembrane or cytoplasmic domains. This suggested that the known extra-cytoplasmic domain of cellular CD9 is similarly exposed on the secreted CD9 and therefore trypsin-sensitive while the trans-membrane and cytoplasmic domain is not exposed and is therefore relatively resistant to tryptic digest. Together, these observations suggested that CD9, a known membrane protein is also membrane-bound in the exosome and is oriented in the same direction as CD9 in the plasma membrane while cytosolic SOD-1 is localized in the lumen and could be digested only when the integrity of the membrane is compromised by the digestion of membrane proteins.

Example 43

Results: Presence of Lipid Vesicle Encapsulated RNA in the Secretion of MSCs

Figure 19:
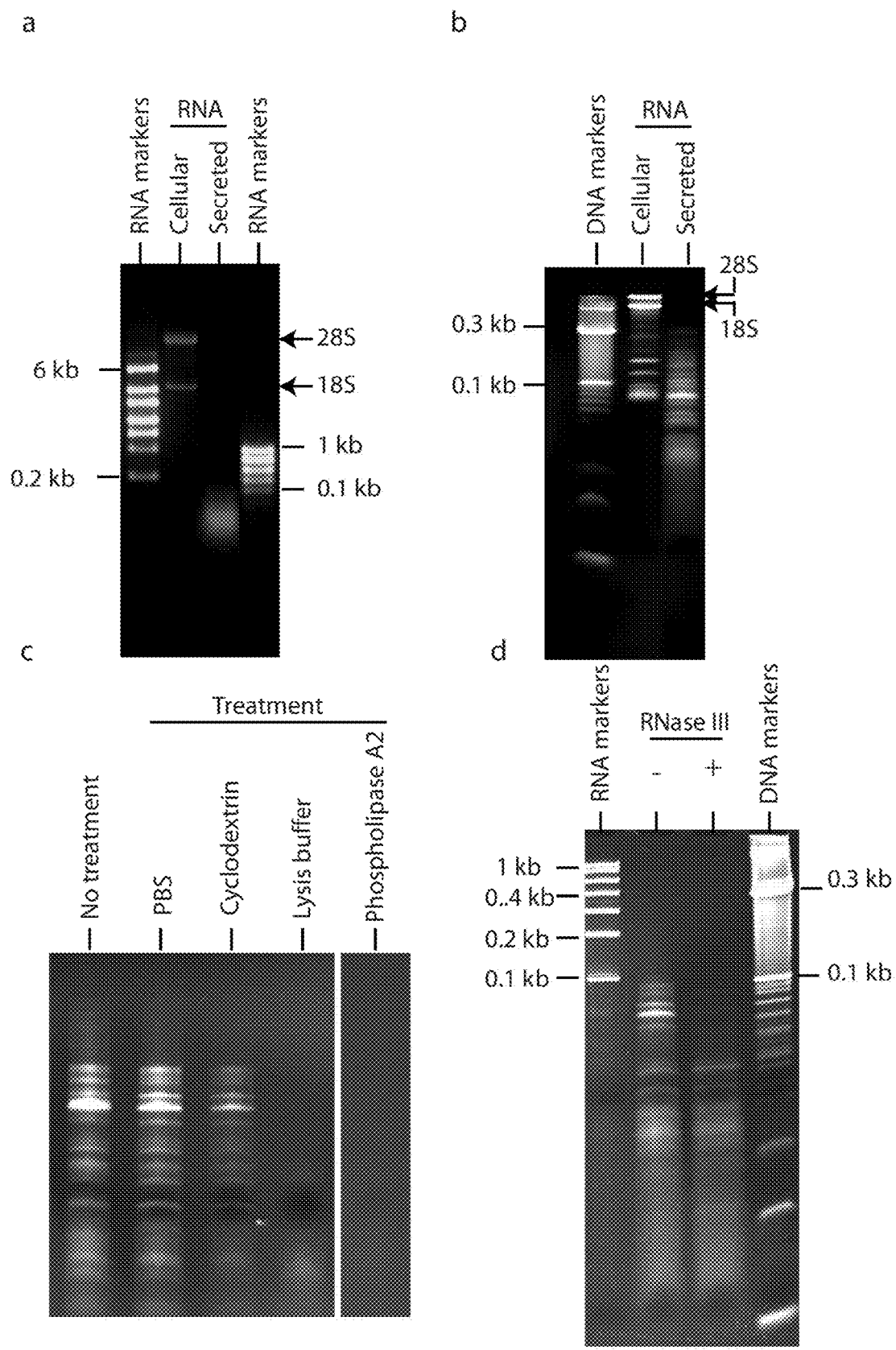
FIGS. 19A-19D show Analysis of RNA in the CM.

It is previously reported that RNAs are secreted by cells in exosomes (Smalheiser, 2007; Taylor and Gercel-Taylor, 2008; Valadi et al., 2007). To determine if RNA is present in the cardioprotective secretion, CM is extracted for RNA by Trizol to yield 5-6 ug RNA per mg protein. When separated on a glyoxal-agarose gel (FIG. 19A) or an urea-PAGE (FIG. 19B), the RNA contained undetectable level of 18S and 28S ribosomal RNA with most RNAs being <300 nt. To determine if the stability of the RNA in the secretion is due to its encapsulation within as a phospholipid vesicle as observed for the proteins, the CM is treated with RNase before being extracted for RNA. The RNA yield and the size distribution are similar to that of untreated CM (FIG. 19C), suggesting that the secreted RNAs are protected from RNAse degradation. We next tested the possibility that the RNAs are protected by a lipid membrane, analogous to a cell membrane by treating the CM with a SDS-based cell lysis buffer, cylcodextrin or phospholipase A2. After treatment with one of the four reagents, the CM is exposed to RNAse and then extracted for RNA. Pretreatment with a SDS-based cell lysis buffer resulted in a complete loss of RNAs while treatment with cylcodextrin or phospholipase A2 led to partial degradation and loss of RNAs. These observations suggested that the RNA is protected from RNAse activity by a cholesterol-rich phospholipid membrane such that the membrane is readily dissolved or compromised by a SDS-based cell lysis buffer, a detergent such as TritonX-100 that dissolves lipids, cylcodextrin that chelates and extracts cholesterol or degradation by phospholipase D. We also observed that RNAs of ~70-100 nt are more sensitive to RNAse III activity than those of smaller MW, suggesting that the larger RNAs are double stranded (FIG. 19D).

Example 44

Results: Secreted RNAs are Sequestered in Vesicles

Figure 20:
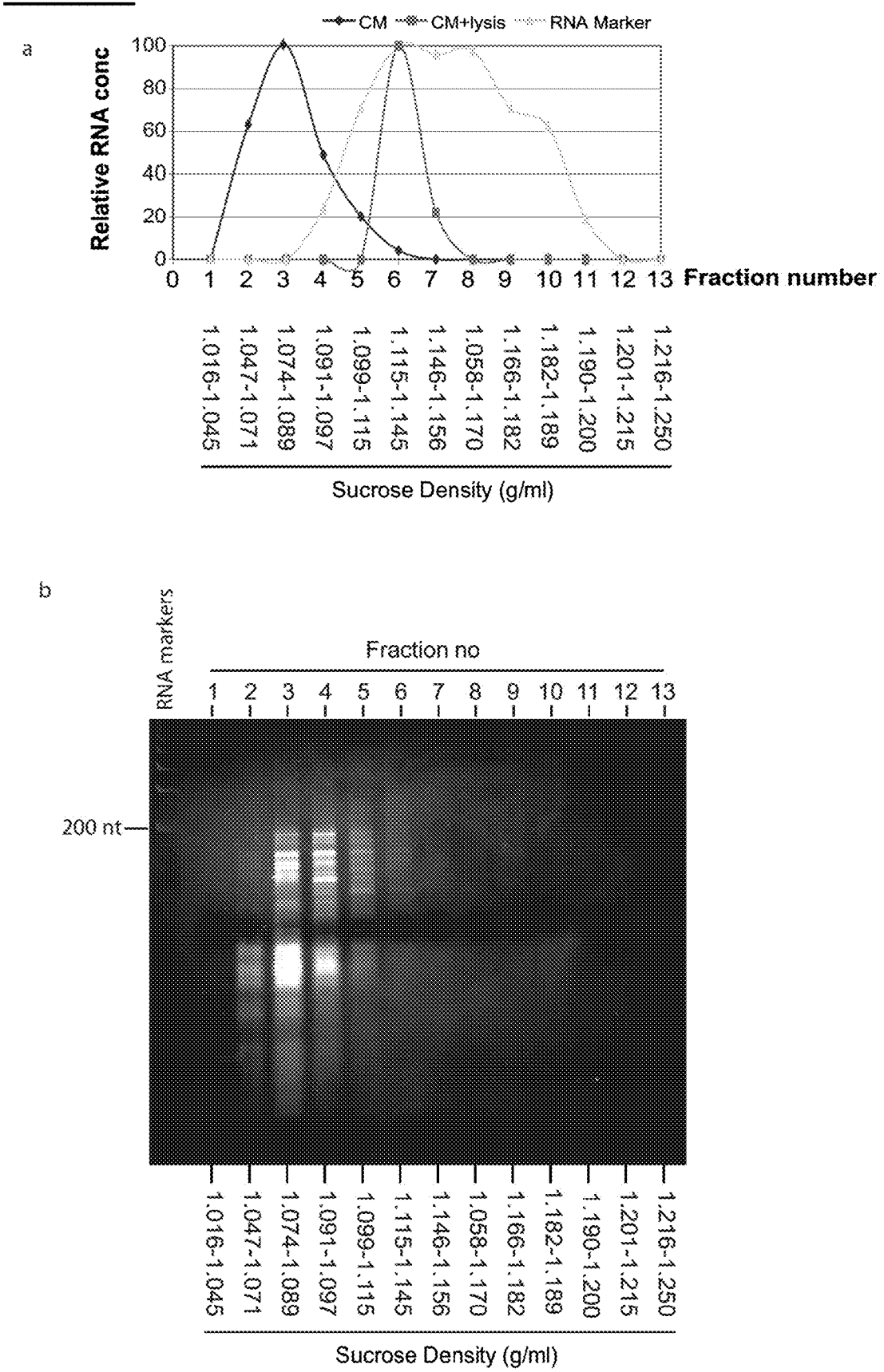
FIGS. 20A-20B show Density of RNA in the CM. After fractionation of CM, CM pretreated with lysis buffer and RNA MW standards on a sucrose density gradient equilibrium centrifugation as described in FIGS. 4A-4E, each fraction was extracted for RNA.

Since the RNAs are shown to be in lipid vesicles, we next determined the buoyant density of these vesicles using sucrose gradient equilibrium ultracentrifugation. CM, CM pretreated with lysis buffer or a set of RNA MW markers is loaded onto a sucrose density gradient and ultracentrifuged as described in FIG. 4a, b. The gradients are then removed in thirteen fractions and each fraction is then extracted for RNA. The secreted RNAs equilibrated at a density of 1.074-1.1170 g/ml (FIG. 20). In contrast, RNA MW markers exhibited a buoyant density of 1.115-1.1170 g/ml and pretreatment of the CM with lysis buffer before centrifugation caused an increase in density of the secreted RNA to that of RNA MW markers i.e. 1.115-1.145 g/ml (FIG. 20C). These observations are therefore consistent with the RNAs being encapsulated in a lipid vesicle and thus had an apparent density that is much lower than soluble RNA. Pretreatment of the CM with lysis buffer released the RNA and resulted in the RNA sedimenting at the density of RNA markers.

Example 45

Results: RNA-containing Vesicles are not in CD81 Containing Exosomes

Figure 21:
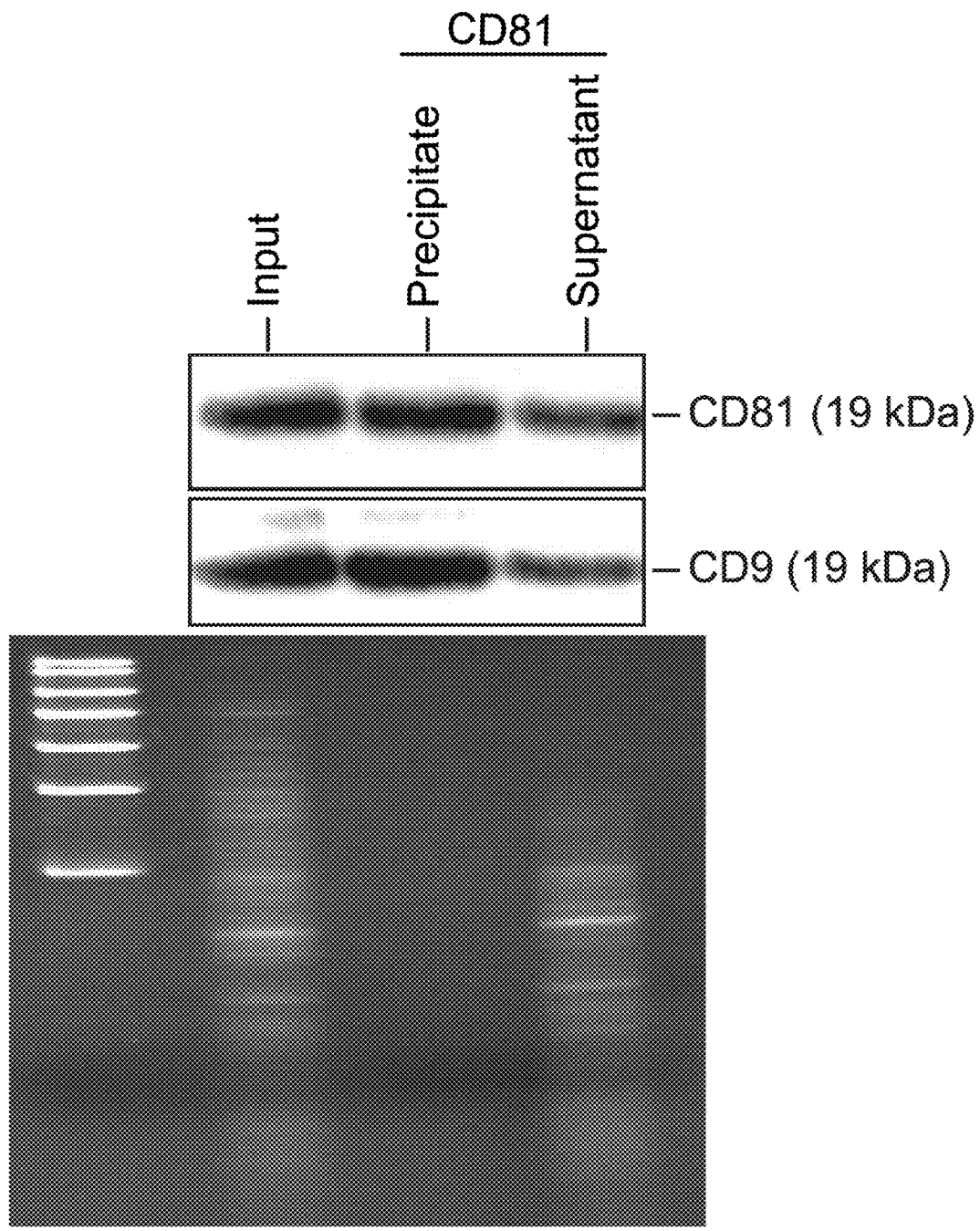
FIG. 21 shows RNA was not in CD81+ exosomes. CD81 immunoprecipitation which also precipitated CD9 was performed as described in FIG. 2. The immunoprecipitate and the supernatant were extracted for RNA and the extracts were separated on a urea-PAGE and visualized by ethidium bromide staining.

As shown above, CD9, CD81 and Alix are co-immunoprecipitated by anti CD81 antibodies. Here we tested if the RNA also immunoprecipitate with CD81. After immunoprecipitation, the RNA is not present in the precipitate but remained in the supernatant (FIG. 21). Therefore, the secreted RNAs are not sequestered in CD81+, CD81+ CD9+, or CD81+ CD9+ Alix+ vesicles.

Example 46

Results: Secreted RNA Contain microRNAs that Include pre-miRNAs

Figure 22:
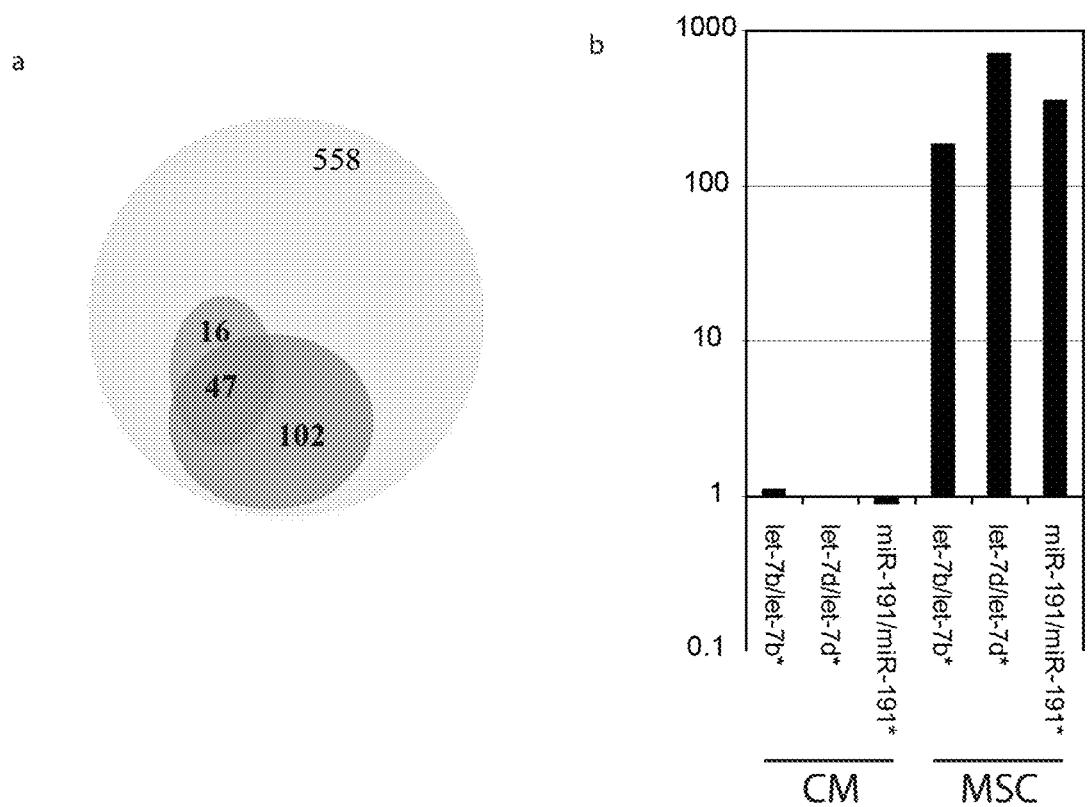
FIGS. 22A-22B show Microarray analysis of miRNA in the CM. RNA samples from MSC and the CM were hybridized to microarray chips containing probes for miRNA transcripts listed in Sanger miRBase Release 10.1. The hybridization was performed using two biological replicates of each RNA samples.

It has been reported that exosomes contain microRNAs (Smalheiser, 2007; Taylor and Gercel-Taylor, 2008; Valadi et al., 2007) and as most of the RNAs in the CM are less than 300 nt, we tested the RNA from the MSC and their CM for the presence of microRNAs (miRNAs) by performing a microarray hybridization. 149 miRNA are detected in MSC and 63 are detected in the CM (FIG. 22A, Table E3 below).

TABLE E3

List of miRNAs in MSC and CM as determined by microarray hybridization.

| | | | | | |
|---|---|---|---|---|---|
| hsa-let-7a | hsa-miR-24-2* | hsa-miR-98 | hsa-miR-149* | hsa-miR-214 | hsa-miR-484 |
| hsa-let-7b | hsa-miR-25 | hsa-miR-99a | hsa-miR-151-3p | hsa-miR-221 | hsa-miR-491-5p |
| hsa-let-7c | hsa-miR-26a | hsa-miR-99b | hsa-miR-151-5p | hsa-miR-222 | hsa-miR-503 |
| hsa-let-7d | hsa-miR-26b | hsa-miR-100 | hsa-miR-152 | hsa-miR-320 | hsa-miR-505* |
| hsa-let-7e | hsa-miR-27a | hsa-miR-103 | hsa-miR-155 | hsa-miR-324-5p | hsa-miR-532-5p |
| hsa-let-7f | hsa-miR-27b | hsa-miR-106a | hsa-miR-181a | hsa-miR-328 | hsa-miR-574-3p |
| hsa-let-7g | hsa-miR-27b* | hsa-miR-106b | hsa-miR-181a* | hsa-miR-330-3p | hsa-miR-574-5p |
| hsa-let-7i | hsa-miR-28-3p | hsa-miR-107 | hsa-miR-181a-2* | hsa-miR-331-3p | hsa-miR-575 |
| hsa-miR-10a | hsa-miR-28-5p | hsa-miR-125a-3p | hsa-miR-181b | hsa-miR-335 | hsa-miR-584 |
| hsa-miR-15a | hsa-miR-29a | hsa-miR-125a-5p | hsa-miR-181c | hsa-miR-342-3p | hsa-miR-612 |
| hsa-miR-15b | hsa-miR-29c | hsa-miR-125b | hsa-miR-181d | hsa-miR-345 | hsa-miR-625 |
| hsa-miR-16 | hsa-miR-30a | hsa-miR-126 | hsa-miR-185 | hsa-miR-361-5p | hsa-miR-629 |
| hsa-miR-17 | hsa-miR-30a* | hsa-miR-128 | hsa-miR-186 | hsa-miR-362-3p | hsa-miR-638 |
| hsa-miR-18a | hsa-miR-30b | hsa-miR-130a | hsa-miR-187* | hsa-miR-362-5p | hsa-miR-663 |
| hsa-miR-18b | hsa-miR-30c | hsa-miR-130b | hsa-miR-191 | hsa-miR-365 | hsa-miR-671-5p |
| hsa-miR-19b | hsa-miR-30d | hsa-miR-132 | hsa-miR-191* | hsa-miR-374b | hsa-miR-708 |
| hsa-miR-20a | hsa-miR-30e | hsa-miR-137 | hsa-miR-192 | hsa-miR-421 | hsa-miR-744 |

TABLE E3-continued

List of miRNAs in MSC and CM as determined by microarray hybridization.

| | | | | | |
|---|---|---|---|---|---|
| hsa-miR-20b | hsa-miR-30e* | hsa-miR-140-3p | hsa-miR-193a-5p | hsa-miR-423-5p | hsa-miR-766 |
| hsa-miR-21 | hsa-miR-31 | hsa-miR-143 | hsa-miR-195 | hsa-miR-424 | hsa-miR-768-3p |
| hsa-miR-22 | hsa-miR-31* | hsa-miR-145 | hsa-miR-197 | hsa-miR-424* | hsa-miR-768-5p |
| hsa-miR-22* | hsa-miR-34a | hsa-miR-145* | hsa-miR-199a-3p | hsa-miR-425 | hsa-miR-769-5p |
| hsa-miR-23a | hsa-miR-34a* | hsa-miR-146a | hsa-miR-199a-5p | hsa-miR-425* | hsa-miR-877 |
| hsa-miR-23a* | hsa-miR-92a | hsa-miR-146b-5p | hsa-miR-199b-5p | hsa-miR-454 | hsa-miR-923 |
| hsa-miR-23b | hsa-miR-92b | hsa-miR-148b | hsa-miR-210 | hsa-miR-455-3p | hsa-miR-940 |
| hsa-miR-24 | hsa-miR-93 | hsa-miR-149 | hsa-miR-212 | hsa-miR-483-5p | |
| hsa-let-7b* | hsa-miR-124 | hsa-miR-296-5p | hsa-miR-765 | hsa-miR-1228 | hsa-miR-1238 |
| hsa-let-7d* | hsa-miR-150* | hsa-miR-493* | hsa-miR-933 | hsa-miR-1234 | |
| hsa-miR-122 | hsa-miR-198 | hsa-miR-572 | hsa-miR-1224-5p | hsa-miR-1237 | |

47 miRNAs are present in both MSC and CM. These are: hsa-let-7a, hsa-miR-149*, hsa-miR-214, hsa-let-7b, hsa-miR-221, hsa-let-7c, hsa-miR-26a, hsa-miR-151-5p, hsa-miR-222, hsa-let-7d, hsa-miR-100, hsa-miR-320, hsa-let-7e, hsa-miR-103, hsa-let-7f, hsa-miR-181a, hsa-miR-574-3p, hsa-miR-574-5p, hsa-let-7i, hsa-miR-107, hsa-miR-575, hsa-miR-125a-5p, hsa-miR-125b, hsa-miR-361-5p, hsa-miR-638, hsa-miR-663, hsa-miR-191, hsa-miR-671-5p, hsa-miR-132, hsa-miR-191*, hsa-miR-193a-5p, hsa-miR-423-5p, hsa-miR-21, hsa-miR-31, hsa-miR-143, hsa-miR-22, hsa-miR-145, hsa-miR-23a, hsa-miR-146a, hsa-miR-425*, hsa-miR-92a, hsa-miR-923, hsa-miR-23b, hsa-miR-940, hsa-miR-24, hsa-miR-149 and hsa-miR-483-5p.

16 miRNAs are detectable in the CM but are present at below detection level in MSCs. These are: hsa-let-7b*, hsa-miR-124, hsa-miR-296-5p, hsa-miR-765, hsa-miR-1228, hsa-miR-1238, hsa-let-7d*, hsa-miR-150*, hsa-miR-493*, hsa-miR-933, hsa-miR-1234, hsa-miR-122, hsa-miR-198, hsa-miR-572, hsa-miR-1224-5p an dhsa-miR-1237.

The following miRNAs are present in MSC only: hsa-miR-24-2*, hsa-miR-98, hsa-miR-484, hsa-miR-25, hsa-miR-99a, hsa-miR-151-3p, hsa-miR-491-5p, hsa-miR-99b, hsa-miR-503, hsa-miR-26b, hsa-miR-152, hsa-miR-505*, hsa-miR-27a, hsa-miR-155, hsa-miR-324-5p, hsa-miR-532-5p, hsa-miR-27b, hsa-miR-106a, hsa-miR-328, hsa-let-7g, hsa-miR-27b*, hsa-miR-106b, hsa-miR-181a*, hsa-miR-330-3p, hsa-miR-28-3p, hsa-miR-181a-2*, hsa-miR-331-3p, hsa-miR-10a, hsa-miR-28-5p, hsa-miR-125a-3p, hsa-miR-181b, hsa-miR-335, hsa-miR-584, hsa-miR-15a, hsa-miR-29a, hsa-miR-181c, hsa-miR-342-3p, hsa-miR-612, hsa-miR-15b, hsa-miR-29c, hsa-miR-181d, hsa-miR-345, hsa-miR-625, hsa-miR-16, hsa-miR-30a, hsa-miR-126, hsa-miR-185, hsa-miR-629, hsa-miR-17, hsa-miR-30a*, hsa-miR-128, hsa-miR-186, hsa-miR-362-3p, hsa-miR-18a, hsa-miR-30b, hsa-miR-130a, hsa-miR-187*, hsa-miR-362-5p, hsa-miR-18b, hsa-miR-30c, hsa-miR-130b, hsa-miR-365, hsa-miR-19b, hsa-miR-30d, hsa-miR-374b, hsa-miR-708, hsa-miR-20a, hsa-miR-30e, hsa-miR-137, hsa-miR-192, hsa-miR-421, hsa-miR-744, hsa-miR-20b, hsa-miR-30e*, hsa-miR-140-3p, hsa-miR-766, hsa-miR-195, hsa-miR-424, hsa-miR-768-3p, hsa-miR-31*, hsa-miR-197, hsa-miR-424*, hsa-miR-768-5p, hsa-miR-22*, hsa-miR-34a, hsa-miR-145*, hsa-miR-199a-3p, hsa-miR-425, hsa-miR-769-5p, hsa-miR-34a*, hsa-miR-199a-5p, hsa-miR-877, hsa-miR-23a*, hsa-miR-146b-5p, hsa-miR-199b-5p, hsa-miR-454, hsa-miR-92b, hsa-miR-148b, hsa-miR-210, hsa-miR-455-3p, hsa-miR-93, hsa-miR-212.

The microarray analysis also indicated that the CM contained significant levels of anti-guide miRNA (denoted with an asterisk). For example, the relative ratios of let7b to let7b*, let7d to let7d* and miR-191 to miR-191* in CM are much reduced compared to that in the MSCs (FIG. 22B). In cells, cleavage of the stem-loop pre-miRNA generates the mature guide miRNA and the anti-guide miRNA*. The latter is usually degraded in the cell. One possible explanation for the low ratio of guide miRNA to anti-guide miRNA is that microRNAs in the secretion are pre-miRNAs, and not mature RNAs. Consistent with the possibility is our observations that the 70-100 nt RNAs are double-stranded (FIG. 19D). To confirm this finding, real time PCR analysis of reverse transcribed RNAs are performed using primers specific for guide mRNA and pre-miRNA with or without prior treatment with RNAse III. RNAse III treatment will confirm the presence of pre-miRNA by degrading the pre-miRNA and render it undetectable by RT-PCR.

Example 47

Results: Cardioprotective Secretion Contains Only Particles with Hydrodynamic Radius of 45-55 nm in the Detectable Range of 1-1000 nm To confirm that the secretion contained large complexes, CM and NCM is first separated by size exclusion on a HPLC (FIG. 13) and each eluting peak as measured by absorbance at 220 nm is then examined for dynamic light scattering (DLS) using a quasi-elastic light scattering (QELS) detector.

Only one eluting peak with a retention time of 11-13 minutes exhibited dynamic light scattering and the $r_h$ of particles in this peak is about 45-55 nm. The other eluting peaks with a retention time of 13-16 and 17-19 minutes did not exhibit dynamic light scattering. Since the $r_h$ detection range of DLS is from 1 to 1000 nm in and the diameter of a DNA alpha helix is 2 nm, globular proteins is 1-10 nm, nuclear pore (50 nm), large virus (100 nm) and mitochondrion is 3 μM, DLS is therefore capable of detecting most biological particles.

Based on our observation that that cardioprotection is associated with a fraction that has MW of >1000 kDa, we hypothesize that the eluting peak at a retention time of 12 minutes is the active component.

To confirm this, this eluting peak are harvested and tested in a mouse model of myocardial ischemia/reperfusion injury as previously described above and in (Timmers et al., 2008).

REFERENCES (INCLUDING FOR EXAMPLES 1 TO 18)

1. Lewis E F, Moye L A, Rouleau J L, et al. Predictors of late development of heart failure in stable survivors of myocardial infarction: the CARE study. *J Am Coll Cardiol*. Oct. 15, 2003; 42(8):1446-1453.
2. Kleiman N S, White H D, Ohman E M, et al. Mortality within 24 hours of thrombolysis for myocardial infarction. The importance of early reperfusion. The GUSTO Investigators, Global Utilization of Streptokinase and Tissue Plasminogen Activator for Occluded Coronary Arteries. *Circulation*. December 1994; 90(6):2658-2665.
3. Saraste A, Pulkki K, Kallajoki M, et al. Apoptosis in human acute myocardial infarction. *Circulation*. Jan. 21, 1997; 95(2):320-323.
4. Smits A M, van Vliet P, Hassink R J, et al. The role of stem cells in cardiac regeneration. *J Cell Mol Med*. January-March 2005; 9(1):25-36.
5. Menasche P, Hagege A A, Vilquin J T, et al. Autologous skeletal myoblast transplantation for severe postinfarction left ventricular dysfunction. *J Am Coll Cardiol*. Apr. 2, 2003; 41(7):1078-1083.
6. Perin E C, Dohmann H F, Borojevic R, et al. Transendocardial, autologous bone marrow cell transplantation for severe, chronic ischemic heart failure. *Circulation*. May 13, 2003; 107(18):2294-2302.
7. Shake J G, Gruber P J, Baumgartner W A, et al. Mesenchymal stem cell implantation in a swine myocardial infarct model: engraftment and functional effects. *Ann Thorac Surg*. June 2002; 73(6):1919-1925; discussion 1926.
8. Strauer B E, Brehm M, Zeus T, et al. Repair of infarcted myocardium by autologous intracoronary mononuclear bone marrow cell transplantation in humans. *Circulation*. Oct. 8, 2002; 106(15):1913-1918.
9. Pittenger M F, Martin B J. Mesenchymal stem cells and their potential as cardiac therapeutics. *Circ Res*. Jul. 9, 2004; 95(1):9-20.
10. Minguell J J, Erices A. Mesenchymal stem cells and the treatment of cardiac disease. *Exp Biol Med (Maywood)*. January 2006; 231(1):39-49.
11. Zimmet J M, Hare J M. Emerging role for bone marrow derived mesenchymal stem cells in myocardial regenerative therapy. *Basic Res Cardiol*. November 2005; 100(6): 471-481.
12. Caplan A I, Dennis J E. Mesenchymal stem cells as trophic mediators. *J Cell Biochem*. Aug. 1, 2006; 98(5): 1076-1084.
13. Gnecchi M, He H, Liang O D, et al. Paracrine action accounts for marked protection of ischemic heart by Akt-modified mesenchymal stem cells. *Nat Med*. April 2005; 11(4):367-368.
14. Gnecchi M, He H, Noiseux N, et al. Evidence supporting paracrine hypothesis for Akt-modified mesenchymal stem cell-mediated cardiac protection and functional improvement. *Faseb J*. April 2006; 20(6):661-669.
15. Lian Q, Lye E, Suan Yeo K, et al. Derivation of clinically compliant MSCs from CD105+, CD24− differentiated human ESCs. *Stem Cells*. February 2007; 25(2):425-436.
16. Sze S K, de Kleijn D P, Lai R C, et al. Elucidating the secretion proteome of human ESC-derived mesenchymal stem cells. *Mol Cell Proteomics*. Jun. 11, 2007.
17. Birnbaum Y, Hale S L, Kloner R A. Differences in reperfusion length following 30 minutes of ischemia in the rabbit influence infarct size, as measured by triphenyltetrazolium chloride staining. *J Mol Cell Cardiol*. February 1997; 29(2):657-666.
18. Timmers L, Sluijter J P, Verlaan C W, et al. Cyclooxygenase-2 inhibition increases mortality, enhances left ventricular remodeling, and impairs systolic function after myocardial infarction in the pig. *Circulation*. Jan. 23, 2007; 115(3):326-332.
19. Steendijk P, Baan J, Jr., Van der Velde E T, et al. Effects of critical coronary stenosis on global systolic left ventricular function quantified by pressure-volume relations during dobutamine stress in the canine heart. *J Am Coll Cardiol*. September 1998; 32(3):816-826.
20. Hausenloy D J, Yellon D M. New directions for protecting the heart against ischaemia-reperfusion injury: targeting the Reperfusion Injury Salvage Kinase (RISK)-pathway. *Cardiovasc Res*. Feb. 15, 2004; 61(3):448-460.
21. Dumont E A, Reutelingsperger C P, Smits J F, et al. Real-time imaging of apoptotic cell-membrane changes at the single-cell level in the beating murine heart. *Nat Med*. December 2001; 7(12):1352-1355.
22. Eefting F, Rensing B, Wigman J, et al. Role of apoptosis in reperfusion injury. *Cardiovasc Res*. Feb. 15, 2004; 61(3):414-426.
23. Mirotsou M, Zhang Z, Deb A, et al. Secreted frizzled related protein 2 (Sfrp2) is the key Akt-mesenchymal stem cell-released paracrine factor mediating myocardial survival and repair. *Proc Natl Acad Sci USA*. Jan. 30, 2007; 104(5):1643-1648.
24. Dhalla N S, Elmoselhi A B, Hata T, et al. Status of myocardial antioxidants in ischemia-reperfusion injury. *Cardiovasc Res*. Aug. 18, 2000; 47(3):446-456.
25. Redondo S, Ruiz E, Santos-Gallego C G, et al. Pioglitazone induces vascular smooth muscle cell apoptosis through a peroxisome proliferator-activated receptor-gamma, transforming growth factor-beta1, and a Smad2-dependent mechanism. *Diabetes*. March 2005; 54(3):811-817.
26. Bolli R, Zughaib M, Li X Y, et al. Recurrent ischemia in the canine heart causes recurrent bursts of free radical production that have a cumulative effect on contractile function. A pathophysiological basis for chronic myocardial "stunning" *J Clin Invest*. August 1995; 96(2):1066-1084.
27. Dai W, Hale S L, Kloner R A. Role of a paracrine action of mesenchymal stem cells in the improvement of left ventricular function after coronary artery occlusion in rats. *Regen Med*. January 2007; 2(1):63-68.
28. Bolli R, Becker L, Gross G, et al. Myocardial protection at a crossroads: the need for translation into clinical therapy. *Circ Res*. Jul. 23, 2004; 95(2):125-134.

REFERENCES (INCLUDING FOR EXAMPLES 19 TO 30)

1. Le Blanc K, Pittenger M. Mesenchymal stem cells: progress toward promise. Cytotherapy. 2005; 7(1):36-45.
2. Reiser J, Zhang X Y, Hemenway C S, Mondal D, Pradhan L, La Russa V F. Potential of mesenchymal stem cells in gene therapy approaches for inherited and acquired diseases. Expert Opin Biol Ther. 2005; 5(12):1571-1584.
3. Hui J H, Ouyang H W, Hutmacher D W, Goh J C, Lee E H. Mesenchymal stem cells in musculoskeletal tissue engineering: a review of recent advances in National University of Singapore. Ann Acad Med Singapore. 2005; 34(2):206-212.
4. Caplan A I. Review: mesenchymal stem cells: cell-based reconstructive therapy in orthopedics. Tissue Eng. 2005; 11(7-8):1198-1211.
5. Menasche P. The potential of embryonic stem cells to treat heart disease. Curr Opin Mol Ther. 2005; 7(4):293-299.
6. Laflamme M A, Murry C E. Regenerating the heart. Nat Biotechnol. 2005; 23(7):845-856.
7. Caplan A I, Dennis J E. Mesenchymal stem cells as trophic mediators. J Cell Biochem. 2006.
8. Kinnaird T, Stabile E, Burnett M S, Epstein S E. Bone-marrow-derived cells for enhancing collateral development: mechanisms, animal data, and initial clinical experiences. Circ Res. 2004; 95(4):354-363.
9. Leedham S J, Brittan M, McDonald S A, Wright N A. Intestinal stem cells. J Cell Mol Med. 2005; 9(1):11-24.
10. Togel F, Hu Z, Weiss K, Isaac J, Lange C, Westenfelder C. Administered mesenchymal stem cells protect against ischemic acute renal failure through differentiation-independent mechanisms. Am J Physiol Renal Physiol. 2005; 289(1):F31-42.
11. Patschan D, Plotkin M, Goligorsky M S. Therapeutic use of stem and endothelial progenitor cells in acute renal injury: ca ira. Curr Opin Pharmacol. 2006; 6(2):176-183.
12. Miyahara Y, Nagaya N, Kataoka M, Yanagawa B, Tanaka K, Hao H, Ishino K, Ishida H, Shimizu T, Kangawa K, Sano S, Okano T, Kitamura S, Mori H. Monolayered mesenchymal stem cells repair scarred myocardium after myocardial infarction. Nat Med. 2006; 12(4):459-465.
13. Gnecchi M, He H, Noiseux N, Liang O D, Zhang L, Morello F, Mu H, Melo L G, Pratt R E, Ingwall J S, Dzau V J. Evidence supporting paracrine hypothesis for Akt-modified mesenchymal stem cell-mediated cardiac protection and functional improvement. Faseb J. 2006; 20(6):661-669.
14. Gnecchi M, He H, Liang O D, Melo L G, Morello F, Mu H, Noiseux N, Zhang L, Pratt R E, Ingwall J S, Dzau V J. Paracrine action accounts for marked protection of ischemic heart by Akt-modified mesenchymal stem cells. Nat Med. 2005; 11(4):367-368.
15. Mayer H, Bertram H, Lindenmaier W, Korff T, Weber H, Weich H. Vascular endothelial growth factor (VEGF-A) expression in human mesenchymal stem cells: autocrine and paracrine role on osteoblastic and endothelial differentiation. J Cell Biochem. 2005; 95(4):827-839.
16. Nakagami H, Maeda K, Morishita R, Iguchi S, Nishikawa T, Takami Y, Kikuchi Y, Saito Y, Tamai K, Ogihara T, Kaneda Y. Novel autologous cell therapy in ischemic limb disease through growth factor secretion by cultured adipose tissue-derived stromal cells. Arterioscler Thromb Vasc Biol. 2005; 25(12):2542-2547.
17. Van Overstraeten-Schlogel N, Beguin Y, Gothot A. Role of stromal-derived factor-1 in the hematopoietic-supporting activity of human mesenchymal stem cells. Eur J Haematol. 2006.
18. Cheng L, Qasba P, Vanguri P, Thiede M A. Human mesenchymal stem cells support megakaryocyte and pro-platelet formation from CD34(+) hematopoietic progenitor cells. J Cell Physiol. 2000; 184(1):58-69.
19. Lian Q, Lye E, Suan Yeo K, Khia Way Tan E, Salto-Tellez M, Liu T M, Palanisamy N, El Oakley R M, Lee E H, Lim B, Lim S K. Derivation of Clinically Compliant MSCs from CD105+, CD24− Differentiated Human ESCs. Stem Cells. 2007; 25(2):425-436.
20. Sze S K, de Kleijn D P, Lai R C, Khia Way Tan E, Zhao H, Yeo K S, Low T Y, Lian Q, Lee C N, Mitchell W, El Oakley R M, Lim S K. Elucidating the secretion proteome of human embryonic stem cell-derived mesenchymal stem cells. Mol Cell Proteomics. 2007; 6(10):1680-1689.
21. Pan B T, Johnstone R M. Fate of the transferrin receptor during maturation of sheep reticulocytes in vitro: selective externalization of the receptor. Cell. 1983; 33(3):967-978.
22. Fevrier B, Raposo G. Exosomes: endosomal-derived vesicles shipping extracellular messages. Curr Opin Cell Biol. 2004; 16(4):415-421.
23. Shen V, Kiledjian M. A view to a kill: structure of the RNA exosome. Cell. 2006; 127(6):1093-1095.
24. Johnstone R M. The Jeanne Manery-Fisher Memorial Lecture 1991. Maturation of reticulocytes: formation of exosomes as a mechanism for shedding membrane proteins. Biochem Cell Biol. 1992; 70(3-4):179-190.
25. Denzer K, Kleijmeer M J, Heijnen H F, Stoorvogel W, Geuze H J. Exosome: from internal vesicle of the multi-vesicular body to intercellular signaling device. J Cell Sci. 2000; 113 Pt 19:3365-3374.
26. de Gassart A, Geminard C, Hoekstra D, Vidal M. Exosome secretion: the art of reutilizing nonrecycled proteins? Traffic (Copenhagen, Denmark). 2004; 5(11):896-903.
27. Pelchen-Matthews A, Raposo G, Marsh M. Endosomes, exosomes and Trojan viruses. Trends Microbiol. 2004; 12(7):310-316.
28. Pilzer D, Gasser O, Moskovich O, Schifferli J A, Fishelson Z. Emission of membrane vesicles: roles in complement resistance, immunity and cancer. Springer Semin Immunopathol. 2005; 27(3):375-387.
29. Aoki N. Regulation and functional relevance of milk fat globules and their components in the mammary gland. Biosci Biotechnol Biochem. 2006; 70(9):2019-2027.
30. Delcayre A, Le Pecq J B. Exosomes as novel therapeutic nanodevices. Curr Opin Mol Ther. 2006; 8(1):31-38.
31. Johnstone R M. Exosomes biological significance: A concise review. Blood Cells Mol Dis. 2006; 36(2):315-321.
32. Keller S, Sanderson M P, Stoeck A, Altevogt P. Exosomes: from biogenesis and secretion to biological function. Immunol Lett. 2006; 107(2):102-108.
33. van Niel G, Porto-Carreiro I, Simoes S, Raposo G. Exosomes: a common pathway for a specialized function. J Biochem (Tokyo). 2006; 140(1):13-21.
34. Hao S, Moyana T, Xiang J. Review: cancer immunotherapy by exosome-based vaccines. Cancer biotherapy & radiopharmaceuticals. 2007; 22(5):692-703.
35. Subra C, Laulagnier K, Perret B, Record M. Exosome lipidomics unravels lipid sorting at the level of multivesicular bodies. Biochimie. 2007; 89(2):205-212.
36. Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol. 2007; 9(6):654-659.
37. Fevrier B, Vilette D, Laude H, Raposo G. Exosomes: a bubble ride for prions? Traffic (Copenhagen, Denmark). 2005; 6(1):10-17.
38. Mallegol J, van Niel G, Heyman M. Phenotypic and functional characterization of intestinal epithelial exosomes. Blood Cells Mol Dis. 2005; 35(1):11-16.

39. Porto-Carreiro I, Fevrier B, Paquet S, Vilette D, Raposo G. Prions and exosomes: from PrPc trafficking to PrPsc propagation. Blood Cells Mol Dis. 2005; 35(2):143-148.
40. Soderberg A, Barral A M, Soderstrom M, Sander B, Rosen A. Redox-signaling transmitted in trans to neighboring cells by melanoma-derived TNF-containing exosomes. Free Radic Biol Med. 2007; 43(1):90-99.
41. Calzolari A, Raggi C, Deaglio S, Sposi N M, Stafsnes M, Fecchi K, Parolini I, Malavasi F, Peschle C, Sargiacomo M, Testa U. TfR2 localizes in lipid raft domains and is released in exosomes to activate signal transduction along the MAPK pathway. J Cell Sci. 2006; 119(Pt 21):4486-4498.
42. de Gassart A, Geminard C, Fevrier B, Raposo G, Vidal M. Lipid raft-associated protein sorting in exosomes. Blood. 2003; 102(13):4336-4344.
43. London E, Brown D A. Insolubility of lipids in triton X-100: physical origin and relationship to sphingolipid/cholesterol membrane domains (rafts). Biochim Biophys Acta. 2000; 1508(1-2):182-195.
44. Fevrier B, Vilette D, Archer F, Loew D, Faigle W, Vidal M, Laude H, Raposo G. Cells release prions in association with exosomes. Proc Natl Acad Sci USA. 2004; 101(26): 9683-9688.
45. Keller S, Rupp C, Stoeck A, Runz S, Fogel M, Lugert S, Hager H D, Abdel-Bakky M S, Gutwein P, Altevogt P. CD24 is a marker of exosomes secreted into urine and amniotic fluid. Kidney Int. 2007; 72(9):1095-1102.
46. Birnbaum Y, Hale S L, Kloner R A. Differences in reperfusion length following 30 minutes of ischemia in the rabbit influence infarct size, as measured by triphenyltetrazolium chloride staining J Mol Cell Cardiol. 1997; 29(2):657-666.
47. Timmers L, Sluijter J P, Verlaan C W, Steendijk P, Cramer M J, Emons M, Strijder C, Grundeman P F, Sze S K, Hua L, Piek J J, Borst C, Pasterkamp G, de Kleijn D P. Cyclooxygenase-2 inhibition increases mortality, enhances left ventricular remodeling, and impairs systolic function after myocardial infarction in the pig. Circulation. 2007; 115(3):326-332.
48. Steendijk P, Baan J, Jr., Van der Velde E T, Baan J. Effects of critical coronary stenosis on global systolic left ventricular function quantified by pressure-volume relations during dobutamine stress in the canine heart. J Am Coll Cardiol. 1998; 32(3):816-826.

REFERENCES (INCLUDING FOR EXAMPLES 31 TO 47)

Caplan, A. I., and Dennis, J. E. (2006a). Mesenchymal stem cells as trophic mediators. J Cell Biochem 98, 1076-1084.
Caplan, A. I., and Dennis, J. E. (2006b). Mesenchymal stem cells as trophic mediators. J Cell Biochem.
Fevrier, B., and Raposo, G. (2004). Exosomes: endosomal-derived vesicles shipping extracellular messages. Curr Opin Cell Biol 16, 415-421.
Gnecchi, M., He, H., Liang, O. D., Melo, L. G., Morello, F., Mu, H., Noiseux, N., Zhang, L., Pratt, R. E., Ingwall, J. S., et al. (2005). Paracrine action accounts for marked protection of ischemic heart by Akt-modified mesenchymal stem cells. Nat Med 11, 367-368.
Gnecchi, M., He, H., Noiseux, N., Liang, O. D., Zhang, L., Morello, F., Mu, H., Melo, L. G., Pratt, R. E., Ingwall, J. S., et al. (2006). Evidence supporting paracrine hypothesis for Akt-modified mesenchymal stem cell-mediated cardiac protection and functional improvement. Faseb J 20, 661-669.
Keller, S., Sanderson, M. P., Stoeck, A., and Altevogt, P. (2006). Exosomes: from biogenesis and secretion to biological function. Immunol Lett 107, 102-108.
Lian, Q., Lye, E., Suan Yeo, K., Khia Way Tan, E., Salto-Tellez, M., Liu, T. M., Palanisamy, N., El Oakley, R. M., Lee, E. H., Lim, B., et al. (2007). Derivation of Clinically Compliant MSCs from CD105+, CD24− Differentiated Human ESCs. Stem Cells 25, 425-436.
Liu, C. H., and Hwang, S. M. (2005). Cytokine interactions in mesenchymal stem cells from cord blood. Cytokine 32, 270-279.
Minguell, J. J., and Erices, A. (2006). Mesenchymal stem cells and the treatment of cardiac disease. Exp Biol Med (Maywood) 231, 39-49.
Olver, C., and Vidal, M. (2007). Proteomic analysis of secreted exosomes. Sub-cellular biochemistry 43, 99-131.
Pittenger, M. F., and Martin, B. J. (2004). Mesenchymal stem cells and their potential as cardiac therapeutics. Circ Res 95, 9-20.
Saraste, A., Pulkki, K., Kallajoki, M., Henriksen, K., Parvinen, M., and Voipio-Pulkki, L. M. (1997). Apoptosis in human acute myocardial infarction. Circulation 95, 320-323.
Schafer, R., and Northoff, H. (2008). Cardioprotection and cardiac regeneration by mesenchymal stem cells. Panminerva medica 50, 31-39.
Smalheiser, N. R. (2007). Exosomal transfer of proteins and RNAs at synapses in the nervous system. Biology direct 2, 35.
Sze, S. K., de Kleijn, D. P., Lai, R. C., Khia Way Tan, E., Zhao, H., Yeo, K. S., Low, T. Y., Lian, Q., Lee, C. N., Mitchell, W., et al. (2007). Elucidating the secretion proteome of human embryonic stem cell-derived mesenchymal stem cells. Mol Cell Proteomics 6, 1680-1689.
Taylor, D. D., and Gercel-Taylor, C. (2008). MicroRNA signatures of tumor-derived exosomes as diagnostic biomarkers of ovarian cancer. Gynecol Oncol 110, 13-21.
Thery, C., Zitvogel, L., and Amigorena, S. (2002). Exosomes: composition, biogenesis and function. Nat Rev Immunol 2, 569-579.
Timmers, L., Lim, S.-K., Arslan, F., Armstrong, J. S., Hoefler, I. E., Doevendans, P. A., Piek, J. J., El Oakley, R. M., Choo, A., Lee, C. N., et al. (2008). Reduction of myocardial infarct size by human mesenchymal stem cell conditioned medium. Stem Cell Research 1, 129-137.
Valadi, H., Ekstrom, K., Bossios, A., Sjostrand, M., Lee, J. J., and Lotvall, J. O. (2007). Exosome-mediated transfer of mRNAs and microRNAs is a novel mechanism of genetic exchange between cells. Nat Cell Biol 9, 654-659.
Zimmet, J. M., and Hare, J. M. (2005). Emerging role for bone marrow derived mesenchymal stem cells in myocardial regenerative therapy. Basic Res Cardiol 100, 471-481.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

The invention claimed is:

1. A method of promoting wound healing, the method comprising administering to an individual in need thereof a pharmaceutical composition comprising an exosome derived from a mesenchymal stem cell (MSC), wherein the exosome is isolated from an MSC-conditioned serum-free medium, and wherein the exosome has a size of between 50 nm and 100 nm as determined by electron microscopy.

2. The method of claim 1, in which the pharmaceutical composition comprises a pharmaceutically acceptable carrier.

3. The method of claim 1, in which the pharmaceutical composition is injected.

4. The method of claim 1, in which the exosome:
   (a) comprises a complex of molecular weight >100 kDa, comprising proteins of <100 kDa;
   (b) comprises a complex of molecular weight >300 kDa, comprising proteins of <300 kDa;
   (c) comprises a complex of molecular weight >1000 kDa;
   (d) has a size of between 2 nm and 200 nm, as determined by filtration against a 0.2 pM filter and concentration against a membrane with a molecular weight cut-off of 10 kDa; or
   (e) a hydrodynamic radius of below 100 nm, as determined by laser diffraction or dynamic light scattering.

* * * * *